(12) United States Patent
Barry et al.

(10) Patent No.: US 9,944,996 B2
(45) Date of Patent: Apr. 17, 2018

(54) EIF2γ GENE AS A DIAGNOSTIC TARGET FOR THE IDENTIFICATION OF FUNGAL AND YEAST SPECIES

(75) Inventors: Thomas Gerard Barry, Kinarva (IE); Majella Maher, Moycullen (IE); Terry James Smith, Galway (IE); Marcin Jankiewicz, Galway (IE); Louise O'Connor, Moycullen (IE); Nina Tuite, Galway (IE); Sinead Lahiff, Gort (IE)

(73) Assignee: National University of Ireland, Galway, Galway (IE)

( * ) Notice: Subject to any disclaimer, the term of this patent is extended or adjusted under 35 U.S.C. 154(b) by 1287 days.

(21) Appl. No.: 12/997,479

(22) PCT Filed: Jun. 15, 2009

(86) PCT No.: PCT/EP2009/057337
§ 371 (c)(1),
(2), (4) Date: May 10, 2011

(87) PCT Pub. No.: WO2009/150241
PCT Pub. Date: Dec. 17, 2009

(65) Prior Publication Data
US 2011/0218335 A1 Sep. 8, 2011

(30) Foreign Application Priority Data

Jun. 13, 2008 (IE) .................................... 2008/0490

(51) Int. Cl.
*C12Q 1/68* (2006.01)

(52) U.S. Cl.
CPC .................................. *C12Q 1/6895* (2013.01)

(58) Field of Classification Search
None
See application file for complete search history.

(56) References Cited

U.S. PATENT DOCUMENTS

| 6,747,137 B1 * | 6/2004 | Weinstock et al. ........... 536/23.1 |
| 7,504,490 B1 * | 3/2009 | Weinstock ............. C07K 14/38 |
| | | 435/252.3 |
| 2001/0053519 A1 * | 12/2001 | Fodor et al. ..................... 435/6 |

FOREIGN PATENT DOCUMENTS

| WO | WO-02/053728 | 7/2002 | |
| WO | WO 02086090 A2 * | 10/2002 | ............. C07K 14/38 |

OTHER PUBLICATIONS

Carlini et al. Viability and preliminary in vivo characterization of site-directed mutants of *Escherichia coli* single-stranded DNA-binding protein. Molecular Microbiology 10(5):1067-1075 (1993).*
Pisarevskii et al. Fluorescence spectrum and quantum yield of DNA in solution. Zhurnal Prikladnoi Spektroskopii 5(5):621-624 (1966).*
ABZ32029 [online] Jan. 30, 2003 retrieved from the DGENE database on STN.*
AR550600 [online] Oct. 10, 2004 retrieved from the EMBL database.*
Hannig et al (Molecular and Cellular Biology 13(1):506-520 (1993)).*
Alone et al (The Journal of Biological Chemistry 281(18):12636-12644, May 5, 2006).*
Krauss et al (Molecular Biology and Evolution 22(1):74-84, Jan. 2005).*
Partial search results for SEQ ID No. 3 (report generated Dec. 25, 2016; 3 pages).*
International Search Report and Written Opinion (ISA/EP) for PCT International Application No. PCT/EP2009/057337, dated Feb. 16, 2010, 20 pages.

* cited by examiner

*Primary Examiner* — Samuel C Woolwine
(74) *Attorney, Agent, or Firm* — Foley & Lardner LLP; Antoinette F. Konski; Peng Sun

(57) ABSTRACT

The current invention relates to a diagnostic kit for a yeast or fungal species comprising at least one oligonucleotide probe capable of binding to at least a portion of the eIF2y gene or its corresponding mRNA.

9 Claims, 29 Drawing Sheets

ATGTCATACGACGATATAGAAAATGCCACTCCTGATATTGTTATTGGGAGTACTATAGA
GGAACCTGAAGAAGATTACCAAGTGGAAAGTGACAATGAGTTACAAGCCGCAGACCATG
AGTCATCGCAAATAAATGAAGAATCAGCCAAAGGCAAAAAGTCAGTTGCATTACTGGA
TTGGATGAAGACGAGGAAAATGCAGAGGAATTGGCCAGAAAGGAGTTTGAAGAAGGTGG
TGGATTGCCTGAACAACCAGAAAACCCAGATTTCAATGAGTTAACACCTTTATCTCCCG
AGATTATCAACAGGCAAGCCACCATTAATATTGGTACCATTGGTCATGTCGCCCACGGG
AAGTCTACTGTTGTCAGGGCTATCTCTGGTGTCCAGACCGTTCGTTTCAAGGATGAATT
AGAAAGAAACATTACTATCAAGTTAGGTTACGCCAATGCCAAAATTTACAAATGTGATA
ACCCAGAGTGTCCAGAACCAGATTGTTACAGATCATTCAAATCAGATAAGGAAATAAGA
CCAAAATGTCAAAGAGCTGGCTGTGACGGTCGCTACAAATTGTTAAGACATGTCTCTTT
TGTTGATTCTCCAGGACATGATATTTTGATGAGTACTATGTTGTCAGGTGCTGCCCTGA
TGGATGCCGCCTTGTTGTTGATTGCCGGTAATGAAAGTTGTCCACAACCCCAGACTTCT
GAGCATTTGGCTGCCATTGAAATTATGAAATTGAAACATGTTATTATTTTGCAAAATAA
AGTTGATTTGATGAGAGAAGAATCAGCCTTGGAACACGAAAAATCTATCATTCAGTTTA
TTAGAGGTACAATTGCCGATAATGCTCCGATCGTGCCTATTTCTGCTCAATTGAAATAC
AACATTGATGCAGTGAATCAATTTATTGTTAACTACATACCTGTGCCAATGAGAGACTT
TACTGCTTCACCAAGATTGATCGTTATCAGATCTTTCGATGTGAACAAGCCTGGTGCAG
ATGTAGACGAATTGAAACGAGGTGTTGCAGGTGGTTCTATTTTGACTGGTGTTTTTAAG
ATTGGTGATGAGATCGAGATTAGACCTGGTATCGTCACCAAAGATGATCAAGGAAAGAT
TCAATGTAAACCTATATTCTCGAACGTGGTTTCCTTGTTTGCTGAGCATAACGATTTGA
AATTGCTGTTCCTGGTGGTTTGATTGGTGTTGGTACTAAAGTTGATCCTACGTTGTGT
AGGGCTGATAGATTGGTTGGTCAAGTTGTTGGTGCAAAAGGAAACTTGCCCTCTATTTA
CGCTGATATTGAGATAAACTATTTCCTATTAAGAAGATTGTTGGGTGTCAAAACTGAAG
GTCAAAAGCAAGGTGCTAAAGTTCGTAAGTTGGAACAATCTGAAGTGTTGATGGTAAAT
ATTGGTTCTACTGCAACTGGTGCTAGAGTGGTGCTGTTAAAGCAGATATGGCTCGTTT
ACAATTGACTACACCAGCCTGTACAGAAATCAACGAAAAAATTGCGTTGTCTAGACGTA
TTGAAAAGCATTGGCGTTTGATTGGTTGGGCCACTATCAAGAAAGGTACAGCATTAGAA
CCAATTTCTTAA

FIG. 1

```
35  CTTGGATGCGGCGAACGGCCAGGATGATATTGAAGAACAGGAACGTCTTGACGTGGAAG
    AGAAGCCCCTTAAGTCTGCGATGAAGAAAGGTGCAGCGCCCCCTGCTCCTCAGCCCAAG
    CGTCCAGAACTCCCCGAGCAGCCCGACCCAGAGACTCTCGATTTGTCGACGCTCACACC
    TCTGTCGCCCGAAATTATTGCGCGCCAGGCCAGAATCAACATCGGTACTATCGGACACG
    TCGCACACGGCAAGTCGACTGTTGTGAAGGCTATCTCGGAGGTGCAGACTGTCCGGTTC
40  AAAAATGAGTTGGAGCGTAACATTACCATCAAGCTTGGTTATGCCAACGCGAAGATCTA
    CAAGTGCGACAACCCTGGGTGCCCGCGCCCGACGTGCTTCAAGAGTTACAAGAGTGAGA
    AGGAGATCGACCCTCCATGTGAGAGAGAAGGATGCACAGGTCGTTACAGATTGTTGAGA
    CATGTCTCGTTCGTTGACTGCCCTGGGCACGATATTCTCATGAGTACCATGTTGTCAGG
    TGCCGCCGTCATGGACGCCGCCCTTTTGCTGATTGCCGGAAAACGAAGCTTCCCCCAGC
    CTCAGACTTCCGAGCACTTAGCAGCTATTGAAATCATGAAGCTCAGCCATATCATCATT
45  CTGCAGAACAAGGTTGATCTGATGAGGGAAGACGGTGCTCTGCAACATTACCAATCAAT
    CCTGAAGTTCATTCGTGGTACTGTTGCCGATGGCTCTCCTATCATTCCCATCTCTGCTC
    AGCTCAAGTACAACATCGACGCTGTCAACGAATACCTTGTCTCGCACATCCCAGTTCCC
    GTCCGTGACTTCACTGCTTCGCCTCACATGATTGTCATTCGTTCCTTCGACGTCAACAA
    ACCCGGTGCGGAGATCGATGAGTTGAAGGGTGGTGTTGCAGGTGGCTCTATCCTCACTG
    GTGTGCTGAAGCTGAACGACGAGATTGAAATTCGCCCCGGTCTCGTTACCAAGGATGAG
    AACGGAAAGATTCAGTGCCGCCCCATCTTCTCGCGTGTCGTCTCGCTCTTCGCTGAGCA
5   CAACGATCTGAAGTTCGCTGTCGCTGGTGGTCTAATCGGTGTCGGAACCCGTGTCGACC
    CTACCCTGTGCCGTGCCGATCGTCTTGTTGGTTTCGTCCTGGGTCACCGTCGCCGTTTG
    CCAGCCATCTACACTGAACTGGAGGTCAACTACTTCCTCCTGCGTCGTCTGCTCGGTGT
    CAAGACGCCGACGGCAAGCAGGCCAAGGTCGCCAAGCTCACCAAGAACGAAGTCCTCA
    TGGTTAACATCGGCTCTACGGCTACTGGTGCTAAGGTTATGGGTGTGAAGGCTGATGCT
10  GCCAAGCTCAGCTTGACCAGCCCGGCTTGTACAGAGATTGGAGAGAAGATTGCTATCAG
    CCGGAGAATTGACAAGCATTGGCGTCTGATCGGCTGGGCCAACATTGTCGCTGGCAACA
    CTCTTGAGCCCATTCTGAACTAG
```

FIG. 2

```
ATGTCATACGACGATATAGAAAATGCCACTCCTGATATTGTTATTGGGAGTACTATAGAGGAACCTGAAGA
AGATTACCAAGTGGAAAGTGACAATGAGTTACAAGCCGCAGACCATGAGTCATCGCAAATAAATGAAGAAT
CAGCCAAAAGCAAAAAGTCAGTTGCATTTACTGGATTGGATGAAGGACGAGGAAAATGCAGAGGAATTGGCC
AGAAAGGAGTTTGAAGAAGGTGGTGGATTGCCTGAACAACCAGAAAACCCAGATTTCAATGAGTTAACACC
TTTATCTCCCGAGATTATCAACAGGCAAGCCACCATTAATATTGGTACCATGGTCATGTCGCCCACGGGA
AGTCTACTGTTGTCAGGGCTATCTCTGGTGTCCAGACCGTTCGTTTCAAGGATGAATTAGAAAGAAACATT
ACTATCAAGTTAGGTTACGCCAATGCCAAAATTTACAAATGTGATAACCCAGAGTGTCCAGAACCAGATTG
TTACAGATCATTCAAATCAGATAAGGAAATAAGACCAAAATGTCAAAGAGCTGGCTGTGACGGTCGCTACA
AATTGTTAAGACATGTCTCTTTTGTTGATTGTCCAGGACATGATATTTTGATGAGTACTATGTTGTCAGGT
GCTGCCGTGATGGATGCCGCCTTGTTGTTGATTGCCGGTAATGAAAGTTGTCCACAACCCCAGACTTCTGA
GCATTTGGCTGCCATTGAAATTATGAAATTGAAACATGTTATTATTTTGCAAAATAAAGTTGATTTGATGA
CAGAAGAATCAGCCTTGGAACACGAAAAATCTATCATTCAGTTTATTAGAGGTACAATTGCCGATAATGCT
CCGATCGTGCCTATTTCTGCTCAATTGAAATACAACATTCATGCAGTGAATCAATTTATTGTTAACTACAT
ACCTGTGCCAATGAGAGACTTTACTGCTTCACCCAAGATTGATCGTTATCAGATCTTTCGATGTGAACAAGC
CTGGTGCAGATGTAGACGAATTGAAAGGAGGTGTTGCAGGTGGTTCTATTTTGACTGGTGTTTTTAAGATT
GGTGATGAGATCGAGATTAGACCTGGTATCGTCACCAAAGATGATCAAGGAAAGATTCAATGTAAACCTAT
ATTCTCGAACGTGGTTTCCTTGTTTGCTGAGCATAACGATTTGAAAATTTGCTGTTCCTGGTGGTTTGATTG
GTGTTGGTACTAAAGTTGATCCTACGTTGTGTAGGGCTGATAGATTGGTTGGTCAAGTTGTTGGTGCAAAA
GGAAACTTGCCCTCTATTTACGCTGATATTGAGATAAACTATTTCCTATTAAGAAGATTGTTGGGTGTCAA
AACTGAAGGTCAAAAGCAAGGTGCTAAAGTTCGTAAGTTGGAACAATCTGAAGTGTTGATGGTAAATATTG
GTTCTACTGCAACTGGTGCTAGAGTGGTTGCTGTTAAAGCAGATATGGCTCGTTTACAATTGACTACACCA
GCCTGTACAGAAATCAACGAAAAAATTGCGTTGTCTAGACGTATTGAAAAGCATTGGCGTTTGATTGGTTG
GGCCACTATCAAGAAAGGTACAGCAATTAGAACCAATTTCTTAA
```

FIG. 5

```
ATGTCTGATTTGCAAGATCAAGAGCCAACTATTATTATCAAATGGTGATCTTCCACCAGTAGAAGAAGAGGA
AGTCTATGAGCAGGAAGAGCAAGAGGAAGTTGTTGAGGAGAAGCCAAAGAAGAAAGTTGCCTTTACCGGTC
TAGAAGATGGTGAATCTGAGGAAGAGAAGAGAAAGAGAGAGTTTGAAGAAGGTGGTGGATTGCCAGAGCAG
CCAGAAAACCCAGACTTTACTAAGTTGAACCCACTTTCTGCTGAGATTATTAACAGACAAGCTACTATCAA
CATCGGTACTATTGTCATGTCGCTCACGGTAAGTCTACTGTTGTCAGAGCCATCTCTGGTGTCCAAACCG
TTCGTTTCAAGGATGAGTTGGAACGTAACATTACTATCAAGCTGGGTTATGCCAATGCTAAGATATATAAG
TGTCAAGAGCCTACATGTCCAGAACCAGACTGTTACAGATCTTTCAAGTCTGACAAAGAAATTAATCCAAA
GTGTCAAAGACCAGGTTGCCCAGGCCGTTACAAACTTGTTCGTCACGTCTCTTTCGTCGATTGTCCAGGTC
ACGATATTCTAATGAGTACTATGTTGTCCGGTGCCGCTGTCATGGACGCAGCCTTGTTATTGATCGCCGGT
AATGAATCTTGTCCACAACCTCAAACTTCTGAACATTTGGCTGCCATTGAAATCATGAAGTAAAGCACGT
TATTATTCTACAGAACAAGGTCGATTAATGCGTGAAGAAAGCGCACTAGAACATGAAAGTCTATCCTGA
AATTTATCGAGGTACTATTGCTGACGTCCTCCAATTGTCCCAATTTCCGCTCAATTGAAATACAACATC
GATGCAGTCAATGAATTTATCGTGAAGACTATCCCTGTTCCACCAAGAGATTTCATGCTTTCTCCACGTTT
GATTGTCATTCGTTCTTTCGATGTTAACAAGCCAGGTGCTGAAATCGATGATTTGAAGGGTGGTGTTGCAG
GTGGTTCCATCTTGAACGGTGTGTTCAAGTTGGGTGATGAGATTGAAATTAGACCAGGTATTGTCACTAAG
GATGATAAGGGTAAGATCCAATGTAAGCCAATTTTCTCCAACATTGTCTCTCTATTTGCTGAACAAAATGA
CTTGAAGTTTGCAGTCCCAGGTGGTCTGATTGGTGTTGGTACAAAGGTCGATCCTACCTTATGTAGAGCTG
ATCGTCTTGTCGGTCAAGTTGTCGGTGCCAAGGGTCACCTACCAAGCATTTACAAGATATTGAAATCAAC
TACTTCCTACTGCGTGTCTATTAGGTGTTAAGACTGAGAAACAAGCCAAGGTCAGAAAGCTGGTTGCCAA
CGAAGTTCTATGGTTAACATTGGTTCTACTGCCACTGGTGCCCGTGTCGTTGCTGTCAAGGCTGATATGG
CTAGATTGCAACTAACATCCCCAGCATGTACAGAAATCAATGAAAAGATTGCTCTCTCTAGACGTATTGAC
AAGCACGGCGTTTAATTGGTTGGGCTACAATCAAGAAAGGTACCACTTTGGAATCAGTTGTCTAA
```

FIG. 6

>P-604\(EF)\(CaneIF2-F) eIF2 γ sequence generated for *C.parapsilosis*
GTTCAAGCACGTTATTATTTTGCAAAACAAAGTTGATTTAATGAGAAAGGAGTCAGCTTTGGAACATGAAA
AGTCCATCATTCAGTTCATCAGAGGTACTATAGCTGATGGTGCCCCAATTGTTCCAATTTCAGCACAATTG
AAGTATAATATCGACGCCGTCAATCAATTCATCGTAAACTCAATACCAGTTCCAGTCAGGGACTTTACTGC
ATCCCCTAGGTTAATTGTTATTAGGTCTTTTGATGTGAACAAACCTGGTGCTGACGTTGATGATTTGAAAG
GAGCTGTTGCAGGTGGTTC

FIG. 7

>T94\(EF)\(CaneIF2-F) eIF2 γ sequence generated for *C.tropicalis*
GTCATKATTTTGCAGAACAAGGTCGATTTGATGAGAGAAGAATCTGCCTTGGAACATGAGAAATCCATTCT
TCAATTCATCAGAGGTACTATTGCAGACAATGCTCCTATTGTCCCAATTTCTGCCCAATTGAAATACAACA
TCGATGCCGTTAACCAATTTATTGTCAATTATATCCCAGTTCCATTGAGAGACTTTTCCGCTTCCCCAAGA
TTGATTGTCATCAGATCTTTTGATGTCAACAAGCCAGGTTCCGATGTCGAAGACTTTGAAACGGGGTGTTGC
AGGTGGTTC

FIG. 8

>K573E\(EF)\(CaneIF2-F) eIF2 γ sequence generated for *C. krusei*
TGKTGTGATTKTACAAAATAAAGTTGATTTGATGAAGAAAGAAGCAGCTTTAGAGCACGAAAAATCTATTT
TGAAGTTTATCAAGGGTACTATTGCTGATGGTGCTCCTATTATCCCAATTTCTGCTCAGTTGAAATATAAC
ATTGATGCAGTTAACATGTGTATGGTCAAGTCTATTCCTGTTCCAATTAGAGACTTTACCGCAGTTCCAAG
ATTAATGGTTATTAGATCTTTCGATGTTAATAAGCCTGGTGCAGAAATTGCAGATTTGAAAGGTGGTGTTG
CAGGTGGTTC

FIG. 9

The amplified region of interest is underlined
>FUM7273\(AspEF-F) sequence generated for A. fumigatus
AGCGCCCCCTGCTCCTCAGCCGAAGCGTCCAGAACTCCCGGAGCAGCCGGACCCAGAGACTCTCGATTTGT
CGACGGTCACACCTCTGTCGCCCGAAATTATTGCGCGCCAGGCCACAATCAACATCGGTACTATCGGACAC
GTCGCACACGGCAAGTCGACTGTTGTGAAGGCTATCTCGGAGGTGCAGACTGTCCGGTTCAAAAATGAGTT
GGAGCGTAACATTAC

FIG. 15

The amplified region of interest is underlined
>FLA117.62(EF2) sequence generated for A. flavus
GCTGTACCCCTGTTTCTCAGCCCAAGCGGCCAGAGTTGCCCGAACAGCCAGACCCCGCTACCCTTGACCT
GTCGACCCTGACCCCTCTGTCGCCCGAAATCATTGCGCGCCAGGCCACTATTAACATTGGTACCATCGGAC
ACGTCGCTCACGGAAAGTCAACAGTGGTCAAGGCTATCTCAGAGGTTCAGACTGTCCGTTTCAAAAACGAG
TTGGAGCGTAACATTAC

FIG. 16

The amplified region of interest is underlined
>NIG6727\(AspEF-F) sequence generated for A. niger
TTCCTCCTCCCCAGCCCAAGCGGCCAGAGCTGCCCGAGCAGCCGAATCCGGAGACTCTGGACCTGTCCACC
CTGACTCCTTTGACCCCCCGAAATTATTGCGCGCCAAGCCACAATCAACATTGGCACCATCGGTCACGTCGC
TCACGGCAAGTCGACGGTCGTTAAGGCTATCTCCGAGGTCCAGACTGTCCGTTTCAAGAACGAGTTGGAGC
GTAACATTAC

FIG. 17

The amplified region of interest is underlined
>TER5677\(AspEF-F)
AGCCGAAGCGCCCAGAGCTTCCTGAACAACCCAACCCAGACACCCTCGATCTGTCGACGCTTACCCCTCTG
TCGCCCGAAATTATTGCGCGCCAGGCCACCATCAACATCGGTACCATTGGTCACGTCGCTCACGGAAAGTC
GACGGTTGTCAAGGCCATCTCAGAGGTCCAGACCGTGTCGATTCAAGAACGAGTTGGAGCGTAACATTAC

FIG. 18

*A. terreus* specificity. All three *A. terreus* samples detected with no cross-reactivity with the other 9 Aspergillus species. All sample included in triplicate.

*A. flavus* specificity. No cross-reactivity with any of the other Aspergillus species included in the assay. Samples in triplicate

*A. niger* specificity. No cross-reactivity with any of the other Aspergillus species included in the assay. Samples in triplicate

EIF2γ GENE AS A DIAGNOSTIC TARGET FOR THE IDENTIFICATION OF FUNGAL AND YEAST SPECIES

CROSS-REFERENCE TO RELATED APPLICATIONS

This application claims the benefit under 35 U.S.C. § 371 of PCT International Application No. PCT/EP2009/057337, filed Jun. 15, 2009, which in turn claims priority to Irish Application No. 2008/0490, filed Jun. 13, 2008, the contents of each which are hereby incorporated by reference in their entirety.

FIELD OF THE INVENTION

The present invention relates to nucleic acid primers and probes to detect one or more fungal and yeast species. More specifically the invention relates to the eIF2γ gene (also known as the EF-2 gene), the corresponding RNA, specific probes, primers and oligonucleotides related thereto and their use in diagnostic assays to detect and/or discriminate between fungal and yeast species.

BACKGROUND OF THE INVENTION

Yeast and fungal infections represent a major cause of morbidity and mortality among immunocompromised patients. The number of immunocompromised patients at risk of yeast and fungal infection continues to increase each year, as does the spectrum of fungal and yeast agents causing disease. Mortality from fungal infections, particularly invasive fungal infections, is 30% or greater, in certain risk groups. The array of available antifungal agents is growing; however, so too is the recognition of both intrinsic and emerging resistance to antifungal drugs. These factors are contributing to the increased need for cost containment in laboratory testing and have led to laboratory consolidation in testing procedures.

Invasive fungal infections are on the increase. In 2003, it was estimated that there were 9 million at risk patients, of which 1.2 million developed infection. *Candida* spp. and *Aspergillus* spp. now rank as the most prominent pathogens infecting immunosupressed patients. In particular, infections are common in the urinary tract, the respiratory system and the bloodstream, at the site of insertion of stents, catheters and orthopaedic joints. Approximately, 10% of the known *Candida* spp. have been implicated in human infection. Invasive candidiasis occurs when *candida* enters the bloodstream and it is estimated to occur at a frequency of 8/100,000 population in the US with a mortality rate of 40%. *Candida albicans* is the 4th most common cause of bloodstream infection. Aspergillosis usually begins as a pulmonary infection that can progress to a life-threatening invasive infection in some patients and has a mortality rate of greater than 90%. Emerging mycoses agents include *Fusarium, Scedosporium, Zygomycetes* and *Trichosporon* spp. ("*Stakeholder Insight: Invasive fungal infections*", Datamonitor, January 2004).

Immunocompromised patients, including transplant and surgical patients, neonates, cancer patients, diabetics and those with HIV/AIDs are at high risk of developing invasive fungal infections (Datamonitor report: Stakeholder opinion—Invasive fungal infections, options outweigh replacements 2004). A large number of severe cases of sepsis are reported each year. Despite improvements in its medical management, sepsis still constitutes one of the greatest challenges in intensive care medicine. Microorganisms (bacteria, fungi and yeast) responsible for causing sepsis are traditionally detected in hospital laboratories with the aid of microbiological culture methods with poor sensitivity (25-82%), which are very time-consuming, generally taking from two to five days to complete, and up to eight days for the diagnosis of fungal infections. Definitive diagnosis of infections caused by yeast or fungi is usually based on either, the recovery and identification of a specific agent from clinical specimens or microscopic demonstration of fungi with distinct morphological features. However, there are numerous cases where these methods fail to provide conclusive proof as to the infecting agent. In these instances, the detection of specific host antibody responses can be used, although again this can be affected by the immune status of the patient. Time is critical in the detection and identification of bloodstream infections typically caused by bacteria, yeasts or fungi. Effective treatment depends on finding the source of infection and making appropriate decisions about antibiotics or antifungals quickly and efficiently. Only after pathogens are correctly identified can targeted therapy using a specific antibiotic or antifungal begin. Many physicians would like to see the development of better in vitro amplification and direct detection diagnostic techniques for the early diagnosis of yeast and fungi ("*Stakeholder Insight: Invasive fungal infections*", Datamonitor, January 2004). Recently Roche™ launched a real time PCR based assay (Septifast™), for the detection of bacterial, fungal and yeast DNA in clinical samples. Therefore, there is a clear need for the development of novel rapid diagnostic tests for clinically significant bacterial and fungal pathogens for bioanalysis applications in the clinical sector. This has led the current inventors to identify novel fungal and yeast nucleic acid targets for application in Nucleic Acid Diagnostics (NAD) tests.

Fungal and yeast nucleic acid based diagnostics have focused heavily on the ribosomal RNA (rRNA) genes, RNA transcripts, and their associated DNA/RNA regions. The rRNA genes are highly conserved in all fungal species and they also contain divergent and distinctive intergenic transcribed spacer regions. Ribosomal rRNA comprises three genes: the large sub-unit gene (28S), the small sub-unit gene (18S) and the 5.8S gene. The 28S and 18S rRNA genes are separated by the 5.8S rRNA and two internal transcribed spacers (ITS1 and ITS2). Because the ITS region contains a high number of sequence polymorphisms, numerous researchers have concentrated their efforts on these as targets (Atkins and Clark, 2004). rRNA genes are also multicopy genes with >10 copies within the fungal genome.

A number of groups are working on developing new assays for fungal and yeast infections. US2004044193 relates to, amongst a number of other aspects, the transcription factor CaTEC1 of *Candida albicans*; inhibitors thereof, and methods for the diagnosis and therapy of diseases which are connected with a *Candida* infection; and also diagnostic and pharmaceutical compositions which contain the nucleotide sequences, proteins, host cells and/or antibodies. WO0183824 relates to hybridization assay probes and accessory oligonucleotides for detecting ribosomal nucleic acids from *Candida albicans* and/or *Candida dubliniensis*. U.S. Pat. No. 6,017,699 and U.S. Pat. No. 5,426,026 relate to a set of DNA primers, which can be used to amplify and speciate DNA from five medically important *Candida* species. U.S. Pat. No. 6,747,137 discloses sequences useful for diagnosis of *Candida* infections. EP 0422872 and U.S. Pat. No. 5,658,726 disclose probes based on 18S rRNA genes, and U.S. Pat. No. 5,958,693 discloses probes based on 28S rRNA, for diagnosis of a range of yeast and fungal species. U.S. Pat. No. 6,017,366 describes sequences based on chitin synthase gene for use in nucleic acid based diagnostics for a range of *Candida* species.

It is clear though, that development of faster, more accurate diagnostic methods are required, particularly in light of the selection pressure caused by modern antimicrobial treatments which give rise to increased populations of resistant virulent strains with mutated genome sequences. Methods that enable early diagnosis of microbial causes of infection enable the selection of a specific narrow spectrum antibiotic or antifungal to treat the infection (Datamonitor report: Stakeholder opinion—Invasive fungal infections, options outweigh replacements 2004; Datamonitor report: Stakeholder Opinion-Sepsis, under reaction to an overreaction, 2006). Eukaryotic initiation factor 2 (eIF2) is a heterotrimer composed of three subunits eIF2alpha (eIF2α), eIF2beta (eIF2β) and eIF2gamma (eIF2γ). eIF2 is the eukaryotic translation initiation factor 2, which is a heterotrimeric G-protein required for GTP-dependent delivery of initiator tRNA to the ribosome. The eIF2 gamma subunit (eif2γ) has a similar amino acid sequence to prokaryotic translation elongation factor EF-Tu which was patented as molecular diagnostics targets for micro-organisms (Alone and Dever, 2006; Dorris et al., 1995; Erickson et al., 1996 and 1997).

There are currently 171 sequences of eIF2γ available in NCBI GenBank database including 3 *Candida* spp. including 2 annotated eIF2γ sequences for *C. albicans* and one hypothetical protein for *C. glabrata* with 78% homology to *C. albicans* eIF2γ and 6 *Aspergillus* spp. sequences, 3 annotated as eIF2γ and 3 hypothetical sequences. The published sequences are approximately 1600 base pairs in length providing a number of sequence regions that are suitable for PCR primer and probe design for species identification of *Candida* and *Aspergillus* spp. For *Candida*, the inventors focussed on the region of the eIF2 gamma gene equivalent to base pair (bp) position 718 to by position 1040 in *C. albicans*. For *Aspergillus*, the inventors designed primers to amplify the region of the eIF2γ gene equivalent to by position 121 to by position 374 in *Aspergillus fumigatus*.

Definitions

"Synthetic oligonucleotide" refers to molecules of nucleic acid polymers of 2 or more nucleotide bases that are not derived directly from genomic DNA or live organisms. The term synthetic oligonucleotide is intended to encompass DNA, RNA, and DNA/RNA hybrids that have been manufactured chemically, or synthesized enzymatically in vitro.

An "oligonucleotide" is a nucleotide polymer having two or more nucleotide subunits covalently joined together. Oligonucleotides are generally about 10 to about 100 nucleotides. The sugar groups of the nucleotide subunits may be ribose, deoxyribose, or modified derivatives thereof such as OMe. The nucleotide subunits may be joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention.

A "target nucleic acid" is a nucleic acid comprising a target nucleic acid sequence. A "target nucleic acid sequence," "target nucleotide sequence" or "target sequence" is a specific deoxyribonucleotide or ribonucleotide sequence that can be hybridized to a complementary oligonucleotide.

An "oligonucleotide probe" is an oligonucleotide having a nucleotide sequence sufficiently complementary to its target nucleic acid sequence to be able to form a detectable hybrid probe:target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promoter sequences, restriction endonuclease recognition sites, or sequences that confer a desired secondary or tertiary structure such as a catalytic active site can be used to facilitate detection using the invented probes. An oligonucleotide probe optionally may be labelled with a detectable moiety such as a radioisotope, a fluorescent moiety, a chemiluminescent, a nanoparticle moiety, an enzyme or a ligand, which can be used to detect or confirm probe hybridization to its target sequence. Oligonucleotide probes are preferred to be in the size range of from about 10 to about 100 nucleotides in length, although it is possible for probes to be as much as and above about 500 nucleotides in length, or below 10 nucleotides in length.

A "hybrid" or a "duplex" is a complex formed between two single-stranded nucleic acid sequences by Watson-Crick base pairings or non-canonical base pairings between the complementary bases. "Hybridization" is the process by which two complementary strands of nucleic acid combine to form a double-stranded structure ("hybrid" or "duplex"). A "fungus" or "yeast" is meant any organism of the kingdom Fungi, and preferably, is directed towards any organism of the phylum Ascomycota.

"Complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine (T) or uracil (U), while guanine (G) ordinarily complements cytosine (C).

The term "stringency" is used to describe the temperature, ionic strength and solvent composition existing during hybridization and the subsequent processing steps. Those skilled in the art will recognize that "stringency" conditions may be altered by varying those parameters either individually or together. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid.

With "high stringency" conditions, nucleic acid base pairing will occur only between nucleic acid fragments that have a high frequency of complementary base sequences (for example, hybridization under "high stringency" conditions, may occur between homologs with about 85-100% identity, preferably about 70-100% identity). With medium stringency conditions, nucleic acid base pairing will occur between nucleic acids with an intermediate frequency of complementary base sequences (for example, hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

'High stringency' conditions are those equivalent to binding or hybridization at 42° C. in a solution consisting of 5×SSPE (43.8 g/l NaCl, 6.9 g/l NaH$_2$PO$_4$H$_2$O and 1.85 g/l EDTA, ph adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is used.

"Medium stringency' conditions are those equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42° C., when a probe of about 500 nucleotides in length is used.

'Low stringency' conditions are those equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C., when a probe of about 500 nucleotides in length is used.

In the context of nucleic acid in-vitro amplification based technologies, "stringency" is achieved by applying temperature conditions and ionic buffer conditions that are particular to that in-vitro amplification technology. For example, in the context of PCR and real-time PCR, "stringency" is achieved by applying specific temperatures and ionic buffer strength for hybridisation of the oligonucleotide primers and, with regards to real-time PCR hybridisation of the probe/s, to the target nucleic acid for in-vitro amplification of the target nucleic acid.

One skilled in the art will understand that substantially corresponding probes of the invention can vary from the referred-to sequence and still hybridize to the same target nucleic acid sequence. This variation from the nucleic acid may be stated in terms of a percentage of identical bases within the sequence or the percentage of perfectly complementary bases between the probe and its target sequence. Probes of the present invention substantially correspond to a nucleic acid sequence if these percentages are from about 100% to about 80% or from 0 base mismatches in about 10 nucleotide target sequence to about 2 bases mismatched in an about 10 nucleotide target sequence. In preferred embodiments, the percentage is from about 100% to about 85%. In more preferred embodiments, this percentage is from about 90% to about 100%; in other preferred embodiments, this percentage is from about 95% to about 100%

By "sufficiently complementary" or "substantially complementary" is meant nucleic acids having a sufficient amount of contiguous complementary nucleotides to form, under high stringency hybridization conditions, a hybrid that is stable for detection. Substantially complementary to can also refer to sequences with at least 90% identity to, e.g., 95, 96, 97, 98, 99, or 100% identity to, a given reference sequence.

The terms "identical" or percent "identity," in the context of two or more nucleic acids or polypeptide sequences, refer to two or more sequences or subsequences that are the same or have a specified percentage of amino acid residues or nucleotides that are the same (i.e., 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

By "nucleic acid hybrid" or "probe:target duplex" is meant a structure that is a double-stranded, hydrogen-bonded structure, preferably about 10 to about 100 nucleotides in length, more preferably 14 to 50 nucleotides in length, although this will depend to an extent on the overall length of the oligonucleotide probe. The structure is sufficiently stable to be detected by means such as chemiluminescent or fluorescent light detection, autoradiography, electrochemical analysis or gel electrophoresis. Such hybrids include RNA:RNA, RNA:DNA, or DNA:DNA duplex molecules.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

By "preferentially hybridize" is meant that under high stringency hybridization conditions oligonucleotide probes can hybridize their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of (for example *Candida*) and distinguish these species from other organisms. Preferential hybridization can be measured using techniques known in the art and described herein.

By "theranostics" is meant the use of diagnostic testing to diagnose the disease, choose the correct treatment regime and monitor the patient response to therapy. The theranostics of the invention may be based on the use of an NAD assay of this invention on samples, swabs or specimens collected from the patient.

OBJECT OF THE INVENTION

It is an object of the current invention to provide sequences and/or diagnostic assays to detect and identify one or more yeast and fungal species. The current inventors have made use of the eIF2γ gene sequence to design primers that are specific to *Candida* eIF2 γ genes and to *Aspergillus* eIF2γ genes. Such primers not only allow the detection of yeast and fungal species but also allow distinction between *Candida* and *Aspergillus* spp. This has an advantage over the prior art in that if one wants to identify a fungal pathogen in a sample, which contains *Candida* as a commensal, the approach of using universal primers may not be successful. There is a strong possibility that the *Candida* will outcompete the fungal pathogen in the amplification process and will be preferentially amplified, resulting in failure to detect the disease-causing pathogen. The current invention further provides for primers and probes that allow discrimination between different *Candida* species and among different *Aspergillus* species.

SUMMARY OF THE INVENTION

The present invention provides for a diagnostic kit for detection and identification of yeast and/or fungal species, comprising at least one oligonucleotide probe capable of binding to at least a portion of the eIF2 γ gene or its corresponding mRNA. The oligonucleotide probe may have a sequence substantially homologous to or substantially complementary to a portion of the eIF2 γ gene or its corresponding mRNA. It will thus be capable of binding or hybridizing with a complementary DNA or RNA molecule. The eIF2 γ gene may be a fungal eIF2 γ gene. The eIF2 γ gene may be a yeast eIF2 γ gene. The nucleic acid molecule may be synthetic.

The portion of the eIF2 γ gene may be equivalent to a portion of the region of the gene from base pair position 718 to 1040 of *C. albicans* eIF2 γ gene. The portion of the eIF2 γ gene may be equivalent to a portion of the region of the gene from base pair position 790 to 934 of *C. albicans* eIF2 γ gene. The portion of the eIF2 γ gene may be equivalent to a portion of the region of the gene from base pair position 872 to 972 of *C. glabrata* eIF2 γ gene. The portion of the eIF2 γ gene may be equivalent to a portion of the region of the gene from base pair position 151 to 274 of *C. parapsilosis* eIF2 γ gene. The portion of the eIF2 γ gene may be equivalent to a portion of the region of the gene from base pair position 140 to 270 of *C. tropicalis* eIF2 γ gene. The portion of the eIF2 γ gene may be equivalent to a portion of the region of the gene from base pair position 115 to 224 of *C. krusei* eIF2 γ gene. The portion of the eIF2 γ gene may be equivalent to a portion of the region of the gene from base pair position 121 to 374 of *A. fumigatus* eIF2 γ gene. The portion of the eIF2 γ gene may be equivalent to a portion of the region of the gene from base pair position 164 to 261 of *A. fumigatus* eIF2 γ gene. The portion of the eIF2 γ gene may be equivalent to a portion of the region of the gene from base pair position 155 to 252 of *A. flavus* eIF2 γ gene. The portion of the eIF2 γ gene may be equivalent to a portion of the region of the gene from base pair position 92 to 189 of *A. niger* eIF2 γ gene. The portion of the eIF2 γ gene may be equivalent to a portion of the region of the gene from base pair position 149 to 246 of *A. terreus* eIF2 γ gene. A skilled person will appreciate that sequences equivalent to these regions can be found in other organisms, but not necessarily in the same position.

The oligonucleotide probe may have a sequence of SEQ ID NO 1, 2, 84, 85, 86, 87, 88, 108, 109, 110, 111, 125 or 138, or a sequence substantially homologous to or substantially complementary to those sequences, which can also act as a probe for the eIF2 γ gene. The kit may comprise more than one such probe. In particular the kit may comprise a plurality of such probes. In addition the kit may comprise additional probes for other organisms, such as, for example, bacterial species or viruses.

The kit may further comprise at least one primer for amplification of at least a portion of the eIF2 γ gene. Suitably the kit may comprise at least one forward in vitro amplification primer and/or at least one reverse in vitro amplification primer, the forward amplification primer having a sequence selected from the group comprising SEQ ID NO 3, 5, 89, 91, 93, 95, 97, 104, 105, 112, 113, 114, 115, 116, 117, 118, 119, 120, 135 or 136 or a sequence being substantially homologous or complementary thereto which can also act as a forward amplification primer for the eIF2 γ gene, and/or the reverse amplification primer having a sequence selected from the group comprising SEQ ID NO 4, 6, 90, 92, 94, 96, 98, 106, 107, 121, 122, 123, 124 or 137 or a sequence being substantially homologous or complementary thereto which can also act as a reverse amplification primer for the eIF2 γ gene.

A kit useful for detecting a *Candida* eIF2γ polynucleotide comprises at least one oligonucleotide probe selected from the group comprising SEQ ID NOs: 1, 84, 85, 86, 87, 88 or 138 or which preferentially hybridizes to the same nucleotide sequence as is preferentially hybridized by SEQ ID NOs: 1, 84, 85, 86, 87, 88 or 138. The kit may further comprise at least one forward primer selected from the group comprising SEQ ID NOs: 5, 89, 91, 93, 95, 97, 135 or 136 or which preferentially hybridizes to the same nucleotide sequence as is preferentially hybridized by SEQ ID NOs: 5, 89, 91, 93, 95, 97, 135 or 136 and/or a reverse primer selected from the group comprising SEQ ID NOs: 6, 90, 92, 94, 96, 98, 137 or which preferentially hybridizes to the same nucleotide sequence as is preferentially hybridized by SEQ ID NOs: 6, 90, 92, 94, 96, 98 or 137.

A kit for detecting or identifying a *Candida alicans* eIF2γ polynucleotide comprises at least one oligonucleotide probe selected from the group comprising SEQ ID NO: 1, 84 or 138 or which preferentially hybridizes to the same nucleotide sequence as is preferentially hybridized by SEQ ID NO: 1, 84 or 138 and further comprises at least one forward primer selected from the group comprising SEQ ID NO: 5, 89, 135 or 136 or which preferentially hybridizes to the same nucleotide sequence as is preferentially hybridized by SEQ ID NO: 5, 89, 135 or 136 and/or at least one reverse primer selected from the group comprising SEQ ID NO: 6, 90 or 137. or which preferentially hybridizes to the same nucleotide sequence as is preferentially hybridized by SEQ ID NO: 6, 90, or 137.

A kit for detecting or identifying a *Candida glabrata* eIF2γ polynucleotide comprises at least one oligonucleotide probe selected from the group comprising SEQ ID NO: 85 or which preferentially hybridizes to the same nucleotide sequence as is preferentially hybridized by SEQ ID NO: 85 and further comprises at least one forward primer selected from the group comprising SEQ ID NO: 91 or which preferentially hybridizes to the same nucleotide sequence as is preferentially hybridized by SEQ ID NO: 91 and/or at least one reverse primer selected from the group comprising SEQ ID NO: 92 or which preferentially hybridizes to the same nucleotide sequence as is preferentially hybridized by SEQ ID NO: 92.

A kit for detecting or identifying a *Candida parapsilosis* eIF2γ polynucleotide comprises at least one oligonucleotide probe selected from the group comprising SEQ ID NO: 86 or which preferentially hybridizes to the same nucleotide sequence as is preferentially hybridized by SEQ ID NO: 86 and further comprises at least one forward primer selected from the group comprising SEQ ID NO: 93 or which preferentially hybridizes to the same nucleotide sequence as is preferentially hybridized by SEQ ID NO: 93 and/or at least one reverse primer selected from the group comprising SEQ ID NO: 94. or which preferentially hybridizes to the same nucleotide sequence as is preferentially hybridized by SEQ ID NO: 94.

A kit for detecting or identifying a *Candida tropicalis* eIF2γ polynucleotide comprises at least one oligonucleotide probe selected from the group comprising SEQ ID NO: 87 or which preferentially hybridizes to the same nucleotide sequence as is preferentially hybridized by SEQ ID NO: 87 and further comprises at least one forward primer selected from the group comprising SEQ ID NO: 95 or which preferentially hybridizes to the same nucleotide sequence as is preferentially hybridized by SEQ ID NO: 95 and/or at least one reverse primer selected from the group comprising SEQ ID NO: 96 or which preferentially hybridizes to the same nucleotide sequence as is preferentially hybridized by SEQ ID NO: 96.

A kit for detecting or identifying a *Candida krusei* eIF2γ polynucleotide comprises at least one oligonucleotide probe selected from the group comprising SEQ ID NO: 88 or which preferentially hybridizes to the same nucleotide sequence as is preferentially hybridized by SEQ ID NO: 88 and further comprises at least one forward primer selected from the group comprising ID NO: 97 or which preferentially hybridizes to the same nucleotide sequence as is preferentially hybridized by SEQ ID NO: 97 and/or at least one reverse primer selected from the group comprising SEQ ID NO: 98 or which preferentially hybridizes to the same nucleotide sequence as is preferentially hybridized by SEQ ID NO: 98.

A diagnostic kit for detecting or identifying an *Aspergillus* eIF2γ polynucleotide comprises at least one oligonucleotide probe selected from the group comprising SEQ ID NOs: 2, 108, 109, 110, 111 or 125 or which preferentially hybridizes to the same nucleotide sequence as is preferentially hybridized by SEQ ID NOs: 2, 108, 109, 110, 111 or 125. The kit may further comprise at least one forward primer selected from the group comprising SEQ ID NOs: 3, 104, 105, 112, 113, 114, 115, 116, 117, 118, 119 or 120 or which preferentially hybridizes to the same nucleotide sequence as is preferentially hybridized by SEQ ID NOs: 3, 104, 105, 112, 113, 114, 115, 116, 117, 118, 119 or 120 and/or at least one reverse primer selected from the group comprising SEQ ID NOs: 4, 106, 107, 121, 122, 123 or 124 or which preferentially hybridizes to the same nucleotide sequence as is preferentially hybridized by SEQ ID NOs: 4, 106, 107, 121, 122, 123 or 124.

A kit for detecting or identifying a *Aspergillus fumigatus* eIF2γ polynucleotide comprises at least one oligonucleotide probe selected from the group comprising SEQ ID NO: 2, 111 or 125 or which preferentially hybridizes to the same nucleotide sequence as is preferentially hybridized by SEQ ID NO: 2, 111 or 125 and further comprises at least one forward primer selected from the group comprising SEQ ID NO: 3, 112, 113, 115, 117, 119, or 120 or which preferentially hybridizes to the same nucleotide sequence as is preferentially hybridized by SEQ ID NO: 3, 112, 113, 115, 117, 119, or 120 and/or at least one reverse primer selected from the group comprising SEQ ID NO: 4, 106, 121, 123, 124 or which preferentially hybridizes to the same nucleotide sequence as is preferentially hybridized by SEQ ID NO: 4, 106, 121, 123, 124.

A kit for detecting or identifying a *Aspergillus flavus* eIF2γ polynucleotide comprises at least one oligonucleotide probe selected from the group comprising SEQ ID NO: 110 or which preferentially hybridizes to the same nucleotide sequence as is preferentially hybridized by SEQ ID NO: 110 and further comprises at least one forward primer selected from the group comprising SEQ ID NO: 104 or 114 or which preferentially hybridizes to the same nucleotide sequence as is preferentially hybridized by SEQ ID NO: 104 or 114 and at least one reverse primer selected from the group comprising SEQ ID NO: 106 122, or 123 or which preferentially hybridizes to the same nucleotide sequence as is preferentially hybridized by SEQ ID NO: 106 122, or 123

A kit for detecting or identifying a *Aspergillus niger* eIF2γ polynucleotide comprises at least one oligonucleotide probe selected from the group comprising SEQ ID NO: 108 or which preferentially hybridizes to the same nucleotide sequence as is preferentially hybridized by SEQ ID NO: 108 and further comprises at least one forward primer selected from the group comprising SEQ ID NO: 104, 114, 116 or which preferentially hybridizes to the same nucleotide sequence as is preferentially hybridized by SEQ ID NO: 104, 114, 116 and at least one reverse primer selected from the group comprising SEQ ID NO: 107, 122, 123 or which preferentially hybridizes to the same nucleotide sequence as is preferentially hybridized by SEQ ID NO: 107, 122, 123.

A kit for detecting or identifying a *Aspergillus terreus* eIF2γ polynucleotide comprises at least one oligonucleotide probe selected from the group comprising SEQ ID NO: 109 or which preferentially hybridizes to the same nucleotide sequence as is preferentially hybridized by SEQ ID NO: 109 and further comprises at least one forward primer selected from the group comprising SEQ ID NO: 105, 115, 118 or which preferentially hybridizes to the same nucleotide sequence as is preferentially hybridized by SEQ ID NO: 105, 115, 118 and at least one reverse primer selected from the group comprising SEQ ID NO: 107, 122 or 123 or which preferentially hybridizes to the same nucleotide sequence as is preferentially hybridized by SEQ ID NO: 107, 122 or 123.

The identified sequences are suitable not only for in vitro DNA/RNA amplification based detection systems but also for signal amplification based detection systems. Furthermore, the sequences of the invention identified as suitable targets provide the advantages of having significant intragenic sequence heterogeneity in some regions, which is advantageous and enables aspects of the invention to be directed towards group or species-specific targets, and also having significant sequence homogeneity in some regions, which enables aspects of the invention to be directed towards genus-specific yeast and fungal primers and probes for use in direct nucleic acid detection technologies, signal amplification nucleic acid detection technologies, and nucleic acid in vitro amplification technologies for yeast and fungal diagnostics. The eIF2 γ sequences allow for multi-test capability and automation in diagnostic assays.

One of the advantages of the sequences of the present invention is that the intragenic eIF2 γ nucleotide sequence diversity between closely related yeast and fungal species enables specific primers and probes for use in diagnostics assays for the detection of yeast and fungi to be designed. The eIF2 γ nucleotide sequences, both DNA and RNA can be used with direct detection, signal amplification detection and in vitro amplification technologies in diagnostics assays. The eIF2 γ sequences allow for multi-test capability and automation in diagnostic assays.

The kit may further comprise at least one primer for amplification of at least a portion of the eIF2 γ gene. Suitably the kit comprises a forward and a reverse primer for a portion of the eIF2 γ gene.

The portion of the eIF2 γ gene may be equivalent to a portion of the region of the gene from base pair position 718 to base pair position 1040 of the eIF2 γ gene in *C. albicans*. Particularly preferred are kits comprising a probe for a portion of the eIF2 γ *C. albicans* gene and/or a probe for a portion of the region of the gene equivalent to base pair position 718 to base pair position 1040 of the eIF2 γ gene in *C. albicans*. Sequences equivalent to base pair position 718 to base pair position 1040 can be found in other organisms, but not necessarily in the same position. The portion of the eIF2 γ gene may be equivalent to a portion of the region of the gene from base pair position 121 to base pair position 374 in *Aspergillus fumigatus*. Particularly preferred, are kits comprising a probe for a portion of the eIF2 γ *A. fumigatus* gene and/or a probe for a portion of the region of the gene equivalent to base pair position 121 to base pair position 374 in *Aspergillus fumigatus*. Sequences equivalent to base pair position 121 to base pair position 374 can be found in other organisms, but not necessarily in the same position. The kit may also comprise additional primers or probes. The primer may have a sequence selected from the group SEQ ID NO 3 through to SEQ ID NO 6 or a sequence substantially homologous to or substantially complementary to those sequences, which can also act as a primer for the eIF2 γ gene.

The kit may comprise at least one forward in vitro amplification primer and at least one reverse in vitro amplification primer, the forward amplification primer having a sequence selected from the group consisting of SEQ ID NO 3 or SEQ ID NO 5. or a sequence being substantially homologous or complementary thereto which can also act as a forward amplification primer for the eIF2 γ gene, and the reverse amplification primer having a sequence selected from the group consisting of SEQ ID NO 4 or SEQ ID NO 6 or a sequence being substantially homologous or complementary thereto which can also act as a reverse amplification primer for the eIF2 γ gene. The diagnostic kit may be based on direct nucleic acid detection technologies, signal amplification nucleic acid detection technologies, and nucleic acid in vitro amplification technologies is selected from one or more of Polymerase Chain Reaction (PCR), Ligase Chain Reaction (LCR), Nucleic Acids Sequence Based Amplification (NASBA), Strand Displacement Amplification (SDA), Transcription Mediated Amplification (TMA), Branched DNA technology (bDNA) and Rolling Circle Amplification Technology (RCAT)), or other in vitro enzymatic amplification technologies.

The invention also provides a nucleic acid molecule selected from the group consisting of SEQ ID NO. 1 to SEQ ID NO. 135, preferably SEQ ID NO. 1 through to 74 and SEQ ID NO. 84 through to 135, and sequences substantially homologous thereto, or substantially complementary to a portion thereof and having a function in diagnostics based on the eIF2 γ gene. The nucleic acid molecule may comprise an oligonucleotide having a sequence substantially homologous to or substantially complementary to a portion of a nucleic acid molecule of SEQ ID NO. 1 to SEQ ID NO. 135, preferably SEQ ID NO. 1 through to 74 and SEQ ID NO. 84 through to 135. The invention also provides a method of detecting a target organism in a test sample comprising the steps of:

(i) mixing the test sample with at least one oligonucleotide probe as defined above under appropriate conditions; and
(ii) hybridizing under high stringency conditions any nucleic acid that may be present in the test sample with the oligonucleotide to form a probe:target duplex; and
(iii) determining whether a probe:target duplex is present; the presence of the duplex positively identifying the presence of the target organism in the test sample.

The nucleic acid molecule and kits of the present invention may be used in a diagnostic assay to detect the presence of one or more yeast and/or fungal species, to measure yeast and/or fungal titres in a patient or in a method of assessing the efficacy of a treatment regime designed to reduce yeast and/or fungal titre in a patient or to measure yeast and/or fungal contamination in an environment. The environment may be a hospital, or it may be a food sample, an environmental sample e.g. water, an industrial sample such as an in-process sample or an end product requiring bioburden or quality assessment.

The kits and the nucleic acid molecule of the invention may be used in the identification and/or characterization of one or more disruptive agents that can be used to disrupt the eIF2 γ gene function. The disruptive agent may be selected from the group consisting of antisense RNA, PNA, and siRNA.

In some embodiments of the invention, a nucleic acid molecule comprising a species-specific probe can be used to discriminate between species of the same genus.

The oligonucleotides of the invention may be provided in a composition for detecting the nucleic acids of yeast and fungal target organisms. Such a composition may also comprise buffers, enzymes, detergents, salts and so on, as appropriate to the intended use of the compositions. It is also envisioned that the compositions, kits and methods of the invention, while described herein as comprising at least one synthetic oligonucleotide, may also comprise natural oligonucleotides with substantially the same sequences as the synthetic nucleotide fragments in place of, or alongside synthetic oligonucleotides.

The invention also provides for an in vitro amplification diagnostic kit for a target yeast and/or fungal organism comprising at least one forward in vitro amplification primer and at least one reverse in vitro amplification primer, the forward amplification primer being selected from the group consisting of one or more of a sequence being substantially homologous or complementary thereto which can also act as a forward amplification primer, and the reverse amplification primer being selected from the group consisting of one or more of or a sequence being substantially homologous or complementary thereto which can also act as a reverse amplification primer.

The invention also provides for a diagnostic kit for detecting the presence of candidate yeast and/or fungal species, comprising one or more DNA probes comprising a sequence substantially complementary to, or substantially homologous to the sequence of the eIF2 γ gene of the candidate yeast and/or fungal species. The present invention also provides for one or more synthetic oligonucleotides having a nucleotide sequence substantially homologous to or substantially complementary to one or more of the group consisting of the eIF2 γ gene or mRNA transcript thereof, the yeast and or fungal eIF2 γ gene or mRNA transcript thereof, the yeast eIF2 γ gene or mRNA transcript thereof, one or more of SEQ ID NO 1-SEQ ID NO 135, preferably SEQ ID NO. 1 through to 74 and SEQ ID NO. 84 through to 135.

The nucleotide may comprise DNA. The nucleotide may comprise RNA. The nucleotide may comprise a mixture of DNA, RNA and PNA. The nucleotide may comprise synthetic nucleotides. The sequences of the invention (and the sequences relating to the methods, kits compositions and assays of the invention) may be selected to be substantially homologous to a portion of the coding region of the eIF2 γ gene. The gene may be a gene from a target yeast or fungal organism. The sequences of the invention are preferably sufficient so as to be able form a probe:target duplex to the portion of the sequence.

The invention also provides for a diagnostic kit for a target yeast or fungal organism comprising an oligonucleotide probe substantially homologous to or substantially complementary to an oligonucleotide of the invention (which may be synthetic). It will be appreciated that sequences suitable for use as in vitro amplification primers may also be suitable for use as oligonucleotide probes: while it is preferable that amplification primers may have a complementary portion of between about 15 nucleotides and about 30 nucleotides (more preferably about 15-about 23, most preferably about 20 to about 23), oligonucleotide probes of the invention may be any suitable length. The skilled person will appreciate that different hybridization and or annealing conditions will be required depending on the length, nature & structure (eg. Hybridization probe pairs for LightCycler, Taqman 5' exonuclease probes, hairpin loop structures etc. and sequence of the oligonucleotide probe selected.

Kits and assays of the invention may also be provided wherein the oligonucleotide probe is immobilized on a surface. Such a surface may be a bead, a membrane, a column, dipstick, a nanoparticle, the interior surface of a reaction chamber such as the well of a diagnostic plate or inside of a reaction tube, capillary or vessel or the like.

The target yeast or fungal organism may be selected from the group consisting of *C. albicans, C. glabrata, C. krusei, C. parapsilosis, C. tropicalis, C. dubliniensis, C. guilliermondii, C. norvegiensis, C. famata, C. haemuloni, C. kefyr, C. utilis, C. viswanathii, C. lusitaniae* and *C. cifferii, A. fumigatus, N. fischeri, A. clavatus, A. niger, A. terreus, A. flavus, A. versicolor* and *A. nidulans*.

The target yeast organisms may be a *Candida* species for the given set of primers already experimentally demonstrated, and more preferably, selected from the group consisting of *C. albicans, C. glabrata, C. krusei, C. parapsilosis, C. dubliniensis* and *C. tropicalis, C. guilliermondii, C. norvegiensis, C. famata, C. haemuloni, C. kefyr, C. utilis, C. viswanathii, C. lusitaniae* and *C. cifferii*.

Under these circumstances, the amplification primers and oligonucleotide probes of the invention may be designed to a gene specific or genus specific region so as to be able to identify one or more, or most, or substantially all of the desired organisms of the target yeast organism grouping.

The target fungal organisms may be an *Aspergillus* species for given set of primers already experimentally demonstrated, and more preferably, selected from the group consisting of *A. fumigatus, N. fischeri, A. clavatus, A. niger, A. terreus, A. flavus, A. versicolor* and *A. nidulans*.

The test sample may comprise cells of the target yeast and/or fungal organism. The method may also comprise a step for releasing nucleic acid from any cells of the target yeast or fungal organism that may be present in said test sample. Ideally, the test sample is a lysate of an obtained sample from a patient (such as a swab, or blood, urine, saliva, a bronchial lavage dental specimen, skin specimen, scalp specimen, transplant organ biopsy, stool, mucus, or discharge sample). The test samples may be a food sample, a water sample an environmental sample, an end product, end product or in-process industrial sample.

The invention also provides for the use of any one of SEQ ID NO. 1 to SEQ ID NO. 135, preferably SEQ ID NO. 1 through to 74 and SEQ ID NO. 84 through to 135, in a diagnostic assay for the presence of one or more yeast or fungal species. The species may be selected from the group consisting of *C. albicans, C. glabrata, C. krusei, C. parapsilosis, C. tropicalis, C. dubliniensis, C. guilliermondii, C. norvegiensis, C. famata, C. haemuloni, C. kefyr, C. utilis, C. viswanathii, C. lusitaniae, C. cifferii, A. fumigatus, N. fischeri, A. clavatus, A. niger, A. terreus, A. flavus, A. versicolor* and *A. nidulans*.

The invention also provides for kits for use in theranostics, food safety diagnostics, industrial microbiology diagnostics, environmental monitoring, veterinary diagnostics, bio-terrorism diagnostics comprising one or more of the synthetic oligonucleotides of the invention. The kits may also comprise one or more articles selected from the group consisting of appropriate sample collecting instruments, reagent containers, buffers, labelling moieties, solutions, detergents and supplementary solutions. The invention also provides for use of the sequences, compositions, nucleotide fragments, assays, and kits of the invention in clinical diagnostics, theranostics, Food safety diagnostics, Industrial microbiology diagnostics, Environmental monitoring, Veterinary diagnostics, Bio-terrorism diagnostics.

The nucleic acid molecules, composition, kits or methods may be used in a diagnostic nucleic acid based assay for the detection of yeast and/or fungal species.

The nucleic acid molecules, composition, kits or methods may be used in a diagnostic assay to measure yeast and/or fungal titres in a patient. The titres may be measured in vitro.

The nucleic acid molecules, composition, kits or methods may be used in a method of assessing the efficacy of a treatment regime designed to reduce yeast and/or fungal titre in a patient comprising assessing the yeast and/or fungal titre in the patient (by in vivo methods or in vitro methods) at one or more key stages of the treatment regime. Suitable key stages may include before treatment, during treatment and after treatment. The treatment regime may comprise an antifungal agent, such as a pharmaceutical drug.

The nucleic acid molecules, composition, kits or methods may be used in a diagnostic assay to measure potential yeast and/or fungal contamination, for example, in a hospital.

The nucleic acid molecules, composition, kits or methods may be used in the identification and/or characterization of one or more disruptive agents that can be used to disrupt the eIF2 γ gene function. Suitable disruptive agents may be selected from the group consisting of antisense RNA, PNA, siRNA.

The current invention will now be described with reference to the following figures. It is to be understood that the following detailed description and accompanying figures, are exemplary and explanatory only and are intended to provide a further explanation of the present invention, as claimed and not to limit the scope of the invention in any way.

BRIEF DESCRIPTION OF THE FIGURES

FIG. 1: (SEQ ID NO: 99) Primers binding sites (grey highlights) and probe (bold text) in eIF2γ of *Candida albicans* (XM_715569.1). The amplified region of interest is underlined. (Position of the region of interest: 718-1040).

FIG. 2: (SEQ ID NO: 77) Primers binding sites (grey highlights) and probe (bold text) in eIF2γ of *Aspergillus fumigatus* (XM_746974.2). The amplified region of interest is underlined. (Position of the region of interest: 121-374).

FIG. 5: (SEQ ID NO: 99) Primers binding sites (grey highlights) and probe (bold text) in eIF2γ of *Candida albicans* (XM_715569.1). The amplified region of interest is underlined. (Position of the region of interest: 664-1040).

FIG. 6: (SEQ ID NO: 100) Primers binding sites (grey highlights) and probe (bold text) in eIF2γ of *Candida glabrata* (XM_44 7610.1). The amplified region of interest is underlined. (Position of the region of interest: 872-972).

FIG. 7: (SEQ ID NO: 101) Primers binding sites (grey highlights) and probe (bold text) in eIF2γ of *Candida parapsilosis* (CBS 604 generated sequence). The amplified region of interest is underlined. (Position of the region of interest: 151-274).

FIG. 8: (SEQ ID NO: 102) Primers binding sites (grey highlights) and probe (bold text) in eIF2γ of *Candida tropicalis* (CBS 94 generated sequence). The amplified region of interest is underlined. (Position of the region of interest: 140-270).

FIG. 9: (SEQ ID NO: 103) Primers binding sites (grey highlights) and probe (bold text) in 5 eIF2γ of *Candida krusei* (CBS 573 generated sequence). The amplified region of interest is underlined. (Position of the region of interest: 115-224).

(FIG. 10A) The 14 *C. albicans* strains tested were detected. (FIG. 10B) No cross-reaction was seen with DNA from 19 the other *Candida* species. Signal obtained only from (+) control. (FIG. 10C) Sensitivity of the assay was tested using a various inputs of template DNA from *C. albicans*. The LOD of the assay was found to be between 1-5 cell equivalents.

(FIG. 11A) The 10 *C. glabrata* strains tested were detected. (FIG. 11B) No cross-reaction was seen with DNA from 19 the other *Candida* species or with *Aspergillus fumigatus* or *Saccharomyces cerevisiae*. Signal obtained only from (+) control. (FIG. 11C) The LOD of the assay was found to be ~2 cell equivalents.

(FIG. 12A) The 12 *C. parapsilosis* strains tested were detected. (FIG. 12B) No cross-reaction was seen with DNA from the other 19 *Candida* species or with *Aspergillus fumigatus* or *Saccharomyces cerevisiae*. Signal obtained only from (+) control. (FIG. 12C) The LOD of the assay was found to be ~10 cell equivalents.

(FIG. 13A) The 12 *C. tropicalis* strains tested were detected. (FIG. 13B) No cross-reaction was seen with DNA from the other 19 *Candida* species or with *Aspergillus fumigatus* or *Saccharomyces cerevisiae*. Signal obtained only from (+) control. (FIG. 13C) The LOD of the assay was found to be ~20 cell equivalents.

FIGS. 14A-14C FIG. 14: Amplification plot from Real-time PCR assay for *C. krusei* based on the eIF2 gene with TaqMan probe KrusA. Specificity of the assay was tested using a panel of DNA from 9 *C. krusei* strains, 19 other *Candida* species, *Aspergillus fumigatus* and *Saccharomyces cerevisiae*. (FIG. 14A) The 9 *C. krusei* strains tested were detected. (FIG. 14B) No cross-reaction was seen with DNA from the other 19 *Candida* species or with *Aspergillus fumigatus* or *Saccharomyces cerevisiae*. Signal obtained only from (+) control. (FIG. 14C) The LOD of the assay was found to be ~2 cell equivalents.

FIG. 15: (SEQ ID NO: 50) Primers binding sites (grey highlights) and probe (bold text) in eIF2γ of *Aspergillus fumigatus* (7273 generated sequence). The amplified region of interest is underlined. (corresponding to base pair positions 164-261 of published sequence).

FIG. 16: (SEQ ID NO: 147) Primers binding sites (grey highlights) and probe (bold text) in eIF2 γ of *Aspergillus flavus* (117.62 generated sequence). The amplified region of interest is underlined. (corresponding to base pair positions 155-252 of published sequence).

FIG. 17: (SEQ ID NO: 58) Primers binding sites (grey highlights) and probe (bold text) in eIF2γ of *Aspergillus niger* (6727 generated sequence). The amplified region of interest is underlined (corresponding to base pair positions 92-189 of published sequence).

FIG. 18: (SEQ ID NO: 64) Primers binding sites (grey highlights) and probe (bold text) in 15 eIF2γ of *Aspergillus terreus* (5677 generated sequence). The amplified region of interest is underlined. (corresponding to base pair positions 149-246 of published sequence).

DETAILED DESCRIPTION OF THE INVENTION

Materials and Methods

Cell Culture

Figure 3:
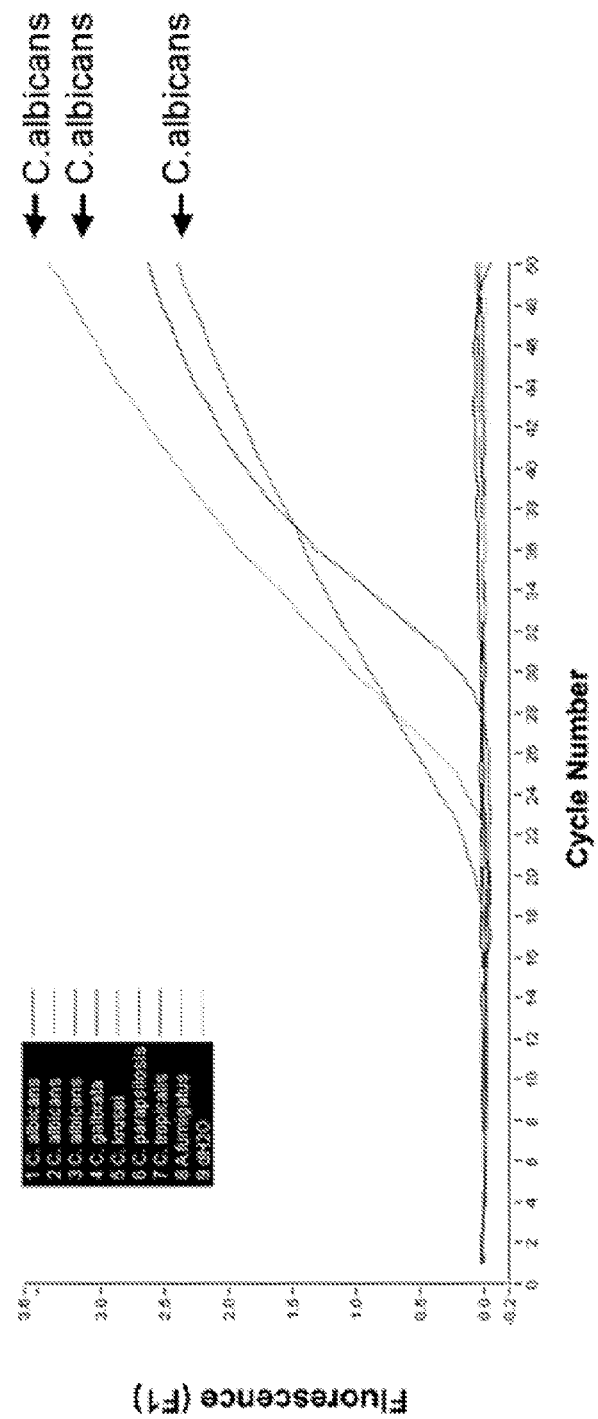
FIG. 3: Amplification plot from Real-time PCR assay for *C. albicans* based on the eIF2γ gene with TaqMan probe P1-CaneIF2. Specificity of the assay was tested using a panel of DNA from 4 other *Candida* species and *Aspergillus fumigatus*. The 3 *C. albicans* strains tested were detected and no cross-reaction was seen with DNA from the other *Candida* species and *A. fumigatus*.

A collection of geographically distinct strains of clinically relevant *Candida* species was obtained from a number of culture collections. *Candida* species were cultured in Sabouraud broth (4% wt/vol glucose, 1% wt/vol peptone, 1.5% agar) for 48 hours at 37° C. in a shaking incubator. *Aspergillus* species (*A. fumigatus, A. flavus, A. niger* and *A. terruous* and other closely related species) were cultured in Sabouraud broth (4% wt/vol glucose, 1% wt/vol peptone, 1.5% agar) or agar for 3-4 days at 25° C.

DNA Extraction

Cells from *Candida* and *Aspergillus* spp. were pretreated with lyticase or zymolase enzymes prior to DNA isolation. DNA was isolated from *Candida* and *Apergillus* spp. using the MagNA Pure System (Roche Molecular Systems) in combination with the MagNA pure Yeast and Bacterial isolation kit III or with the Qiagen Plant kit-according to manufacturers instructions.

Sequencing of eIF2 γ Gene of *Candida* and *Aspergillus* Species

The publicly available sequences of the eIF2 genes of *Candida* or *Aspergillus* species were acquired from the NCBI database and aligned using Clustal W.

The PCR primer set CaneIF2-F/CaneIF2-R was designed to amplify the eIF2γ gene region in *Candida* spp. equivalent to nucleotide position 718 to nucleotide position 1040 in *C. albicans* (XM_715569.1). (Table 1, FIG. 1). The PCR primer set AspeIF2-F/AspeIF2-R was designed to amplify a region of the eIF2γ gene in *Aspergillus* species equivalent to nucleotide position 121 to nucleotide position 374 in *A. fumigatus*(XM_746974.2). (Table 1). The eIF2 gene regions were amplified in a range of *Candida* and *Aspergillus* spp. by conventional PCR on the iCycler BioRad PCR machine or the PTC200 Peltier thermocycler (MJ Research) using the reagents outlined in Table 2 and the thermocycling conditions described in Table 3. In order to generate sequence information, a total of 72 strains representing 20 *Candida* species were tested for amplification with this primer set by conventional PCR on the iCycler BioRad PCR machine. PCR products were generated for 15 *Candida* species. *C. albicans, C. glabrata, C. krusei, C. parapsilosis, C. tropicalis, C. dubliniensis, C. guilliermondii, C. norvegiensis, C. famata, C. haemuloni, C. kefyr, C. utilis, C. viswanathii, C. lusitaniae* and *C. cifferii*. and 7 *Aspergillus* species (*A. fumigatus, A. clavatus, A. niger, A. terreus, A. flavus, A.*

*versicolor, A. nidulans*) and *Neosartorya fischeri*). The PCR reaction products were purified with Roche High Pure PCR Product Purification kit or with the ExoSAP-IT kit (USB) according to the manufacturers' instructions and subsequently sequenced by Sequiserve using the forward amplification primer CaneIF2-F or AspeIF2-F.

DNA sequence information was generated for 15 *Candida* species. (*C. albicans, C. glabrata, C. krusei, C. parapsilosis, C. tropicalis, C. dubliniensis, C. guilliermondii, C. norvegiensis, C. famata, C. haemuloni, C. kefyr, C. utilis, C. viswanathii, C. lusitaniae* and *C. cifferii*, and 7 *Aspergillus* species (*A. fumigatus, A. clavatus, A. niger, A. terreus, A. flavus, A. versicolor, A. nidulans*) and *Neosartorya fischeri*.

TABLE 1

PCR primers designed to amplify the eIF2 γ gene regions in *Candida* and *Aspergillus* spp

| Primer Name | Primer Sequence |
| --- | --- |
| AspeIF2-F | CTTAAGTCTGCGATGAAGA |
| AspeIF2-R | GTAATGTTACGCTCCAACTC |
| CaneIF2-F | GCTGCCATTGAAATTATGAA |
| CaneIF2-R | GAACCACCTGCAACACC |

TABLE 2

PCR reagents used to amplify the eIF2 γ gene regions in *Candida* and *Aspergillus* spp.

| PCR Reaction Mix | SAMPLE x 1 |
| --- | --- |
| 10 x Buffer (100 mM Tris HCl, 15 mM MgCl₂, 500 mM KCl pH 8.3) | 5 µl |
| dNTP's Mix, Roche (10 mM dNTP) | 1 µl |
| Primer Forward CaneIF2-F or AspeIF2-F (10 µM) | 1 µl |
| Primer Reverse CaneIF2-R or AspeIF2-R (10 µM) | 1 µl |
| Polymerase TaqPol, Roche 1 U/µl | 1 µl |
| H20 Amgen/Accugene | 36-39 µl |
| DNA Template | 2-5 µl |
| TOTAL VOLUME | 50 µl |

TABLE 3

PCR thermocycling conditions used to amplify eIF2 γ gene regions in *C. albicans* and *A. fumigatus*.
PCR Thermal profile    Lid preheating was ON

| Step | Temp | Time | |
| --- | --- | --- | --- |
| 1 | 94° C. | 1 min | X 35 |
| 2 | 50° C., 51° C. | 1 min | |
| 3 | 72° C. | 1 min | |
| 4 | 72° C. | 7 min | |
| 5 | 8° C. | Hold | |

TABLE 4

TaqMan probes (with 5'-FAM and 3'-BHQ1) based on eIF2 γ gene for *C. albicans* and *A. fumigatus*.

| Probe Name | Probe Sequence |
| --- | --- |
| P1-CaneIF2 | CGATAATGCTCCGATCGTGCCTA |
| P1-AspeIF2 | CGCTCACACCTCTGTCGCCCGAA |

TABLE 5

Real-time PCR reagents

| Preparation of PCR Reaction Mix | SAMPLE X 1 |
| --- | --- |
| HybProb mix 10 x conc. (LightCycler ® FastStartDNA Master HybProbe Kit) | 2 µl |
| MgCl₂ stock solution (Final conc. in reaction is 3 mM) | 1.6 µl |
| Probe P1-CaneIF2 or P1-AspeIF2 | 2 µl |
| Primer Forward CaneIF2-F or AspeIF2-F | 1 µl |
| Primer Reverse CaneIF2-R or AspeIF2-R | 1 µl |
| H₂O PCR-grade | 10.4 µl |
| Template | 2 µl |
| TOTAL VOLUME | 20 µl |

TABLE 6

Real-time PCR thermocycling conditions
PCR Thermal profile

| Cycle | Step | Temp | Time | |
| --- | --- | --- | --- | --- |
| Activation | 1 | 95° C. | 10 min | X 50 |
| Amplification | 1 | 95° C. | 10 sec | |
| | 2 | 62 or 65° C. | 20 sec | |
| | 3 | 70° C. | 10 sec | |
| Cooling | 1 | 40° C. | Hold | |

The PCR was performed with LightCycler ® Roche

Results
Primer and Probe Design

The publicly available sequences for the eIF2γ gene in *Candida* spp. was aligned with the newly generated sequence information for the eIF2γ gene in *Candida* spp. and analyzed using bioinformatics tools. The publicly available sequence information for the eIF2γ gene in *Aspergillus* spp. was aligned with the newly generated sequence information for the eIF2γ gene in *Aspergillus* spp. and analyzed using bioinformatics tools. Species-specific probes were designed based on the compiled eIF2γ sequence information for *Candida albicans* and *Aspergillus fumigatus* (Table 4).

Real-Time PCR

FIGS. 1-2 show the relative positions of the PCR primers and TaqMan DNA probes for the amplification and detection of *C. albicans* and *A. fumigatus*. The specificity of the TaqMan probes for the identification of *C. albicans* and *A. fumigatus* was demonstrated in real-time PCR assays on the LightCycler using the reagents and thermocycling conditions outlined in Tables 5 and 6. For the *C. albicans* assay based on the eIF2γ gene, PCR primers CaneIF2-F/CaneIF2-R were combined with TaqMan probe, P 1-CaneIF2. The specificity of the assay for the detection of *C. albicans* was confirmed by including DNA from a range of closely related *Candida* species and *A. fumigatus* in the *C. albicans* real-time PCR assay. The assay detected three *C. albicans* strains tested but did not detect or cross-react with DNA from any other *Candida* species tested or with *A. fumigatus* DNA. FIG. 3 shows the *C. albicans* real-time PCR assay and the specificity of the assay for *C. albicans*.

Figure 4:
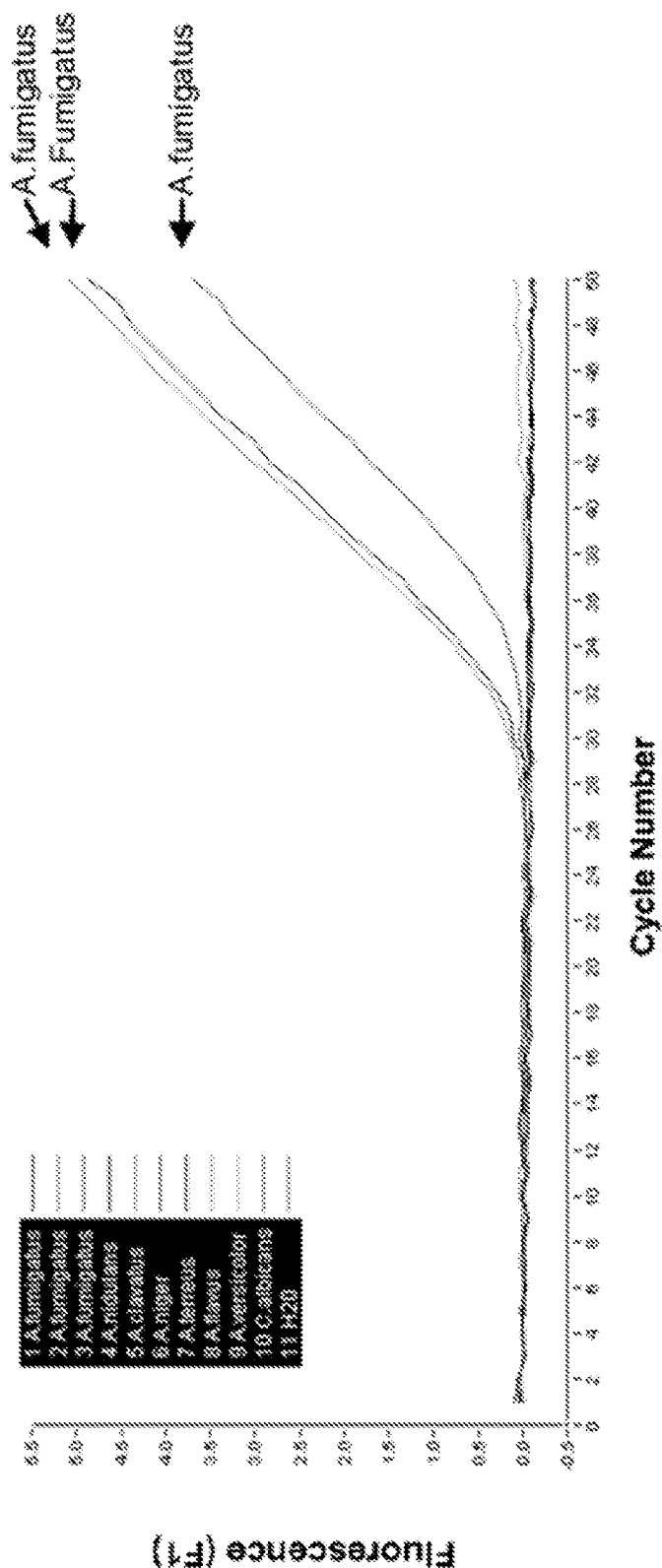
FIG. 4.: Amplification plot from Real-time PCR assay for *A. fumigatus* based on the eIF2γ gene with TaqMan probe P1-AspeIF2. Specificity of the assay was tested against a panel of DNA from 6 closely related *Aspergillus* species and *C. albicans*. The 3 *A. fumigatus* strains were detected and no cross-reaction was seen with DNA from the other *Aspergillus* spp and *C. albicans*.

For the *A. fumigatus* assay based on the eIF2γ gene PCR primers AspeIF2-F/AspeIF2-R were combined with TaqMan probe, P1-AspeIF2. The specificity of the assay for the detection of *A. fumigatus* was confirmed by including DNA from a range of closely related *Aspergillus* species and *C. albicans* in the *A. fumigatus* real-time PCR assay. The assay detected *A. fumigatus* but did not detect or cross-react with DNA from *C. albicans* or any other *Aspergillus* species tested. FIG. 4 shows the *A. fumigatus* real-time PCR assay and the specificity of the assay for *A. fumigatus*.

*Candida* spp

Primer and Probe Design

The publicly available sequences for the eIF2γ gene in *Candida* spp. were aligned with the newly generated sequence information for the eIF2γ gene in *Candida* spp. and analysed using bioinformatics tools. Species-specific probes were designed based on the compiled eIF2γ sequence information for *Candida albicans, Candida glabrata, Candida krusei, Candida tropicalis* and *Candida parapsilosis* (Table 7 and 8). FIGS. 5-9 show the relative positions of the PCR primers and TaqMan DNA probes for the amplification and detection of *Candida albicans, Candida glabrata, Candida krusei, Candida tropicalis* and *Candida parapsilosis*.

TABLE 7

Additional primer and probes designed and tested for use in *C. albicans* specific assay

| Primer Name | Primer Sequence 5'->3' |
|---|---|
| CEF1F | 5'-ATCTATCATTCAGTTTATTAGAG-3' |
| CEF2F | 5'-CATTCAGTTTATTAGAGGTAC-3' |
| CEFR2 | 5'-CAGTAAAGTCTCTCATTG-3' |
| Probe Name | Probe Sequence 5'->3' |
| ALEF1 | FAM-TGCCGATAATGCTCCGATC-BHQ1 |

TABLE 8

TaqMan probes (with 5'-FAM and 3'-BHQ1) based on eIF2γ gene for *C. albicans, C. glabrata, C. parapsilosis, C. tropicalis,* and *C. krusei.*

| Probe Name | Probe Sequence 5'->3' |
|---|---|
| ALEF2 | 6FAM-ATAATGCTCCGATCGTGCCTA-BHQ1 |
| GlabA | 6FAM-CAAGAGATTTCATGCTTTCTCCAC-BHQ1 |
| ParA | 6FAM-CGTAAACTCAATACCAGTTCCAGTC-BHQ1 |
| TropicA | 6FAM-TGTCAATTATATCCCAGTTCCATTGA-BHQ1 |
| KrusA | 6FAM-CATGTGTATGGTCAAGTCTATTCCT-BHQ1 |

TABLE 9

Real Time PCR primers based on eIF2 gene for *C. albicans, C. glabrata, C. parapsilosis, C. tropicalis,* and *C. krusei.*

| Primer Name | Primer Sequence 5'->3' |
|---|---|
| CEF3F | 5'-TCAGCCTTGGAACAC-3' |
| CEFR1 | 5'-TTGGCACAGGTATGTAG-3' |
| GlabF1 | 5'-TCgTgAAgACTATCCCTgT-3' |
| GlabR1 | 5'-ATCGATTTCAGCACCTGG-3' |
| ParaF1 | 5'-TATCgACgCCgTCAATC-3' |
| ParaR1 | 5'-ATCAACgTCAgCACCAg-3' |
| TropicF1 | 5'-ACATCGATGCCGTTAACC-3' |

TABLE 9-continued

Real Time PCR primers based on eIF2 gene for *C. albicans, C. glabrata, C. parapsilosis, C. tropicalis,* and *C. krusei.*

| Primer Name | Primer Sequence 5'->3' |
|---|---|
| TropicR1 | 5'-CAAGTCTTCGACATCGGA-3' |
| KrusF1 | 5'-CCCAATTTCTGCTCAGTTG-3' |
| KrusR1 | 5'-CACCAGGCTTATTAACATCG-3' |

Real Time PCR

The specificity of the TaqMan probes for the identification of *Candida albicans, Candida glabrata, Candida krusei, Candida tropicalis* and *Candida parapsilosis* was demonstrated in real-time PCR assays on the LightCycler using the thermocycling conditions outlined in Table 10 (a) & (b) (*C. albicans*).

TABLE 10

Initial amplification conditions for evaluation of *C. glabtrata, C. parapsilosis, C. krusei* and *C. tropicalis* assay performance.

| Amplification Protocol (a) PCR conditions: Mn2+ (Z05) | | | Amplification Protocol (b) PCR conditions: Mn2+ (Z05) | | |
|---|---|---|---|---|---|
| 50° C. | 2 min | UNG | 50° C. | 2 min | UNG |
| 95° C. | 1 min | | 95° C. | 1 min | |
| 95° C. | 10 sec | 45 cycles | 95° C. | 1 sec | 45 cycles |
| 60° C. | 30 sec | | 60° C. | 10 sec | |
| 40° C. | 2 min | 1 cycle | 40° C. | 2 min | 1 cycle |

Figure 10A:
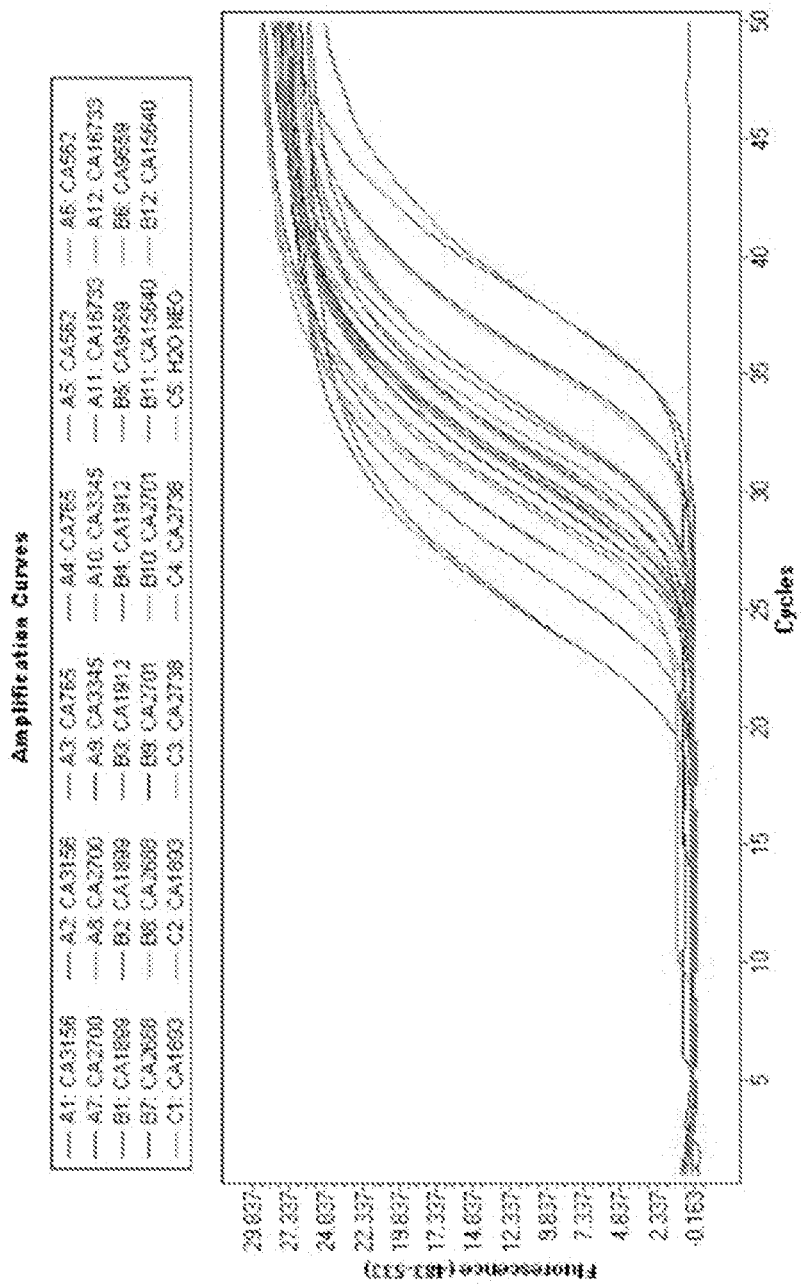
FIGS. 10A-10C: Amplification plot from Real-time PCR assay for *C. albicans* based on the eIF2 γ gene with TaqMan probe ALEF2. Specificity of the assay was tested using a panel of DNA from 14 *C. albicans* strains and 19 other *Candida* species.
Figure 10B:
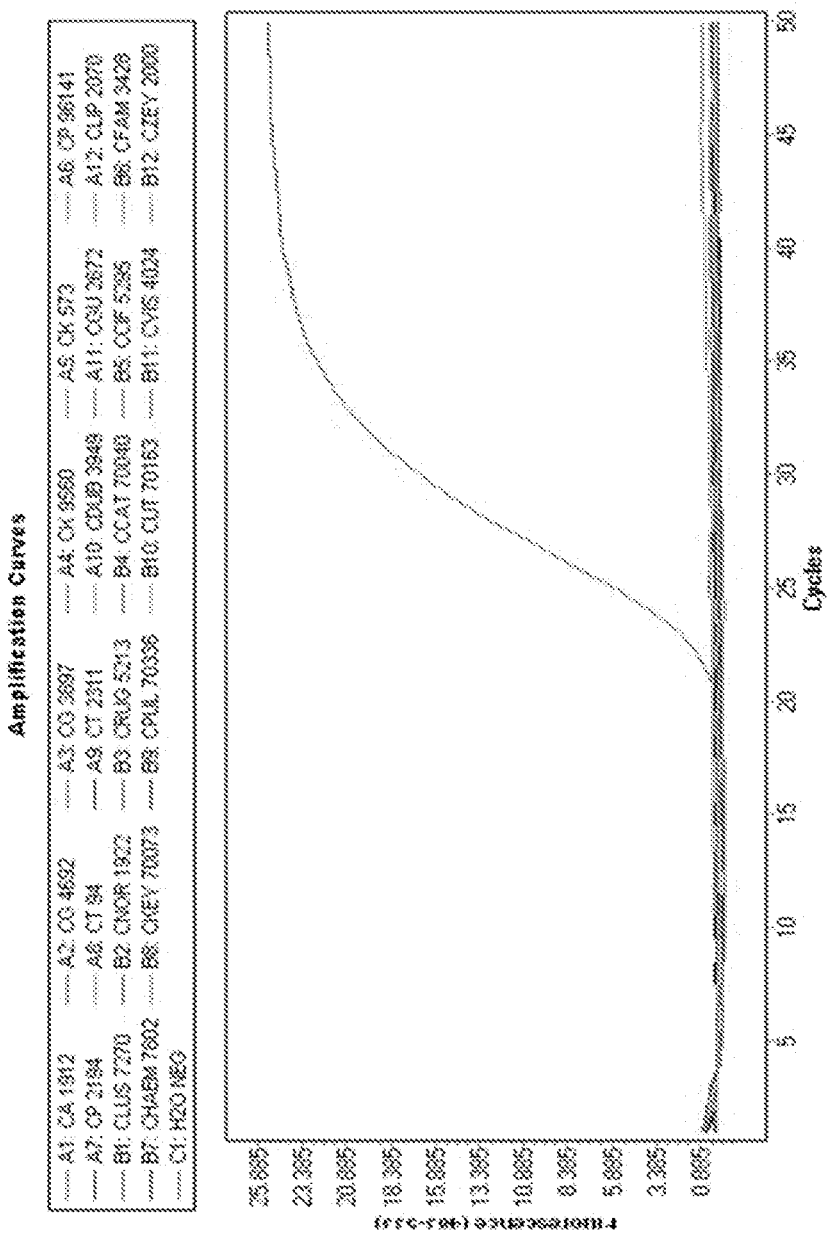
Figure 10C:
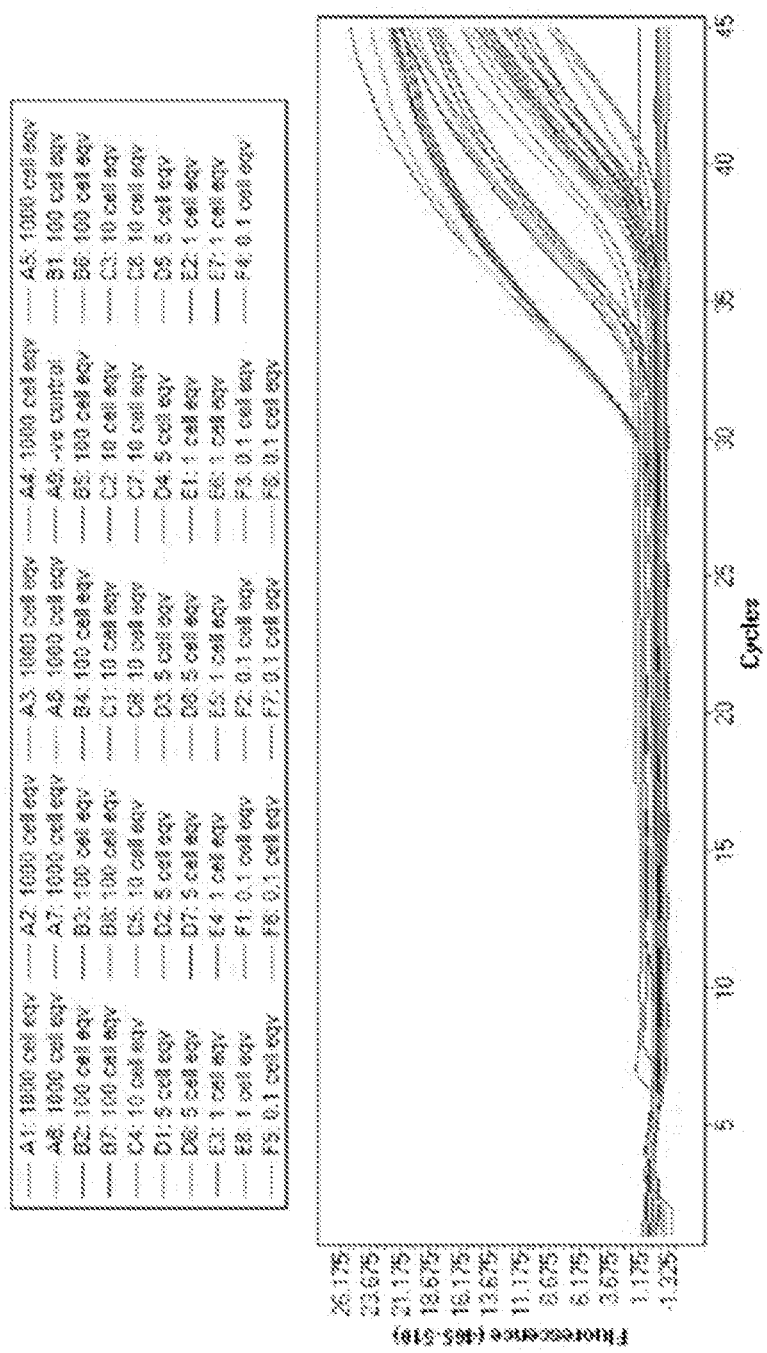

For the *C. albicans* assay based on the eIF2γ gene, following evaluation of the primers and probes listed in Table 7 and 8, PCR primers CEF3F/CEFR1 were combined with TaqMan probe, ALEF2. The specificity of the assay for the detection of *C. albicans* was confirmed by including DNA from a range of closely related *Candida* species in the *C. albicans* real-time PCR assay. The assay detected fourteen *C. albicans* strains tested but did not detect or cross-react with DNA from any other 19 *Candida* species tested. Sensitivity of the assay was tested using various inputs of template DNA from *C. albicans*. The LOD of the assay was found to be between 1-5 cell equivalents (FIG. 10).

Figure 11A:
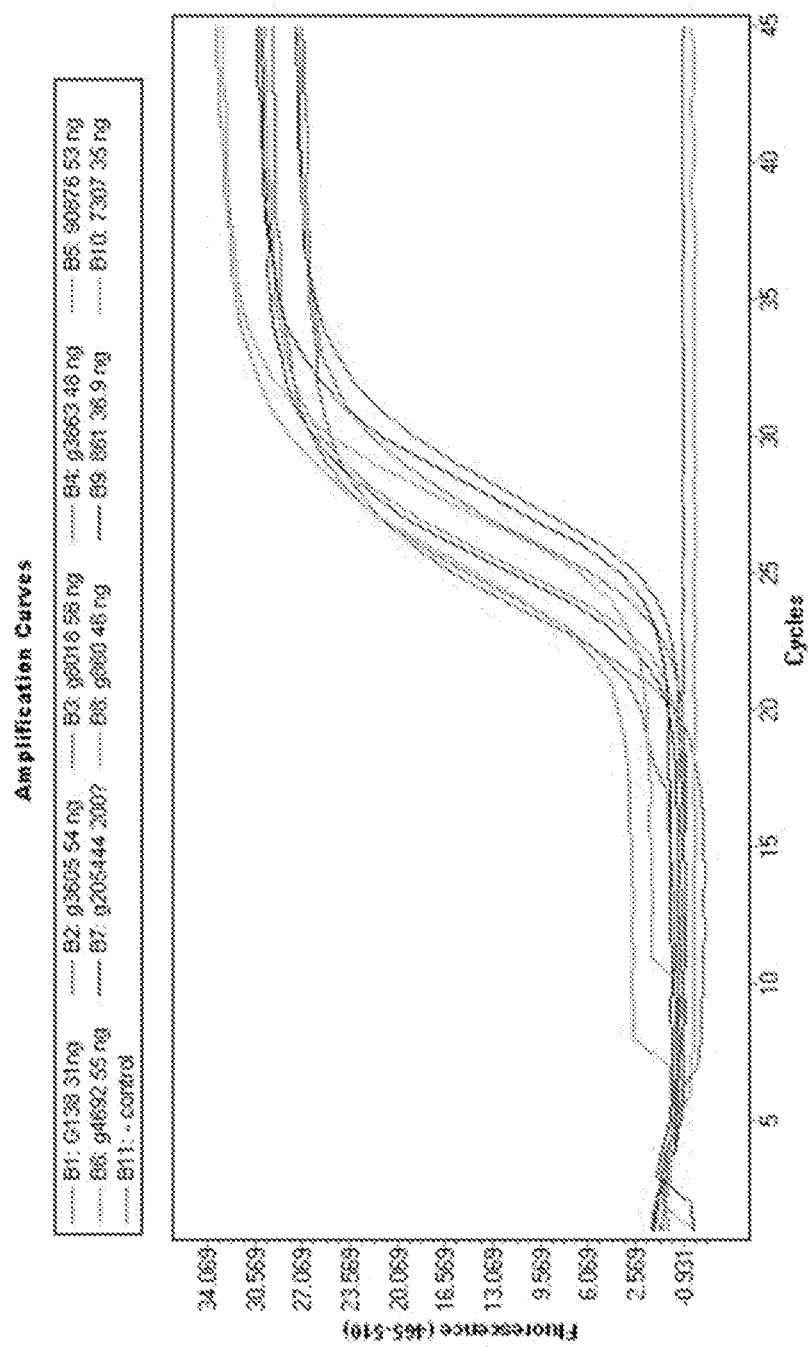
FIGS. 11A-11C: Amplification plot from Real-time PCR assay for *C. glabrata* based on the eIF2γ gene with TaqMan probe GlabA. Specificity of the assay was tested using a panel of DNA from 10 *C. glabrata* strains, 19 other *Candida* species, *Aspergillus fumigatus* and *Saccharomyces cerevi-* siae.
Figure 11B:
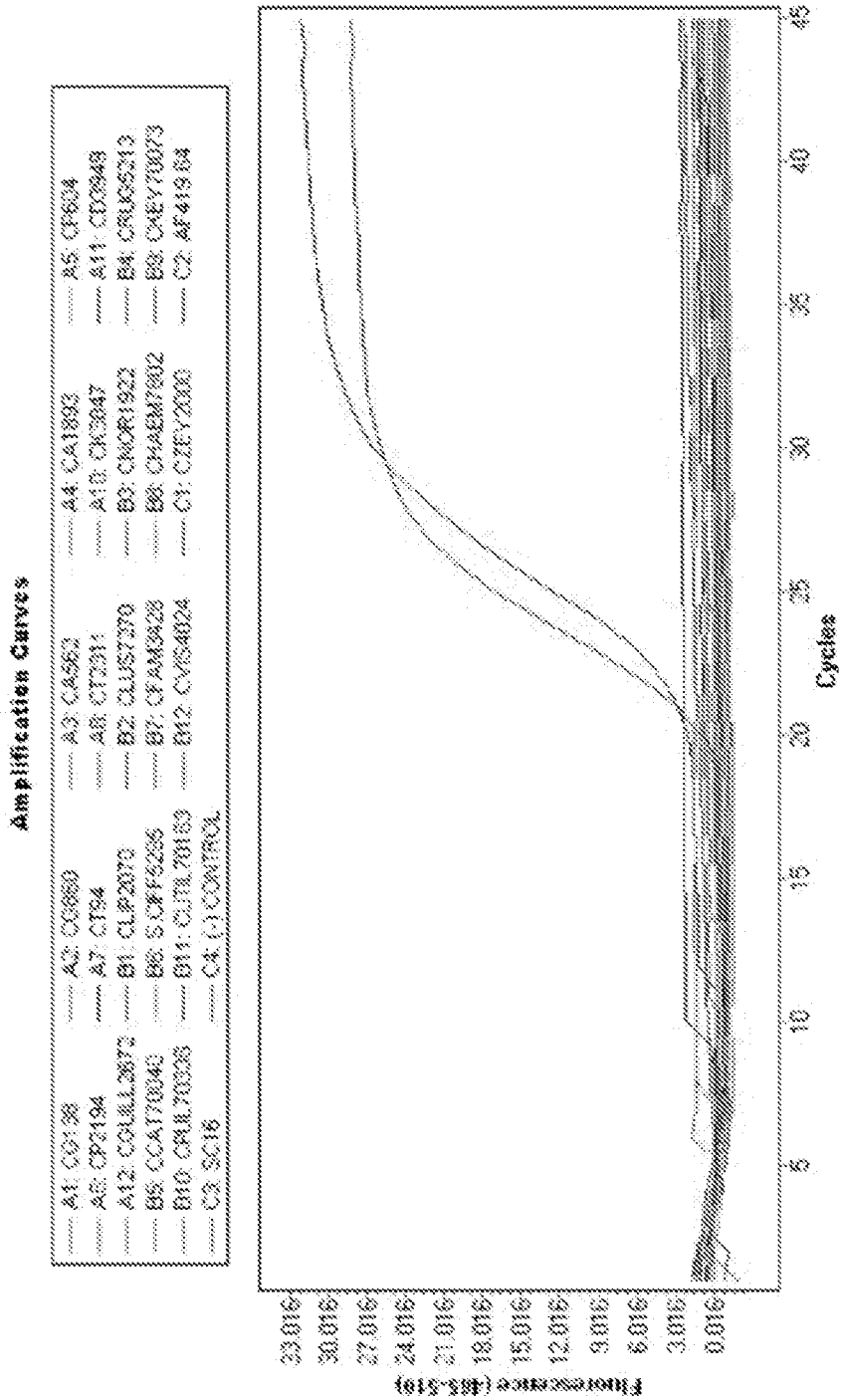
Figure 11C:
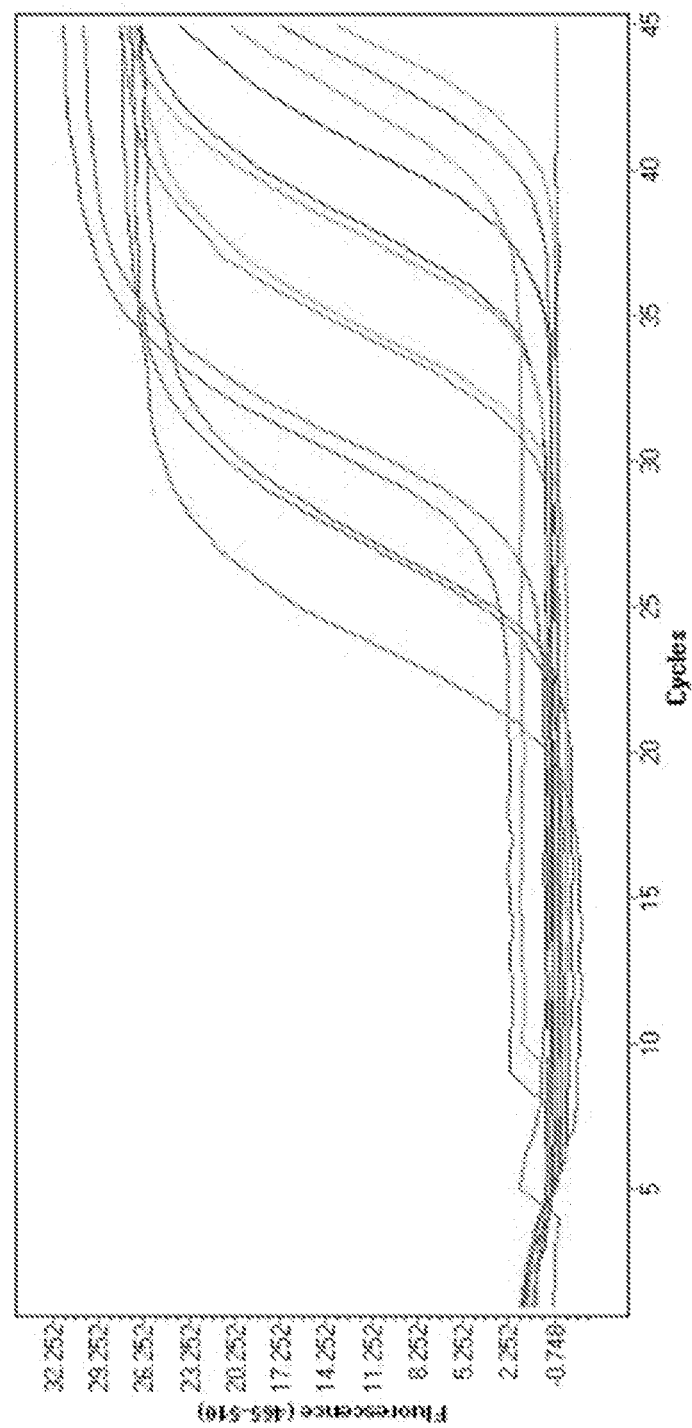

For the *C. glabrata* assay based on the eIF2γ gene, PCR primers GlabF1/GlabR1 were combined with TaqMan probe, GlabA. The specificity of the assay for the detection of *C. glabrata* was confirmed by including DNA from a range of closely related *Candida* species, *Saccharomyces cerevisiae* and *A. fumigatus* in the *C. glabrata* real-time PCR assay. The assay detected ten *C. glabrata* strains tested but did not detect or cross-react with DNA from any other 19 *Candida* species tested or with *S. cerevisiae* or *A. fumigatus* DNA. Initial sensitivity of the assay was tested using various inputs of template DNA from *C. glabrata*. The LOD of the assay was found to be ~2 cell equivalents (FIG. 11).

Figure 12A:
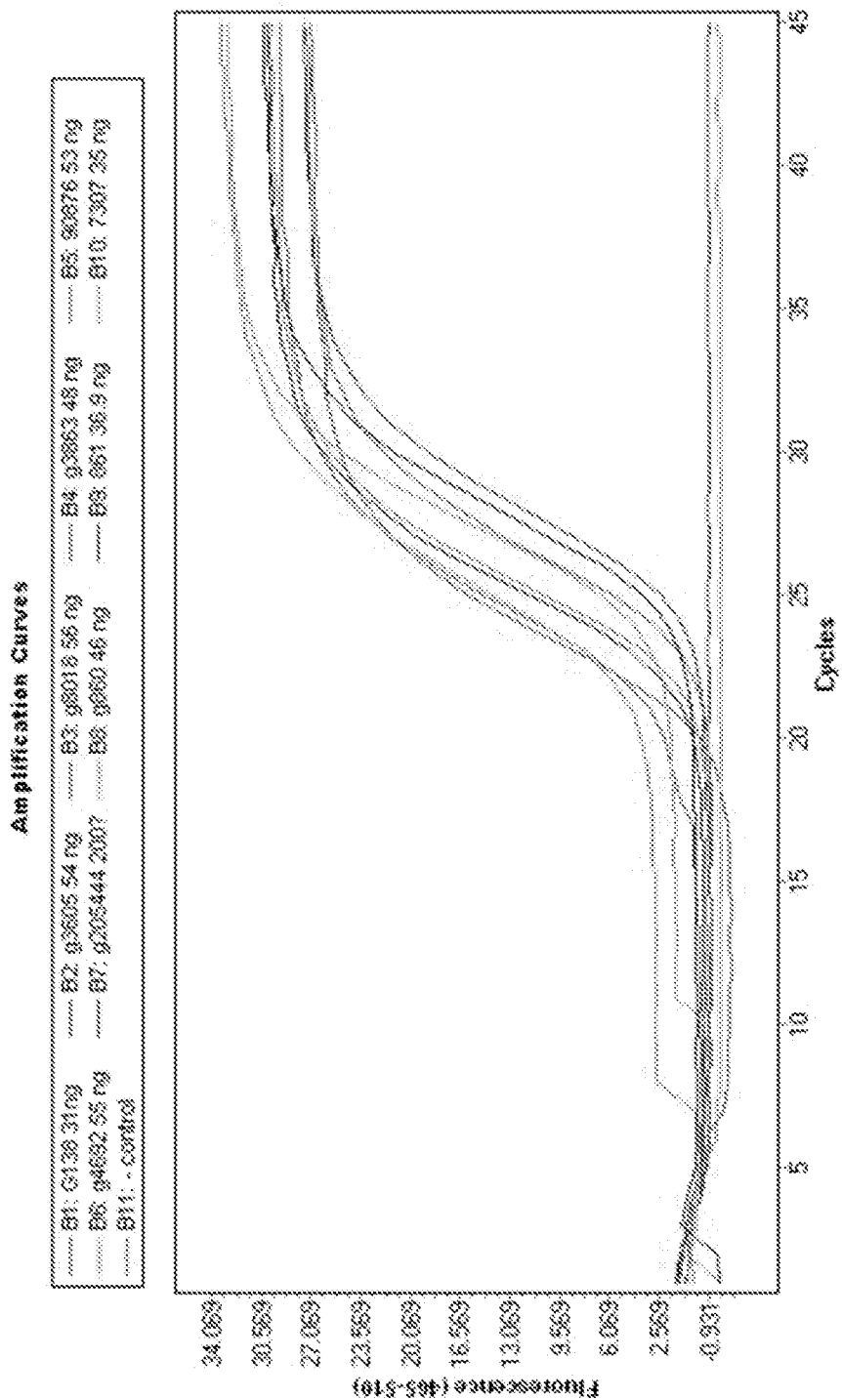
FIGS. 12A-12C: Amplification plot from Real-time PCR assay for *C. parapsilosis* based on the eIF2 γ gene with TaqMan probe ParA. Specificity of the assay was tested using a panel of DNA from 12 *C. parapsilosis* strains, 19 other *Candida* species, *Aspergillus fumigatus* and *Saccharomyces cerevisiae*.
Figure 12B:
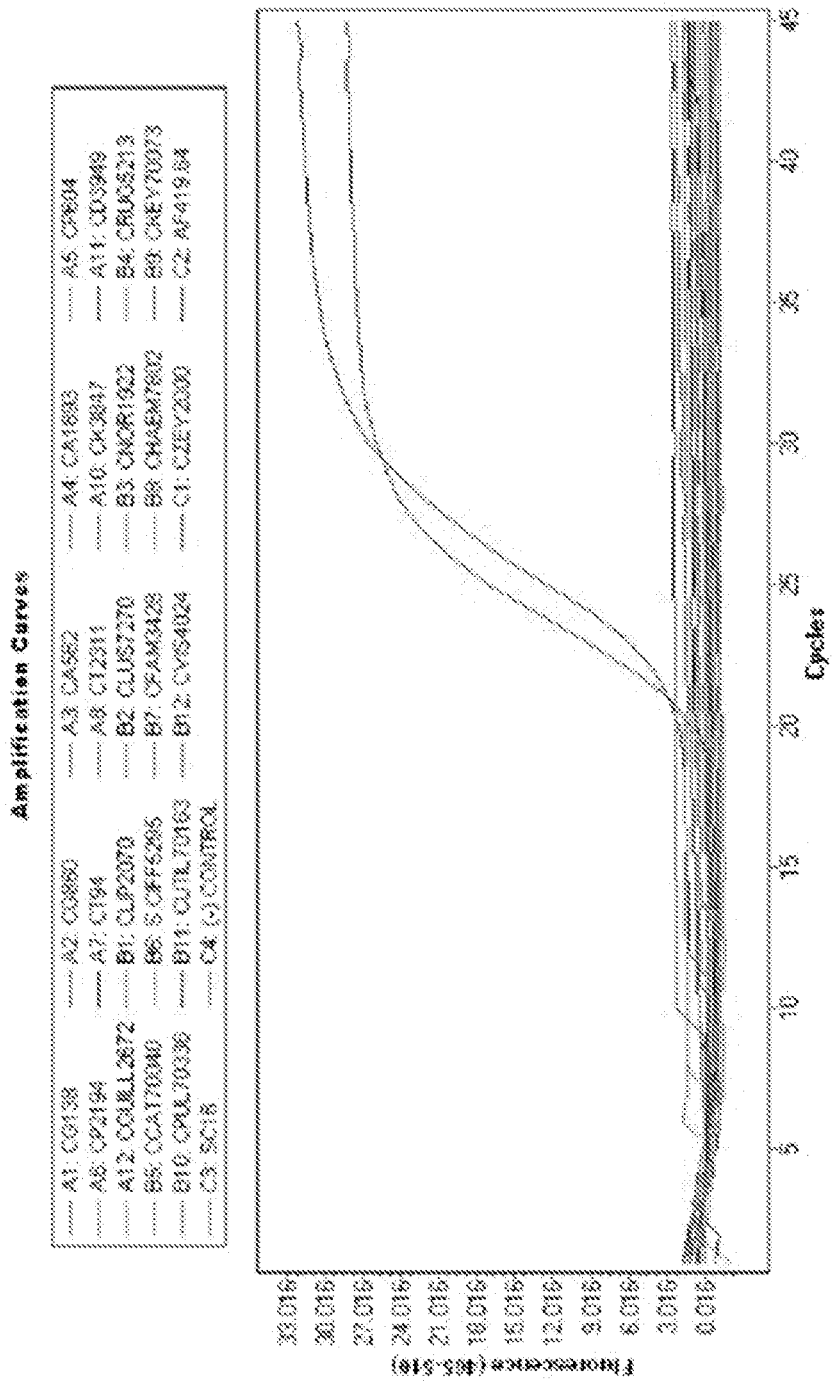
Figure 12C:
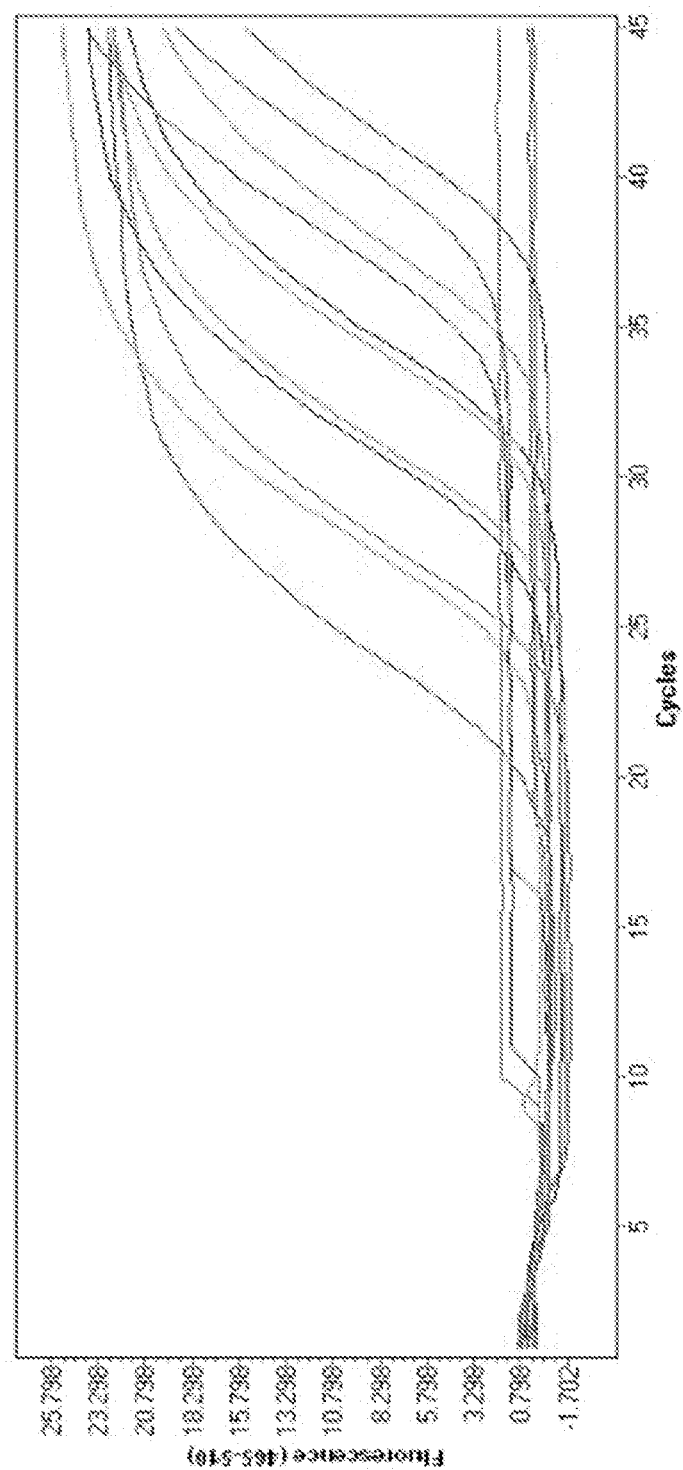

For the *C. parapsilosis* assay based on the eIF2γ gene, PCR primers ParaF1/ParaR1 were combined with TaqMan probe, ParA. The specificity of the assay for the detection of *C. parapsilosis* was confirmed by including DNA from a range of closely related *Candida* species, *Saccharomyces cerevisiae* and *A. fumigatus* in the *C. parapsilosis* real-time PCR assay. The assay detected twelve *C. parapsilosis* strains tested but did not detect or cross-react with DNA from any other 19 *Candida* species tested or with *S. cerevisiae* or *A. fumigatus* DNA. Initial sensitivity of the assay was tested using various inputs of template DNA from *C. parapsilosis*. The LOD of the assay was found to ~10 cell equivalents (FIG. 12).

Figure 13A:
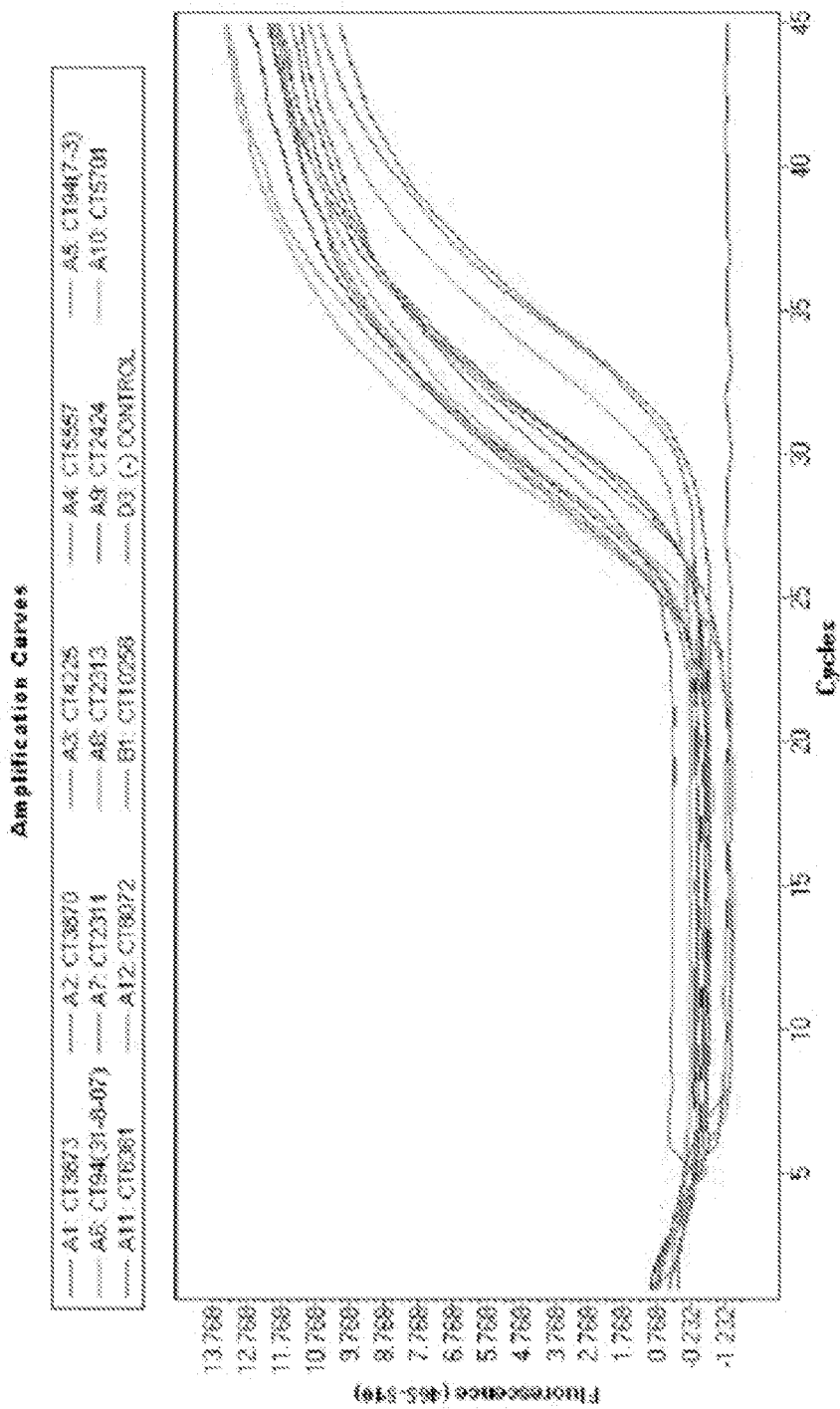
FIGS. 13A-13C: Amplification plot from Real-time PCR assay for *C. tropicalis* based on the eIF2 γ gene with TaqMan probe TropicA. Specificity of the assay was tested using a panel of DNA from 12 *C. tropicalis* strains, 19 other *Candida* species, *Aspergillus fumigatus* and *Saccharomyces cerevisiae*.
Figure 13B:
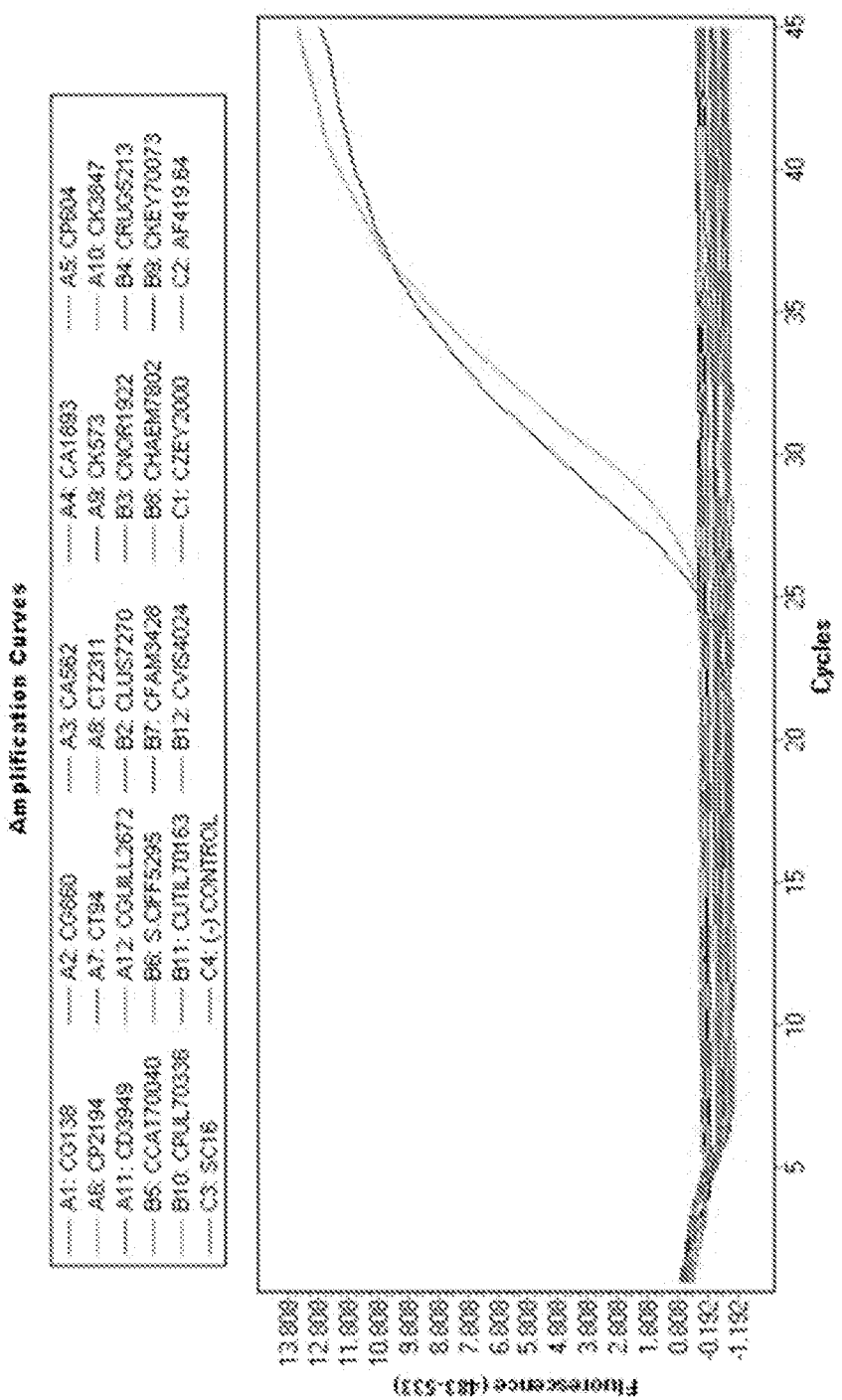
Figure 13C:
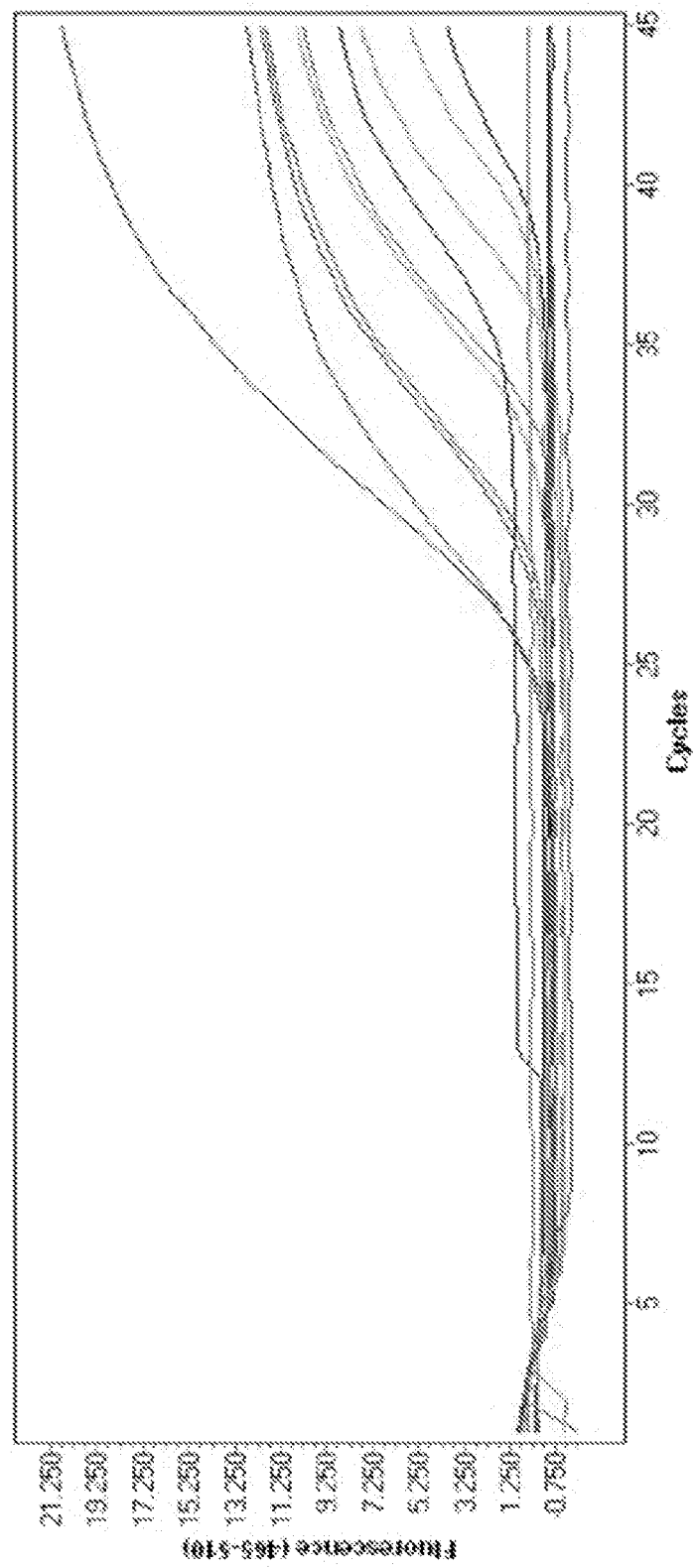

For the *C. tropicalis* assay based on the eIF2γ gene, PCR primers TropicF1/TropicR1 were combined with TaqMan probe, TropicA. The specificity of the assay for the detection of *C. tropicalis* was confirmed by including DNA from a range of closely related *Candida* species, *Saccharomyces cerevisiae* and *A. fumigatus* in the *C. tropicalis* real-time PCR assay. The assay detected twelve *C. tropicalis* strains tested but did not detect or cross-react with DNA from any other 19 *Candida* species tested or with *S. cerevisiae* or *A. fumigatus* DNA. Initial sensitivity of the assay was tested using various inputs of template DNA from *C. tropicalis*. The LOD of the assay was found to ~20 cell equivalents (FIG. 13).

Figure 14A:
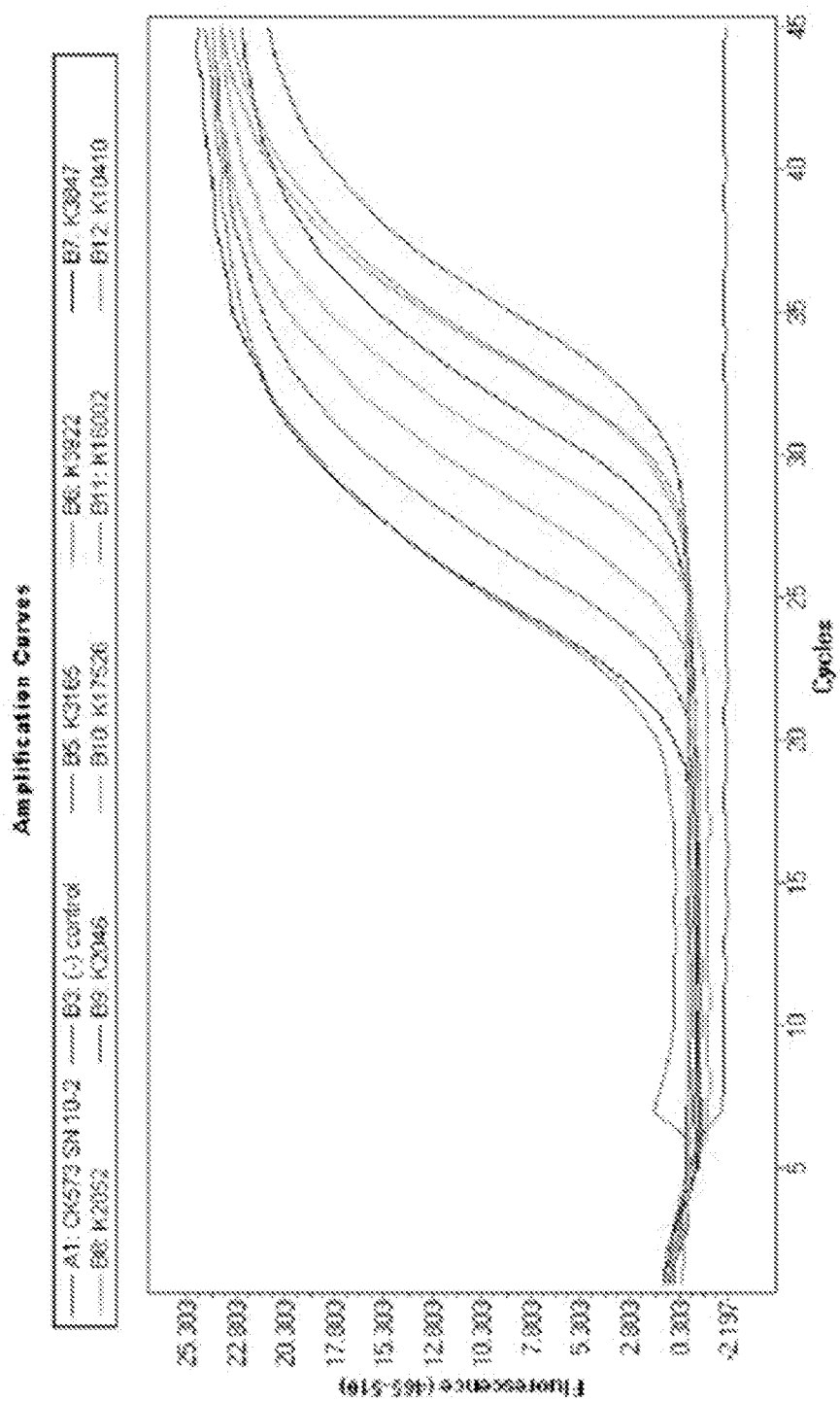
Figure 14B:
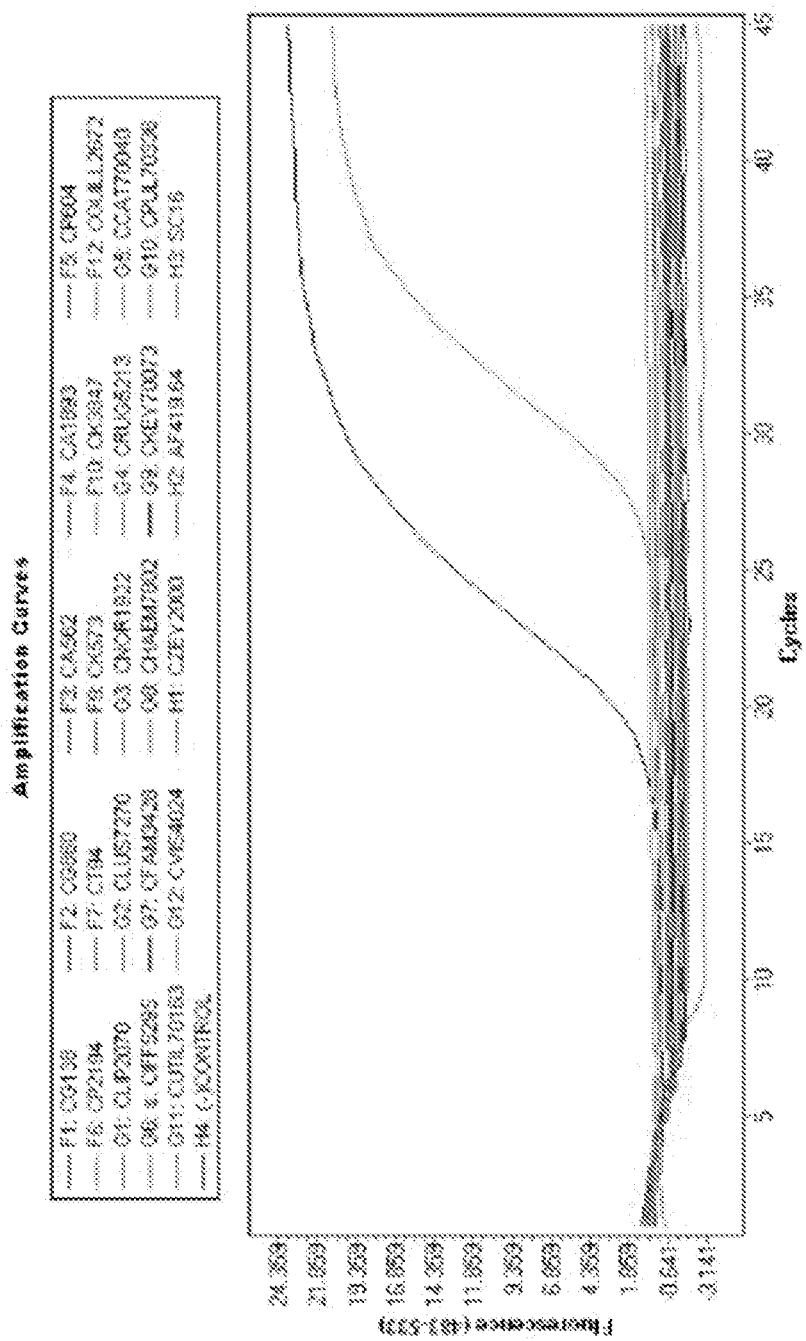
Figure 14C:
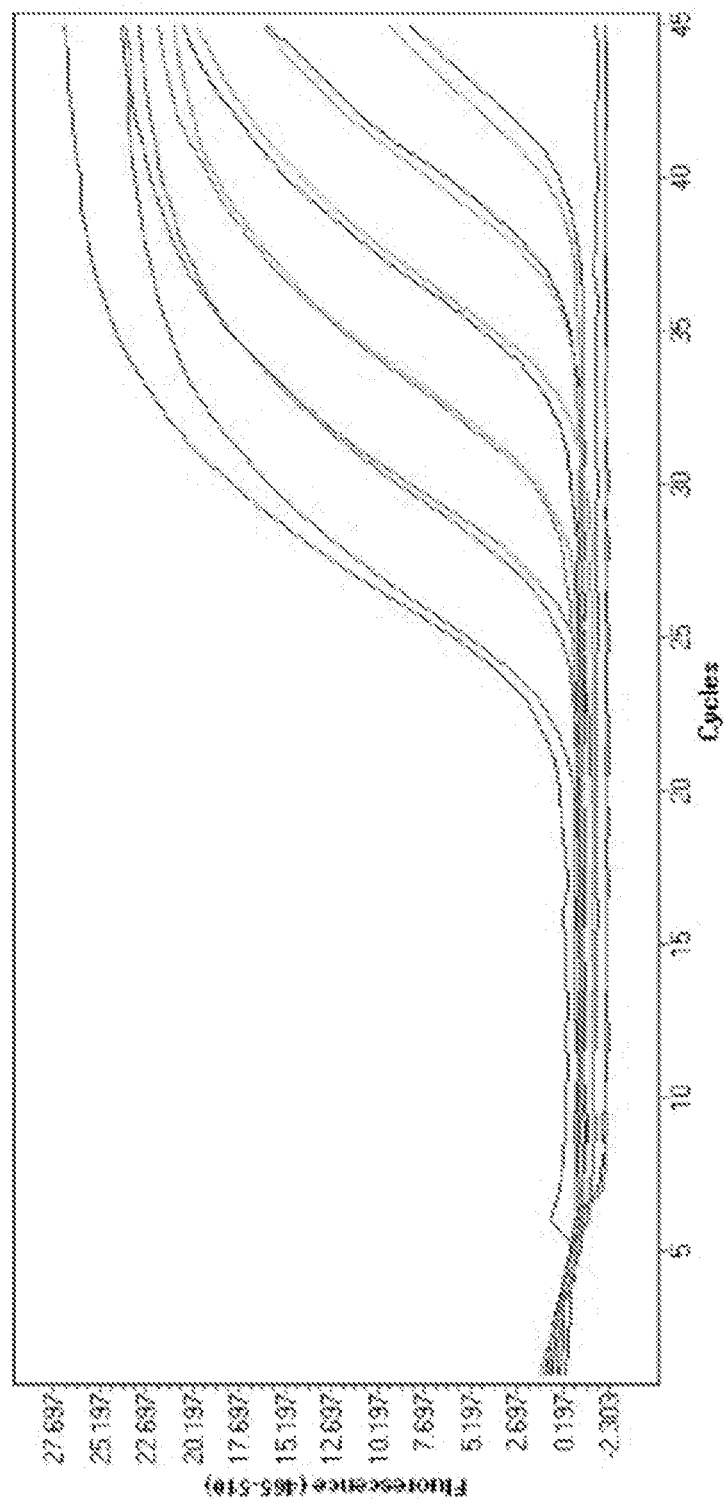

For the *C. krusei* assay based on the eIF2γ gene, PCR primers KrusF1/KrusR1 were combined with TaqMan probe, KrusA. The specificity of the assay for the detection of *C. krusei* was confirmed by including DNA from a range of closely related *Candida* species, *Saccharomyces cerevisiae* and *A. fumigatus* in the *C. krusei* real-time PCR assay. The assay detected nine *C. krusei* strains tested but did not detect or cross-react with DNA from any other 19 *Candida* species tested or with *S. cerevisiae* or *A. fumigatus* DNA. Initial sensitivity of the assay was tested using various inputs of template DNA from *C. krusei*. The LOD of the assay was found to ~2 cell equivalents (FIG. 14).

*Aspergillus* spp
Primer and Probe Design

The publicly available sequence information for the eIF2γ gene in *Aspergillus* spp. was aligned with the newly generated sequence information for the eIF2γ gene in *Aspergillus* spp. and analyzed using bioinformatics tools (FIG. 15-18). Primers and probes were designed to amplify and detect *Aspergillus* species. Primers were designed which could amplify more than one species of interest. EF2_1_fow was designed to amplify *A. fumigatus* and *A. terreus*. EF2_2_fow was designed to amplify *A. flavus* and *A. niger*. EF2_1_rev was designed to amplify *A. fumigatus*. EF2_3_rev was designed to amplify *A. flavus*, *A. niger* and *A. terreus*. EF2_7_fow was designed to amplify *A. niger* and *A. flavus*. EF2_8_fow was designed to amplify *A. terreus*. EF2_9 fow was designed to amplify *A. fumigatus*. EF2_5 rev was designed to amplify *A. fumigatus*, *A. flavus*, and *A. terreus*. EF2_6_rev was designed to amplify *A. niger* Primers and probes used in these assays are listed in Table 11.

TABLE 11

Probes and primers designed for real time PCR assays for the detection of EIF2 target in *Aspergillus* spp.

| Oligo name | Sequence 5'-3' |
|---|---|
| EF2_1_fow | cagccgaagcg |
| EF2_2_fow | cagcccaagcg |
| EF2_3_fow | agccgaagcgYc |
| EF2_4_fow | agcccaagcggcc |
| EF2_5_fow | agccgaagcgtcc |
| EF2_6_fow | agccgaagcgccc |
| EF2_7_fow | agcccaagcggccaga |

TABLE 11-continued

Probes and primers designed for real time PCR assays for the detection of EIF2 target in *Aspergillus* spp.

| Oligo name | Sequence 5'-3' |
|---|---|
| EF2_8_fow | agccgaagcgcccaga |
| EF2_9_fow | agccgaagcgtccagaac |
| EF2_10_fow | agcgcccctgctcc |
| EF2_11_fow | cccgagcagcccgacc |
| EF2_1_rev | cgtgtgcgacgt |
| EF2_3_rev | cgtgagcgagtg |
| EF2_4_rev | cgtgwgcgacgt |
| EF2_5_rev | ggcctggcgcgcaat |
| EF2_6_rev | ggcttggcgcgcaat |
| EF2_7_rev | cgtgtgcgacgtgtccg |
| A.nig_EF2_1 | atccggagactctggacct |
| A.terr_EF2_1 | cgacgcttacccctctgt |
| A.flav_EF2_1 | cagacccgctaccctt |
| A.fum_EF2_1 | acgctcacacctctgtc |
| A.fum_EF2_2 | cgacgctcacacctctgtc |

Real Time PCR

Assay exclusivity was investigated with the panel outlined in Table 12.

TABLE 12

Panel for assay exclusivity evaluation
Species name

*A. fumigatus* 110.46
*A. flavus* 117.62
*A. niger* 2599
*A. terreus* 2729
*A. candidus* 102.13
*A. clavatus* 1348
*A. glaucus* 117314
*A. nidulans* 670
*A. versicolor* 2916
*N. fischeri* 211390

TABLE 13

Thermocycling conditions

| Step | Temp | Time | |
|---|---|---|---|
| UNG | 50° C. | 2 min | |
| Denaturation | 95° C. | 1 min | |
| Cycling | 95° C. | 5-10 secs | 40 or 45 or 50 cycles |
| | 60° C. | 10-30 secs | |
| Cooling | 40° C. | 1-2 mins | |

Evaluation of Assay Exclusivity

The initial evaluation of assay exclusivity was investigated with the panel outlined in Table 12 and the primers and probes outlined in Table 13. The results of these assays performed with annealing times of 95° C. for 10 seconds and 60° C. for 30 seconds for 50 cycles show that the assays were specific for exclusive detection of only the species for which they were designed.

Figure 19A:
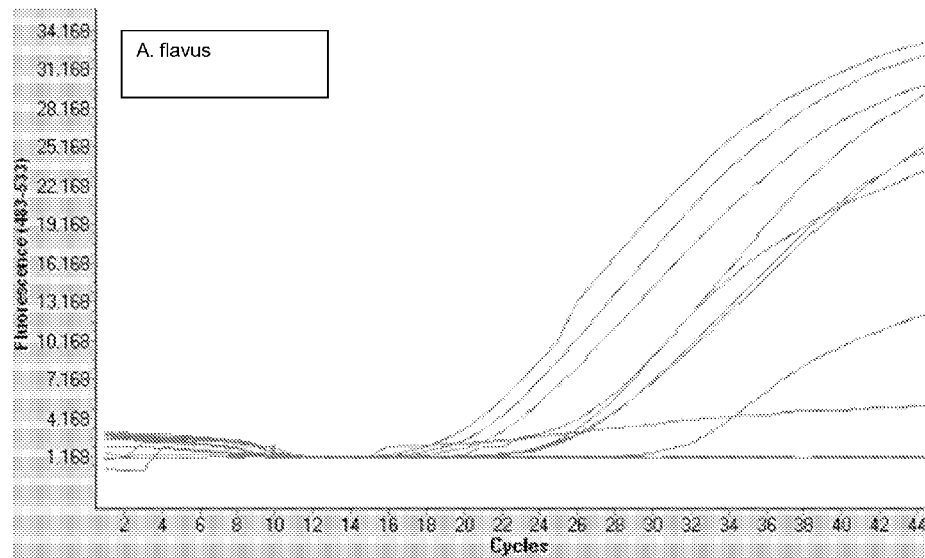
FIGS. 19A-19C: The *A. flavus, A. niger* and *A. terreus* assays were tested for inclusivity with nine available in-house strains of each species. EF2_7_fow and EF2_5_rev were used in the *A. flavus* assay. EF2_7_fow and EF2_6_rev primer pair for the *A. niger* assay and EF2_8_fow and EF2_5_rev included in the *A. terreus* assay. The annealing conditions of 95° C. for 5 seconds and 60° C. for 10 seconds for 45 cycles were applied to each assay. All strains were detected by the relevant specific probe.
Figure 19B:
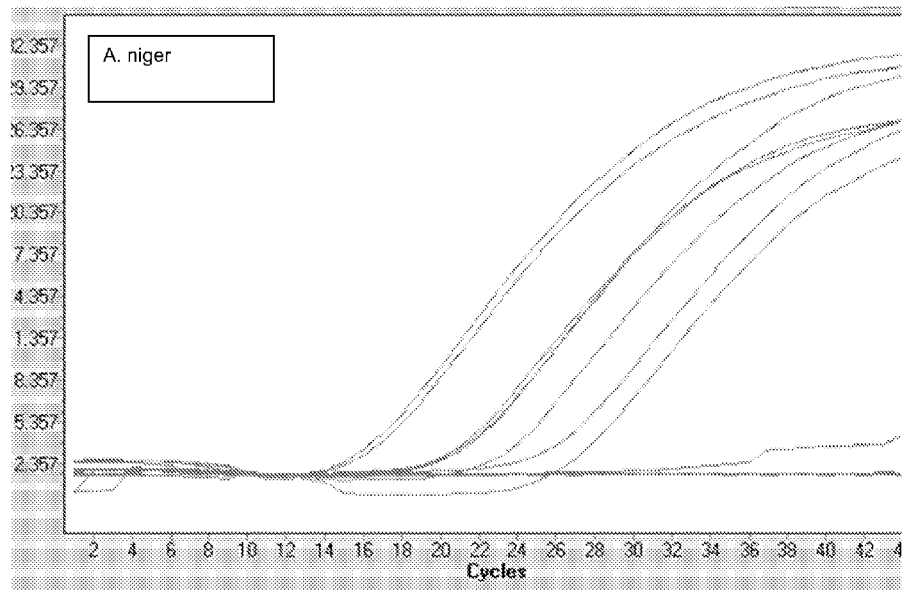
Figure 19C:
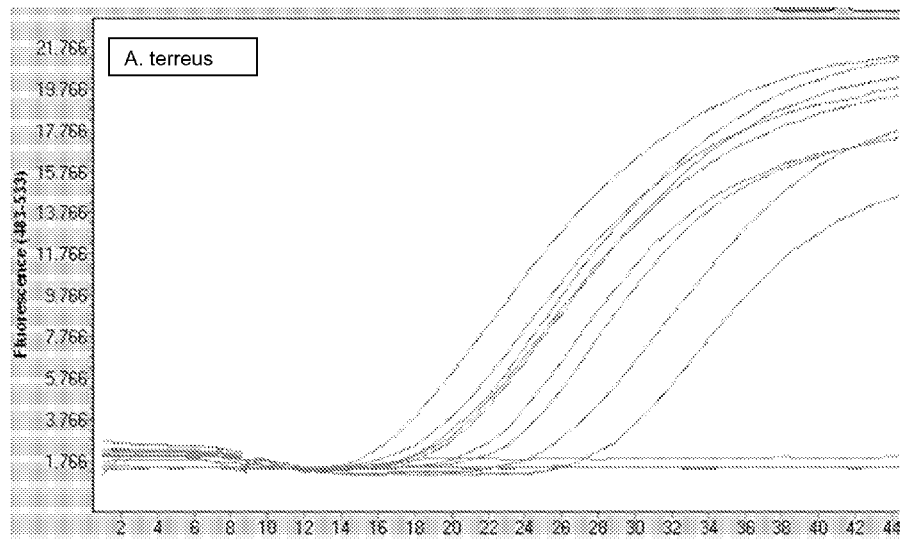

The *A. flavus, A. niger* and *A. terreus* assays were tested for inclusivity with nine available in-house strains of each species. EF2_7_fow and EF2_5_rev were used in the *A. flavus* assay. EF2_7_fow and EF2_6_rev primer pair for the *A. niger* assay and EF2_8_fow and EF2_5_rev included in the *A. terreus* assay. The annealing conditions of 95° C. for 5 seconds and 60° C. for 10 seconds for 45 cycles were applied to each assay. All strains were detected by the relevant specific probe (FIG. 19).

Figure 20A:
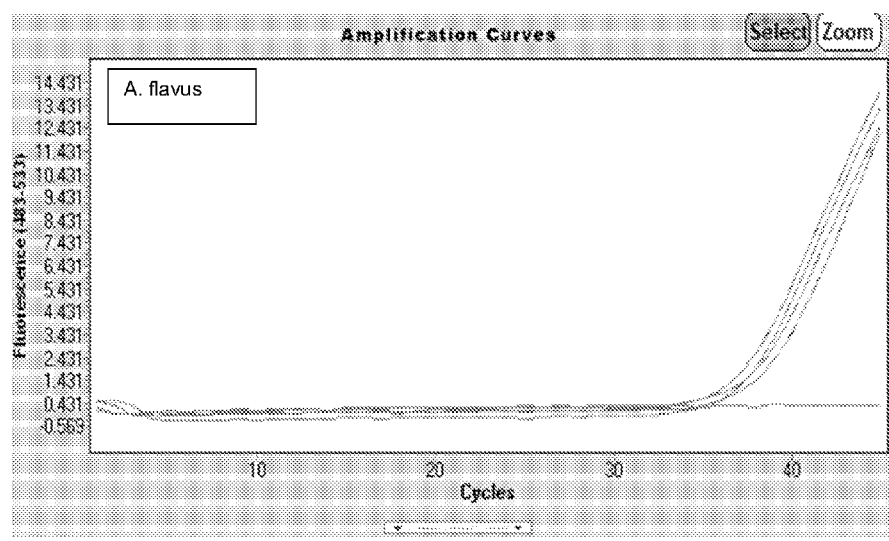
FIGS. 20A-20C: The same primer combinations and thermocycling conditions were used in the LOD assays for *A. flavus, A. niger* and *A. terreus*. The LOD for each of the three assays were found to be 5 cell equivalents per reaction.
Figure 20B:
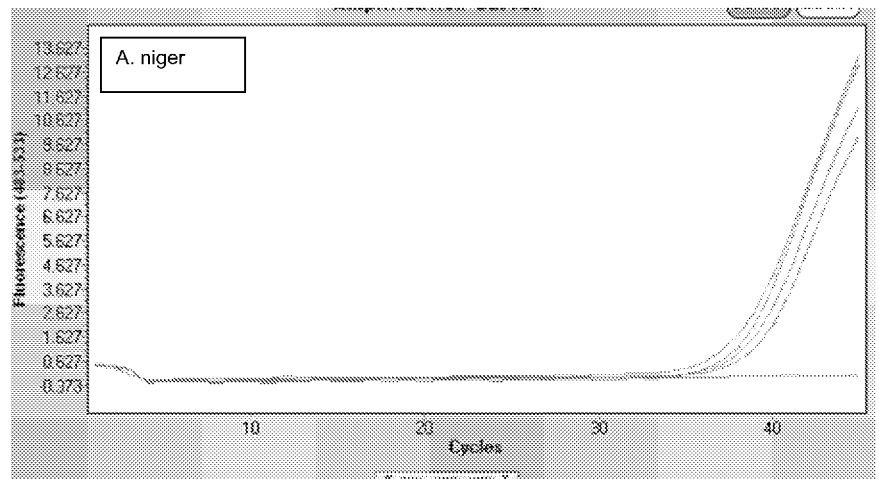
Figure 20C:
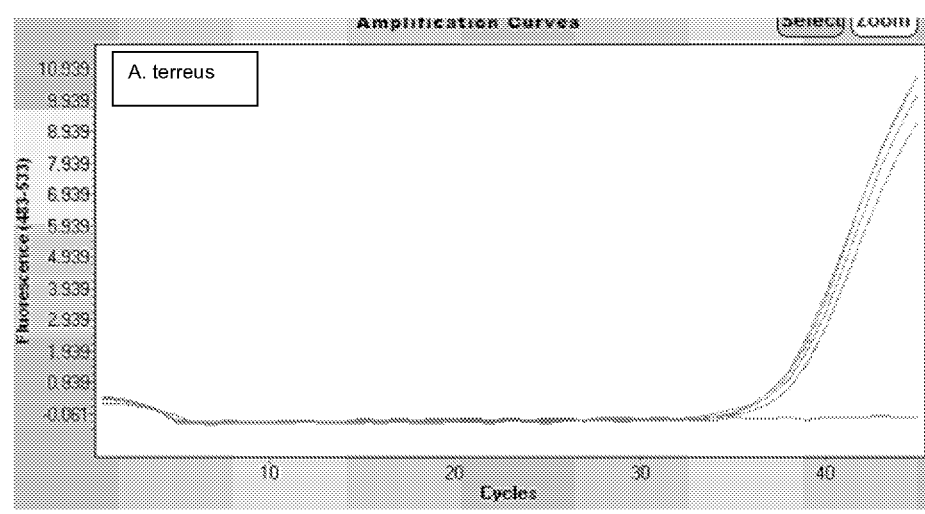

The same primer combinations and thermocycling conditions were used in the LOD assays for *A. flavus, A. niger* and *A. terreus*. The LOD for each of the three assays were found to be 5 cell equivalents per reaction. (FIG. 20)

Figure 21A:
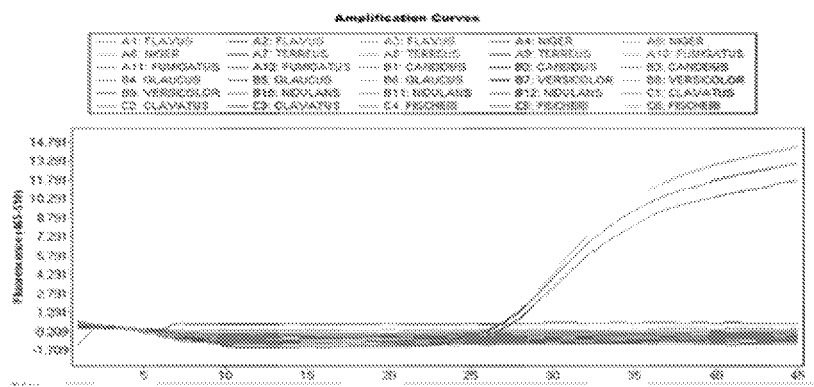
FIGS. 21A-21C: The same assay conditions were used to test the exclusivity of the *A. flavus, A. niger* and *A. terreus* assays. Each of the three assays was found to be specific, detecting only the species of interest with no cross-reactivity with other closely related *Aspergillus* species included in the assay. All samples were tested in triplicate.
Figure 21B:
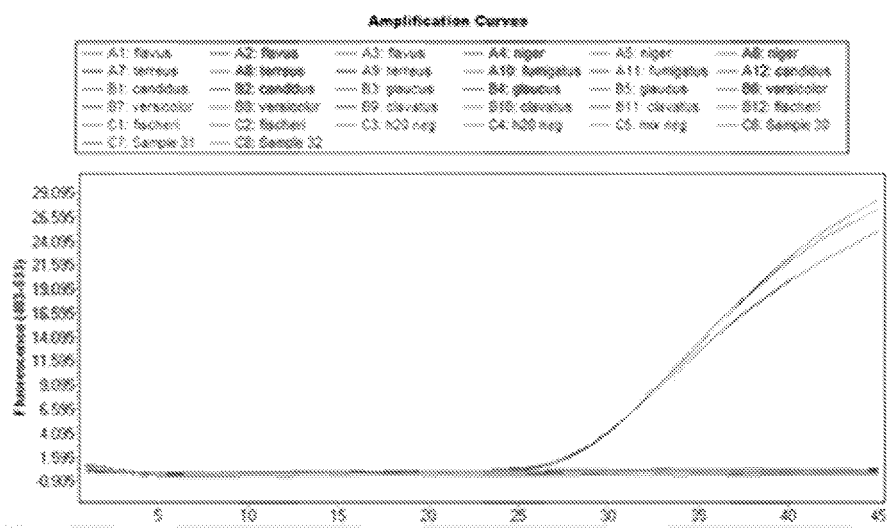
Figure 21C:
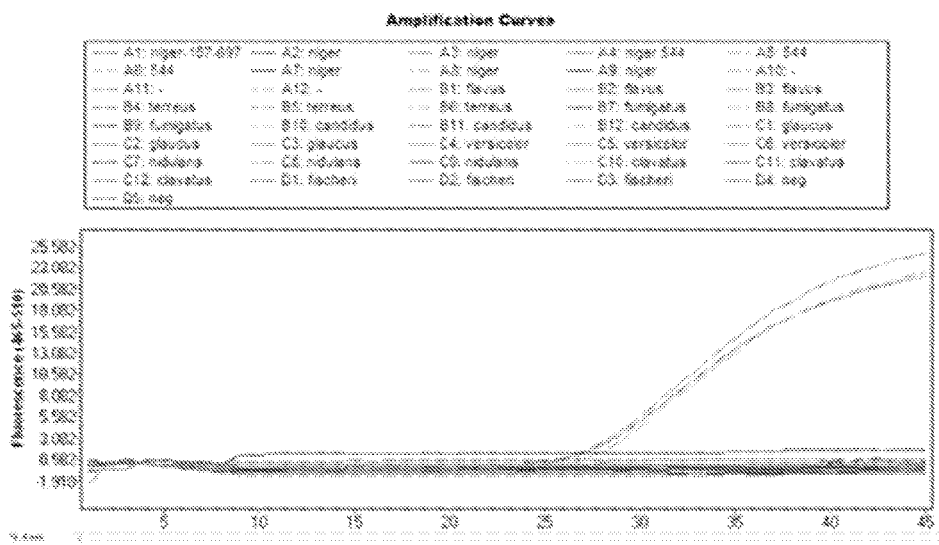

The same assay conditions were used to test the exclusivity of the *A. flavus, A. niger* and *A. terreus* assays. Each of the three assays was found to be specific, detecting only the species of interest with no cross-reactivity with other closely related *Aspergillus* species included in the assay. All samples were tested in triplicate. (FIG. 21).

Figure 22:
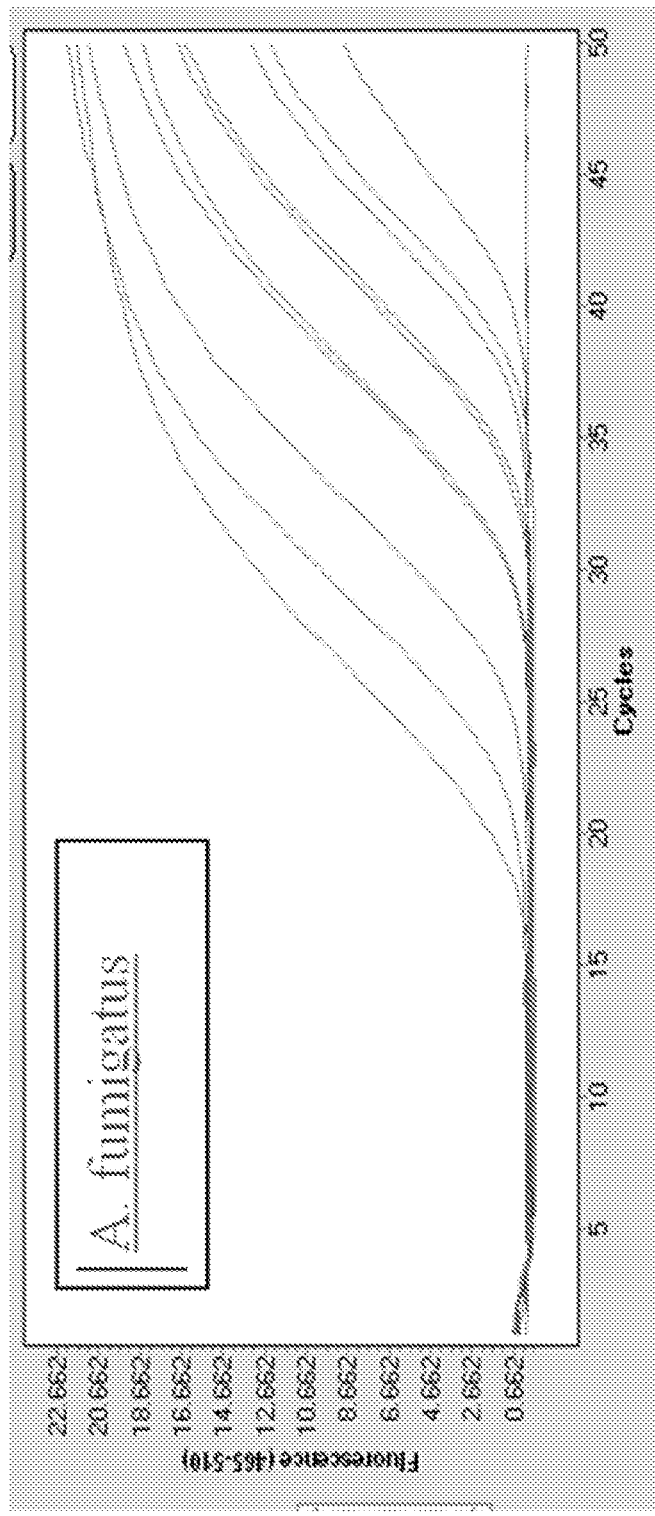
FIG. 22: LOD of the *A. fumigatus* assay was performed under thermocycling conditions which included for the *A. fumigatus* annealing conditions of 95° C. for 10 seconds and 60° C. for 30 seconds for 50 cycles. The LOD for this assay was found to be 10-1 cell equivalents.

LOD of the *A. fumigatus* assay was performed under thermocycling conditions which included for the *A. fumigatus* annealing conditions of 95° C. for 10 seconds and 60° C. for 30 seconds for 50 cycles. The LOD for this assay was found to be 10-1 cell equivalents (FIG. 22).

Discussion

The number of yeast and fungal infections among immunocomprised patients is escalating. Contributing to this increase is the growing resistance of many yeast and fungal species to antifungal drugs. There is therefore a need to develop a fast, accurate diagnostic method to enable early diagnosis of yeast and fungal species. Early diagnosis will enable the selection of a specific narrow spectrum antibiotic or antifungal to treat the infection. The current invention provides for sequences and/or diagnostic assays to detect and identify one or more yeast and fungal species. The current inventors have exploited the sequence of the eIF2 γ gene in *Candida* and *Aspergillus* species to design primers and probes specific for regions of this gene. The eIF2 γ sequence has significant intragenic sequence heterogeneity in some regions, while having significant homogeneity in others, a trait, which makes eIF2 γ an ideal candidate for the design of primers and probes directed towards the detection of yeast and fungal species specific targets and for the detection of genus specific diagnostic targets respectively.

The current invention allows the detection of yeast and fungal species but also allows distinction between *Candida* and *Aspergillus* species. It is a further object of the invention to allow the discrimination between different *Candida* species and different *Aspergillus* species. The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

In so far as any sequence disclosed herein differs from its counterpart in the attached sequence listing in PatentIn3.3 software, the sequences within this body of text are to be considered as the correct version.

SEQ IDs

Sites of probes, oligonucleotides etc. are shown in bold and underlined.

N or x=any nucleotide; w=a/t, m=a/c, r=a/g, k=g/t, s=c/g, y=c/t, h=a/t/c, v=a/g/c, d=a/g/t, b=g/t/c. In some cases, specific degeneracy options are indicated in parenthesis: e.g.: (a/g) is either A or G.

```
SEQ ID NO. 1: P1-CaneIF2:        CGATAATGCTCCGATCGTGCCTA

SEQ ID NO. 2: P1-AspeIF2:        CGCTCACACCTCTGTCGCCCGAA

SEQ ID NO. 3: AspeIF2-F:         CTTAAGTCTGCGATGAAGA

SEQ ID NO. 4: AspeIF2-R:         GTAATGTTACGCTCCAACTC

SEQ ID NO. 5: CaneIF2-F:         GCTGCCATTGAAATTATGAA

SEQ ID NO. 6: CaneIF2-R:         GAACCACCTGCAACACC

SEQ 1D NO.7:
>CA2700E4 eIF2 γ\(CaneIF2-F) eIF2 γ sequence generated for C.
albicans
TGCATAATAAAGTTGATTTGATGAGAGAAGAATCAGCCTTGGAACACGAAAAATCT

ATCATTCAGTTTATTAGAGGTACAATTGCCGATAATGCTCCGATCGTGCCTATTTCT

GCTCAATTGAAATACAACATTGATGCAGTGAATCAATTTATTGTTAACTACATACCT

GTGCCAATGAGAGACTTTACTGCTTCACCAAGATTGATCGTTATCAGATCTTTCGAT

GTGAACAAGCCTGGTGCAGATGTAGACGAATTGAAAGGAGGTGTTGCAGGTGGTTC

SEQ 1D NO. 8:
>A765\(EF) sequence generated for C. albicans
ATTATTTTGCATAATAAAGTTGATTTGATGAGAGAAGAATCAGCYTTGGAACACGAAAAA

TCTATCATTCAGTTTATTAGAGGTACAATTGCCGATAATGCTCCGATCGTGCCTATTTCT

GCTCAATTRAAATACAACATTGATGCAGTGAATCAATTTATYGTTAACTACATACCTGTG
```

-continued

CCAATGAGAGACTTTACTGCTTCACCAAGATTGATYGTTATCAGATCTTTCGATGTGAAC

AAGCCTGGTGCAGATGTAGACGAATTGAAAGGAGGTGTTGCAGGTGGTTC

SEQ 1D NO. 9:
>A3156\(EF) sequence generated for C. albicans
ATTATTTTGCATAATAAAGTTGATTTGATGAGAGAAGAATCAGCYTTGGRACACGAAAAA

TCTATCATTCAGTTTATTAGAGGTACAATTGCCGATAATGCTCCGATCGTGCCTATT

TCTGCTCAATTGAAATACAACATTGATGCAGTGAATCAATTTATYGTTAACTACATACCT

GTGCCAATGAGAGACTTTACTGCTTCACCAAGATTGATYGTTATCAGATCTTTCGATG

TGAACAAGCCTGGTGCAGATGTAGACGAATTGAAAGGAGGTGTTGCAGGTGGTTC

SEQ 1D NO. 10:
>A562\(EF) sequence generated for C. albicans
ATTGAAACATGTTATTATTTTGCATAATAAAGTTGATTTGATGAGAGAAGAATCAG

CCTTGGAACACGAAAAATCTATCATTCAGTTTATTAGAGGTACAATTGCCGATAAT

GCTCCGATCGTGCCTATTTCTGCTCAATTGAAATACAACATTGATGCAGTGAATCAA

TTTATTGTTAACTACATACCTGTGCCAATGAGAGACTTTACTGCTTCACCAAGATTG

ATCGTTATCAGATCTTTCGATGTGAACAAGCCTGGTGCAGATGTAGACGAATTGAA

AGGAGGTGTTGCAGGTGGTTC

SEQ ID NO. 11:
>CG3897E5\(EF)\(CaneIF2-F) eIF2 γ sequence generated for C. glabrata
GTTAAAGCACGTTATTATTCTACAGAACAAGGTCGATTTAATGCGTGAAGAAAGCG

CACTAGAACATGAAAAGTCTATCCTGAAATTTATCAGAGGTACTATTGCTGACGGT

GCTCCAATTGTCCCAATTTCCGCTCAATTGAAATACAACATCGATGCAGTTAATGAA

TTTATCGTGAAGACTATCCCTGTTCCACCAAGAGATTTCATGCTTTCTCCACGTTTG

ATTGTCATTCGTTCTTTCGATGTTAACAAGCCAGGTGCTGAAATCGATGATTTGAAG

GGTGGTGTTGCAGGTGGTTC

SEQ ID NO. 12:
>CG8018E6\(EF)\(CaneIF2-F) eIF2 γ sequence generated for C. glabrata
GTTAAAGCACGTTATTATTCTACAGAACAAGGTCGATTTAATGCGTGAAGAAAGCG

CACTAGAACATGAAAAGTCTATCCTGAAATTTATCAGAGGTACTATTGCTGACGGT

GCTCCAATTGTCCCAATTTCCGCTCAATTGAAATACAACATCGATGCAGTTAACGAA

TTTATCGTGAAGACTATCCCTGTTCCACCAAGAGATTTCATGCTTTCTCCACGTTTG

ATTGTCATTCGTTCTTTCGATGTTAACAAGCCAGGTGCTGAAATCGATGATTTGAAG

GGTGGTGTTGCAGGTGGTTC

SEQ ID NO. 13:
>CG4692E7\(EF)\(CaneIF2-F) eIF2 γ sequence generated for C. glabrata
GTTAAAGCACGTTATTATTCTACAGAACAAGGTCGATTTAATGCGTGAAGAAAGCG

CACTAGAACATGAAAAGTCTATCCTGAAATTTATCAGAGGTACTATTGCTGACGGT

GCTCCAATTGTCCCAATTTCCGCTCAATTGAAATACAACATCGATGCAGTCAATGAA

TTTATCGTGAAGACTATCCCTGTTCCACCAAGAGATTTCATGCTTTCTCCACGTTTG

ATTGTCATTCGTTCTTTCGATGTTAACAAGCCAGGTGCTGAAATCGATGATTTGAAG

GGTGGTGTTGCAGGTGGTTC

SEQ ID NO. 14:
>G138\(EF) sequence generated for C. glabrata
GTTAAAGCACGTTATTATTCTACAGAACAAGGTCGATTTAATGCGTGAAGAAAGCG

CACTAGAACATGAAAAGTCTATCCTGAAATTTATCAGAGGTACTATTGCTGACGGT

```
GCTCCAATTGTCCCAATTTCCGCTCAATTGAAATACAACATCGATGCAGTCAATGAA

TTTATCGTGAAGACTATCCCTGTTCCACCAAGAGATTTCATGCTTTCTCCACGTTTG

ATTGTCATTCGTTCTTTCGATGTTAACAAGCCAGGTGCTGAAATCGATGATTTGAAG

GGTGGTGTTGCAGGTGGTTC

SEQ ID NO. 15:
>CK3165E9\(EF)\(CaneIF2-F) eIF2 γ sequence generated for C.
krusei
TGKTGTGATTKTACAAAATAAAGTTGATTTGATGAAGAAAGAAGCAGCTTTAGAGC

ACGAAAAATCTATTTTGAAGTTTATCAAGGGTACTATTGCTGATGGTGCTCCTATTA

TCCCAATTTCTGCTCAGTTGAAATACAACATTGATGCAGTTAACATGTGTATGGTCA

AGTCTATTCCTGTTCCAATTAGAGACTTTACTGCAGTTCCAAGATTAATGGTTATTA

GATCTTTCGATGTTAATAAGCCTGGTGCAGAAATTGCAGATTTGAAAGGTGGTGTT

GCAGGTGGTTC

SEQ ID NO. 16:
>K9560\(EF) sequence generated for C. krusei
TGTTGTGATTTTACAAAATAAAGTTGATTTGATGAAGAAAGAAGCAGCTTTAGAGCACGAAAA

ATCTATTTTGAAGTTTATCAAGGGTACTATTGCTGATGGTGCTCCTATTATCCCAATTTCTG

CTCAGTTGAAATAYAACATTGATGCAGTTAACATGTGTATGGTCAAGTCTATTCCTGTT

CCAATTAGAGACTTTACYGCAGTTCCAAGATTAATGGTTATTAGATCTTTCGATGTTAATAA

GCCTGGTGCAGAAATTGCAGATTTGAAAGGTGGTGTTGCAGGTGGTTC

SEQ ID NO. 17:
>K6055\(EF) sequence generated for C. krusei
TGTTGTGATTTTACAAAATAAAGTTGATTTGATGAAGAAAGAAGCAGCTTTAGAGC

ACGAAAAATCTATTTTGAAGTTTATCAAGGGTACTATTGCTGATGGTGCTCCTATTA

TCCCAATTTCTGCTCAGTTGAAATATAACATTGATGCAGTTAACATGTGTATGGTCA

AGTCTATTCCTGTTCCAATTAGAGACTTTACCGCAGTTCCAAGATTAATGGTTATTA

GATCTTTCGATGTTAATAAGCCTGGTGCAGAAATTGCAGATTTGAAAGGTGGTGTT

GCAGGTGGTTC

SEQ ID NO. 18:
>K573E\(EF) sequence generated for C. krusei
TGKTGTGATTKTACAAAATAAAGTTGATTTGATGAAGAAAGAAGCAGCTTTAGAGC

ACGAAAAATCTATTTTGAAGTTTATCAAGGGTACTATTGCTGATGGTGCTCCTATTA

TCCCAATTTCTGCTCAGTTGAAATATAACATTGATGCAGTTAACATGTGTATGGTCA

AGTCTATTCCTGTTCCAATTAGAGACTTTACCGCAGTTCCAAGATTAATGGTTATTA

GATCTTTCGATGTTAATAAGCCTGGTGCAGAAATTGCAGATTTGAAAGGTGGTGTT

GCAGGTGGTTC

SEQ ID NO. 19:
>CP96141E14\(EF)\(CaneIF2-F) eIF2 γ sequence generated for
C. parapsilosis
GTTGAAGCATGTTATAATTTTGCAAAACAAGGTTGATTTGATGAGAGAAGARTCRG

CATTGGAACATGAAAAGTCTATTATTCAGTTCATAAGAGGTACCATAGCTGATGGT

GCACCAATAGTTCCAATTTCGGCACAATTGAAATATAATATCGATGCCGTCAATCA

ATTCATAGTCAACTCCATACCTGTCCCAGTTAGAGAYTTTACTGCATCACCAAGATT

GATTGTTATTAGGTCTTTYGATGTSAACAAACCTGGTGCTGATGTTGATGACTTGAA

GGGAGGTGTTGCAGGTGGTTC

SEQ ID NO. 20:
>CP2194E16\(EF)\(CaneIF2-F) eIF2 γ sequence generated for
C. parapsilosis
```

-continued

```
GTTGAAGCACGTTATTATTTTGCAAAACAAAGTTGATTTAATGAGAAAGGAGTCAG

CTTTGGAACATGAAAAGTCCATCATTCAGTTCATCAGAGGTACTATAGCTGATGGT

GCCCCAATTGTTCCAATTTCAGCACAATTGAAGTATAATATCGACGCCGTCAATCAA

TTCATCGTAAACTCAATACCAGTTCCAGTCAGGGACTTTACTGCATCCCCTAGGTTA

ATTGTTATTAGGTCTTTTGATGTGAACAAACCTGGTGCTGACGTTGATGATTTGAAA

GGAGGTGTTGCAGGTGGTTC

SEQ ID NO. 21:
>P96143\(EF) sequence generated for C. parapsilosis
TGTTATAATTTTACAAAATAAGGTTGATTTGATGAGAGAAGAGTCKGCATTGGAGC

ATGARAAGTCGATACTTCAATTCATAAGAGGTACTATAGCMGATGGTGCTCCAATT

GTTCCAATTTCAGCTCAATTGAAATACAATATCGACGCCGTCAATCAATTTATAGTA

AATTCCATACCSGTTCCAATTAGGGATTTCAATGCCTCACCAAGGTTGATTGTTATT

CGATCATTTGATGTGAAYAAACCTGGTGCTGATGTCGAYGATTTGAAGGGAGGTGT

TGCAGGTGGTTC

SEQ ID NO. 22:
>P-604\(EF)) sequence generated for C. parapsilosis
GTTGAAGCACGTTATTATTTTGCAAAACAAAGTTGATTTAATGAGAAAGGAGTCAG

CTTTGGAACATGAAAAGTCCATCATTCAGTTCATCAGAGGTACTATAGCTGATGGT

GCCCCAATTGTTCCAATTTCAGCACAATTGAAGTATAATATCGACGCCGTCAATCAA

TTCATCGTAAACTCAATACCAGTTCCAGTCAGGGACTTTACTGCATCCCCTAGGTTA

ATTGTTATTAGGTCTTTTGATGTGAACAAACCTGGTGCTGACGTTGATGATTTGAAA

GGAGGTGTTGCAGGTGGTTC

SEQ ID NO. 23:
>CT2311E19\(EF)\(CaneIF2-F) eIF2 γ sequence generated for
C. tropicalis
GGTCGATTTGATGAGAGAAGAATCTGCCTTGGAACATGAGAAATCCATTCTTCAAT

TCATCAGAGGTACTATTGCAGACAATGCTCCTATTGTCCCAATTTCTGCCCAATTGA

AATACAACATCGATGCCGTTAACCAATTTATTGTCAATTATATCCCAGTTCCATTGA

GAGACTTTTCCGCTTCCCCAAGATTGATTGTCATCAGATCTTTTGATGTCAACAAGC

CAGGTTCCGATGTCGAAGACTTGAAAGGGGGTGTTGCAGGTGGTTC

SEQ ID NO. 24:
>T2424\(EF) sequence generated for C. tropicalis
GGTCGATTTGATGAGAGAAGAATCTGCCTTGGAACATGAGAAATCCATTCTTCAAT

TCATCAGAGGTACTATTGCAGACAATGCTCCTATTGTCCCAATTTCTGCCCAATTGA

AATACAACATCGATGCCGTTAACCAATTTATTGTCAATTATATCCCAGTTCCATTGA

GAGACTTTTCCGCTTCCCCAAGATTGATTGTCATCAGATCTTTTGATGTCAACAAGC

CAGGTTCCGATGTCGAAGACTTGAAAGGGGGTGTTGCAGGTGGTTC

SEQ ID NO. 25:
>T94\(EF) sequence generated for C. tropicalis
GTCATKATTTTGCAGAACAAGGTCGATTTGATGAGAGAAGAATCTGCCTTGGAACATGAGAA

ATCCATTCTTCAATTCATCAGAGGTACTATTGCAGACAATGCTCCTATTGTCCCAATTTCT

GCCCAATTGAAATACAACATCGATGCCGTTAACCAATTTATTGTCAATTATATCCCAGTTC

CATTGAGAGACTTTTCCGCTTCCCCAAGATTGATTGTCATCAGATCTTTTGATGTCAA

CAAGCCAGGTTCCGATGTCGAAGACTTGAAAGGGGGTGTTGCAGGTGGTTC

SEQ ID NO. 26:
>T-3895\(EF) sequence generated for C. tropicalis
GGTCGATTTGATGAGAGAAGAATCTGCCTTGGAACATGAGAAATCCATTCTTCAAT
```

-continued

```
TCATCAGAGGTACTATTGCAGACAATGCTCCTATTGTCCCAATTTCTGCCCAATTGA

AATACAACATCGATGCCGTTAACCAATTTATTGTCAATTATATCCCAGTTCCATTGA

GAGACTTTTCCGCTTCCCCAAGATTGATTGTCATCAGATCTTTTGATGTCAACAAGC

CAGGTTCCGATGTCGAAGACTTGAAAGGGGGTGTTGCAGGTGGTTC

SEQ ID NO. 27:
>CD3949E21\(EF)\(CaneIF2-F) eIF2 γ sequence generated for
C. dubliniensis
AATAAAGTTGATTTGATGAGAGAAGAATCAGCTTTGGAACATGAAAAATCCATTAT

TCAGTTCATCAGAGGCACAATTGCTGATAACGCCCCAATTGTGCCTATTTCTGCGCA

ATTGAAATACAACATTGATGCTGTAAATCAATTTATTGTGAACTACATACCTGTGCC

AATGAGAGACTTTACTGCTTCACCAAGATTGATCGTTATTAGATCTTTTGATGTGAA

CAAGCCTGGTGCGGATGTTGACGAATTGAAAGGGGGTGTTGCAGGTGGTTC

SEQ ID NO. 28:
>CD7987E22\(EF)\(CaneIF2-F) eIF2 γ sequence generated for
C. dubliniensis
TGAAACATGTCATTATTTTGCAGAATAAAGTTGATTTGATGAGAGAAGAATCAGCT

TTGGAACATGAAAAATCCATTATTCAGTTCATCAGAGGCACAATTGCTGATAACGC

CCCAATTGTGCCTATTTCTGCGCAATTGAAATACAACATTGATGCTGTAAATCAATT

TATTGTGAACTACATACCTGTGCCAATGAGAGACTTTACTGCTTCACCAAGATTGAT

CGTTATTAGATCTTTTGATGTGAACAAGCCTGGTGCGGATGTTGACGAATTGAAAG

GGGGTGTTGCAGGTGGTTC

SEQ ID NO. 29:
>CD8501E23\(EF)\(CaneIF2-F) eIF2 γ sequence generated for
C. dubliniensis
ATTGAAACATGTCATTATTTTGCAGAATAAAGTTGATTTGATGAGAGAAGAATCAG

CTTTGGAACATGAAAAATCCATTATTCAGTTCATCAGAGGCACAATTGCTGATAAC

GCCCCAATTGTGCCTATTTCTGCGCAATTGAAATACAACATTGATGCTGTAAATCAA

TTTATTGTGAACTACATACCTGTGCCAATGAGAGACTTTACTGCTTCACCAAGATTG

ATCGTTATTAGATCTTTTGATGTGAACAAGCCTGGTGCGGATGTTGACGAATTGAAA

GGGGGTGTTGCAGGTGGTTC

SEQ ID NO. 30:
>CGU2672E25\(EF)\(CaneIF2-F) eIF2 γ sequence generated for
C. guilliermondii
TTGCAAAATAAGGTGGATCTTATGAGAGAAGAATCGGCGTTGGAGCACCAAAAATC

GATTTTGAATTTTATTAAAGGAACCATCGCTGACGGTGCCCCCATCGTCCCTATCTC

GGCCCAATTGAAGTACAACATCGATGCCGTGAACCAATTCATAGTCAACTCGATCC

CCGTTCCTCCTCGTGACTTTTCCGCATCTCCTCGGTTGATCGTGATTCGTTCTTTCGA

CGTCAATAAACCCGGTTCTGAAATTGATGACTTGAAGGGAGGTGTTGCAGGTGGTTC

SEQ ID NO. 31:
>CGU6021E26\(EF)\(CaneIF2-F) eIF2 γ sequence generated for
C. guillermondii
GTTGAAACATGTTATCATCTTGCAAAATAAGGTGGATCTTATGAGAGAAGAATCGG

CGTTGGAGCACCAAAAATCGATTTTGAATTTTATTAAAGGAACCATCGCTGATGGT

GCACCTATCGTCCCTATCTCGGCCCAGTTGAAGTACAACATCGATGCCGTGAACCA

ATTCATAGTCAACTCGATCCCCGTTCCTCCTCGTGACTTTTCCGCATCTCCTCGGTTG

ATCGTGATTCGTTCTTTCGACGTCAATAAACCCGGTTCTGAGATCGATGACTTGAAA

GGAGGTGTTGCAGGTGGTTC

SEQ ID NO. 32:
>Guil8167\(EF) sequence generated for C. guillermondii
```

```
GTTGAAACATGTTATCATCTTGCAAAATAAGGTGGATCTTATGAGAGAAGAATCGG

CGTTGGAGCACCAAAAATCGATTTTGAATTTTATTAAAGGAACCATCGCTGATGGT

GCACCTATCGTCCCTATCTCGGCCCAGTTGAAGTACAACATCGATGCCGTGAACCA

ATTCATAGTCAACTCGATCCCCGTTCCTCCTCGTGACTTTTCCGCATCTCCTCGGTTG

ATCGTGATTCGTTCTTTCGACGTCAATAAACCCGGTTCTGAGATCGATGACTTGAAA

GGAGGTGTTGCAGGTGGTTC

SEQ ID NO. 33:
>CN1922E33\(EF)\(CaneIF2-F) eIF2 γ sequence generated for
C. norvegiensis
GTTGAAACACGTTGTTATTTTACAAAATAAAGTTGATTTGATGAAAAAGGAAGCTG

CGTTGGAACACGAAAAATCTATTCTTAAGTTCATCAAGGGTACGATCGCTGATGGA

GCTCCAATCATTCCTATTTCTGCACAATTGAAATATAACATTGATGCTGTTAACATG

TGTATGGTAAACTCCATTCCAATTCCAATGAGAGATTTTACTGCTCAGCCAAGATTA

ATGGTCATCAGATCTTTCGATGTTAACAAACCTGGTGCAGAAATAAATGATTTGAA

AGGTGGTGTTGCAGGTGGTTC

SEQ ID NO. 34:
>FAM1E45\(EF)\(CaneIF2-F) eIF2 γ sequence generated for C. famata
ATTGARTCATGTTATTATCTTACAAAACAAGGTTGATTTAATGARAGAGGAATCAGCTTTGGAAC

ATCAGAAATCTATTTTGAGTTTCATCAGAGGTACTATTGCAGATGGTGCTCCAATTGTTCCAA

TTTCTGCCCAATTAAAATATAATATCGATGCTGTTAATCAATTTATTGTGAACTCTATTCCAA

TTCCTCCAAGAGACTTCATGGCTACTCCAAGATTGATCGTTATTAGATCTTTCGATGTTAATAAA

CCAGGTGCCGAGATTGATGACTTGAAGGGTGGTGTTGCAGGTGGTTC

SEQ ID NO. 35:
>FAM2E46\(EF)\(CaneIF2-F) eIF2 γ sequence generated for C. famata
GTGATTATCTTACAAAATAAGGTTGATTTAATGAGAGAAGAGTCAGCTTTAGAGCATCAAAA

GTCCATTTTGAGTTTCATCAGAGGTACTATTGCTGATGGTGCTCCAATTGTTCCAATTTCTGC

TCAATTAAAATATAATATTGATGCTGTCAATCAATTTATTGTTAATTCTATTCCAATTCCGCC

AAGAGACTTSATGGCTACTCCAAGATTGATCGATATTAGATCATTCGATGTTAATAAACCAGG

GGCAGAAATTGATGACTTGAAGGGTGGTGTTGCAGGTGGTTC

SEQ ID NO. 36:
>FAM5E47\(EF)\(CaneIF2-F) eIF2 γ sequence generated for C. famata
ATTGAAGCATGTGATCATCTTACAAAATAAGGTTGATTTAATGAGAGAAGAATCTG

CTTTAGAGCATCAAAAGTCCATTTTGAGTTTCATCAGAGGTACTATTGCTGATGGTG

CTCCAATTGTTCCAATTTCTGCTCAATTAAAATATAATATTGATGCTGTCAATCAAT

TTATTGTTAATTCTATTCCAATTCCGCCAAGAGACTTGATGGCTACTCCAAGATTGA

TCGATATTAGATCATTCGATGTTAATAAACCAGGTGCTGAAATTGATGACTTGAAG

GGTGGTGTTGCAGGTGGTTC

SEQ ID NO. 37:
>CH53E48\(EF)\(CaneIF2-F) eIF2 γ sequence generated for
C. haemuloni
CGTTATCATTTTGCAGAACAAGGTGGATTTGATGAGAGAAGAGTCTGCTTTGGAGC

ACCAGAAATCGATCTTGAGTTTTATCAGAGGTACCATTGCCGATGGCGCTCCTATCG

TGCCAATTTCCGCCCAATTGAAGTACAACATTGACGCTGTCAACCAGTTGATCTGCG

ACTACATCCCTGTTCCTCCTAGAGACTTCATGGCCTCGCCACGTTTGATCGTCATTA

GGTCTTTCGATGTCAACAAGCCAGGTGCCGAGATCGAGGACTTGAAGGGAGGTGTT

GCAGGTGGTTC

SEQ ID NO. 38:
```

-continued

>CH54E49\(EF)\(CaneIF2-F) eIF2 γ sequence generated for
C. haemuloni
CGTTATCATTTTGCAGAACAAGGTGGATTTGATGAGAGAAGAGTCTGCTTTGGAGC

ACCAGAAATCGATCTTGAGTTTTATCAGAGGTACCATTGCCGATGGCGCTCCTATCG

TGCCAATTTCCGCCCAATTGAAGTACAACATTGACGCTGTCAACCAGTTGATCTGCG

ACTACATCCCTGTTCCTCCTAGAGACTTCATGGCCTCGCCACGTTTGATCGTCATTA

GGTCTTTCGATGTCAACAAGCCAGGTGCCGAGATCGAGGACTTGAAGGGAGGTGTT

GCAGGTGGTTC

SEQ ID NO. 39:
>CH55E50\(EF)\(CaneIF2-F) eIF2 γ sequence generated for
C. haemuloni
CGTTATCATTTTGCAGAACAAGGTGGATTTGATGAGAGAAGAGTCTGCTTTGGAGC

ACCAGAAATCGATCTTGAGTTTTATCAGAGGTACCATTGCCGATGGCGCTCCTATCG

TGCCAATTTCCGCCCAATTGAAGTACAACATTGACGCTGTCAACCAGTTGATCTGCG

ACTACATCCCTGTTCCTCCTAGAGACTTCATGGCCTCGCCACGTTTGATCGTCATTA

GGTCTTTCGATGTCAACAAGCCAGGTGCCGAGATCGAGGACTTGAAGGGAGGTGTT

GCAGGTGGTTC

SEQ ID NO. 40:
>CKF57E51\(EF)\(CaneIF2-F) eIF2 γ sequence generated for C. kefyr
TTATTCTTCAGAACAAGGTGGATCTAATGAGAGAAGACTCCGCTCTAGAGCATCAA

AAATCTATTTTGAAGTTTATCAGAGGTACTATTGCCGATGGTGCACCAATTGTTCCA

ATTTCTGCTCAATTGAAGTACAATATTGATGCCGTTAACGAATTTATCGTTAAGAGT

ATCCCAGTTCCACAAAGAGACTTCTTAGCATCTCCAAGATTGATCGTCATCCGTTCT

TTTGACGTCAACAAGCCAGGTGCAGAAATTGATGATTTGAAGGGTGGTGTTGCAGGTGGTTC

SEQ ID NO. 41:
>CKF60E52\(EF)\(CaneIF2-F) eIF2 γ sequence generated for C. kefyr
TTATTCTTCAGAACAAGGTGGATCTAATGAGAGAAGACTCCGCTCTAGAGCATCAA

AAATCTATTTTGAAGTTTATCAGAGGTACTATTGCCGATGGTGCACCAATTGTTCCA

ATTTCTGCTCAATTGAAGTACAATATTGATGCCGTTAACGAATTTATCGTTAAGAGT

ATCCCAGTTCCACAAAGAGACTTCTTAGCATCTCCAAGATTGATCGTCATCCGTTCT

TTTGACGTCAACAAGCCAGGTGCAGAAATTGATGATTTGAAGGGTGGTGTTGCAGGTGGTTC

SEQ ID NO. 42:
>CKF3898E53\(EF)\(CaneIF2-F) eIF2 γ sequence generated for C.
kefyr
TTATTCTTCAGAACAAGGTGGATCTAATGAGAGAAGACTCCGCTCTAGAGCATCAA

AAATCTATTTTGAAGTTTATCAGAGGTACTATTGCCGATGGTGCACCAATTGTTCCA

ATTTCTGCTCAATTGAAGTACAATATTGATGCCGTTAACGAATTTATCGTTAAGAGT

ATCCCAGTTCCACAAAGAGACTTCTTAGCATCTCCAAGATTGATCGTCATCCGTTCTTTT

GACGTCAACAAGCCAGGTGCAGAAATTGATGATTTGAAGGGTGGTGTTGCAGGTGGTTC

SEQ ID NO. 43:
>Lus8013\(EF) sequence generated for C. lusitaniae
ACAAGGTCGACTTGATGAGAGAGGAGCTGGCGTTGGAGCACCAGAAATCCATTTTG

AGTTTCATCCGAGGCACCATCGCCGATGGCGCCCCTATCGTGCCTATCTCGGCCCAA

TTGAAGTACAACATTGACGCTGTCAACCAGATCATCTGCGACTACATTCCCGTGCCT

CCTCGAGACTTTATGGCGTCGCCCCGTTTGATTGTCATTAGATCTTTCGATGTGAAC

AAGCCAGGTGCCGAGATTGACGACTTGAAAGGTGGTGTTGCAGGTGGTTC

SEQ ID NO. 44:
>S.ciff-2305\(EF) sequence generated for S. cifferii
ATTGCAACATGTTATCATTCTGCAAAACAAGGTGGATCTCATGAAGGAGGAGTCCG

CCCTCGAGCATCACAAGAGCATTCTCAAGTTCATTCGAGGCACCATTGCCGACGGA

TCCCCAGTTATCCCCATTTCTGCCCAATTGAAGTACAACATTGACGCTGTCAACGAG

TTCATTGTGTCCAAGATCCCCATCCCCGTCAGAGATTTCCAGGCAACCCCACGATTG

ATTGTCATTAGATCATTCGATATCAACCGGCCCGGTTCCGAAATCGACGAGCTCCGT

GGTGGTGTTGCAGGTGGTTC

SEQ ID NO. 45:
>S.ciff-5295\(EF) sequence generated for S. cifferii
TCATGCAAAATAAGGTGGATCTCATGAAGGAGGAGTCCGCCCTCGAGCATCACAAG

AGCATTCTCAAGTTCATTCGGGGCACAATTGCCGACGGATCCCCAGTTATCCCCATT

TCTGCACAGCTGAAGTACAACATTGATGCTGTCAATGAGTTCATTGTTTCCAAGATC

CCAATCCCAGTCAGAGATTTCCAGGCCACCCCACGATTGATTGTCATTAGATCCTTC

GATATTAACCGTCCAGGTTCCGAAATCGACGAGCTTCGTGGCGGTGTTGCAGGTGGTTC

SEQ ID NO. 46:
>CU50E58\(EF)\(CaneIF2-F) eIF2 γ sequence generated for
C. utilis
ACAGGTGGATTTGATGCGTCCAGACTCTGCCTTGGAGCATGAGAAGTCGATTTTGA

AGTTCATCAGAGGTACCATTGCCGATGGTGCTCCAATCGTCCCAATCTCTGCTCAAT

TGAAATACAACATTGATGCTGTCAACGAATTCATCGTCAAGACTATCCCAGTGCCA

CCAAGAGACTTCAGTGCCTCTCCAAGACTCATTGTGATCCGTTCTTTTGACGTTAAC

AAACCAGGTGCCGAAATTGACGACTTGAAAGGTGGTGTTGCAGGTGGTTC

SEQ ID NO. 47:
>CV94E62\(EF)\(CaneIF2-F) eIF2 γ sequence generated for
C. viswanathii
GGTCGATTTGATGAGGGAAGAGTCCGCCTTGGAGCACGAGAAATCCATTCTCCAAT

TCATCAGAGGTACCATTGCCGACAATGCTCCTATTGTGCCAATTTCGGCGCAGTTGA

AGTACAACATCGACGCCGTGAACCAGTTTATTGTCAACTACATCCCAGTGCCATTG

AGAGACTTTTCTGCATCTCCAAGATTGATAGTCATCAGATCCTTTGATGTCAACAAG

CCAGGTTCGGACGTCGAAGAGTTGAAAGGTGGTGTTGCAGGTGGTTC

SEQ ID NO. 48:
>F419-64\(AspEF-F) sequence generated for A. fumigatus
CGAAGCGTCCAGAACTCCCCGAGCAGCCCGACCCAGAGACTCTCGATTTGTCGACG

CTCACACCTCTGTCGCCCGAAATTATTGCGCGCCAGGCCACAATCAACATCGGTACT

ATCGGACACGTCGCACACGGCAAGTCGACTGTTGTGAAGGCTATCTCGGAGGTGCA

GACTGTCCGGTTCAAAAATGAGTTGGAGCGTAACATTAC

SEQ 1D NO. 49:
>F483-61\(AspEF-F) sequence generated for A. fumigatus
AGCGCCCCCTGCTCCTCAGCCGAAGCGTCCAGAACTCCCCGAGCAGCCCGACCCAG

AGACTCTCGATTTGTCGACGCTCACACCTCTGTCGCCCGAAATTATTGCGCGCCAGG

CCACAATCAACATCGGTACTATCGGACACGTCGCACACGGCAAGTCGACTGTTGTG

AAGGCTATCTCGGAGGTGCAGACTGTCCGGTTCAAAAATGAGTTGGAGCGTAACATTAC

SEQ 1D NO. 50:
>F7273\(AspEF-F) sequence generated for A. fumigatus
AGCGCCCCCTGCTCCTCAGCCGAAGCGTCCAGAACTCCCCGAGCAGCCCGACCCAG

AGACTCTCGATTTGTCGACGCTCACACCTCTGTCGCCCGAAATTATTGCGCGCCAGG

CCACAATCAACATCGGTACTATCGGACACGTCGCACACGGCAAGTCGACTGTTGTG

AAGGCTATCTCGGAGGTGCAGACTGTCCGGTTCAAAAATGAGTTGGAGCGTAACATTAC

SEQ 1D NO. 51:
>F6951\(AspEF-F) sequence generated for A. fumigatus

```
AGCGCCCCCTGCTCCTCAGCCGAAGCGTCCAGAACTCCCCGAGCAGCCCGACCCAG

AGACTCTCGATTTGTCGACGCTCACACCTCTGTCGCCCGAAATTATTGCGCGCCAGG

CCACAATCAACATCGGTACTATCGGACACGTCGCACACGGCAAGTCGACTGTTGTG

AAGGCTATCTCGGAGGTGCAGACTGTCCGGTTCAAAAATGAGTTGGAGCGTAACATTAC

SEQ ID NO. 52:
>F133-61\(AspEF-F) eIF2 γ sequence generated for A. fumigatus
CCGAAGCGTCCAGAACTCCCCGAGCAGCCCGACCCAGAGACTCTCGATTTGTCGAC

GCTCACACCTCTGTCGCCCGAAATTATTGCGCGCCAGGCCACAATCAACATCGGTA

CTATCGGACACGTCGCACACGGCAAGTCGACTGTTGTGAAGGCTATCTCGGAGGTG

CAGACTGTCCGGTTCAAAAATGAGTTGGAGCGTAACATTAC

SEQ ID NO. 53:
>1085-eIF2 γ\(AspeIF2-F) eIF2 γ sequence generated for N. fischeri
CGGCCCCCGTTCCTCAGCCGAAGCGTCCAGAACTGCCCGAGCAGCCCAACCCAGAG

ACTCTCGATCTGTCGACACTGACGCCTCTGTCTCCCGAGATTATCGCGCGCCAGGCC

ACAATCAACATCGGTACTATCGGACACGTCGCTCACGGCAAGTCGACCGTGGTGAA

GGCTATTTCGGAGGTGCAGACTGTCCGGTTCAAGAACGAGTTGGAGCGTAACATTAC

SEQ ID NO. 54:
>5138eIF2 γ\(AspeIF2-F) eIF2 γ sequence generated for A. clavatus
AGGGCTCCATGCCCCCAGTTCCTCAACCGAAGCGCCCAGAACTGCCCGAGCAGCCTGACCCAGA

GACCATCGATCTGTCGAAACTGACGCCTCTGTCCCCCGAAATTATCGCGCGCCAGGCCACGATCA

ACATTGGTACCATCGGACACGTCGCTCACGGCAAGTCGACCGTGGTGAAGGCTATCTCGGAGGT

GCAGACGGTCCGTTTCAAGAACGAGTTGGAGCGTAACATTAC

SEQ ID NO. 55:
>C1348\(AspEF-F) sequence generated for A. clavatus
CATGCCCCCAGTTCCTCAACCGAAGCGCCCAGAACTGCCCGAGCAGCCTGACCCAG

AGACCATCGATCTGTCGAAACTGACGCCTCTGTCCCCCGAAATTATCGCGCGCCAG

GCCACGATCAACATTGGTACCATCGGACACGTCGCTCACGGCAAGTCGACCGTGGT

GAAGGCTATCTCGGAGGTGCAGACGGTCCGTTTCAAGAACGAGTTGGAGCGTAACATTAC

SEQ ID NO. 56:
>C2391\(AspEF-F) sequence generated for A. clavatus
AAGCGCCCAGAACTCCCCGAGCAGCCTGACCCAGAGACCATCGATCTGTCGAAACT

GACGCCTTTGTCCCCCGAAATCATCGCGCGCCAGGCCACGATCAACATTGGTACCA

TCGGGCACGTCGCTCACGGCAAGTCGACCGTGGTGAAGGCTATTTCGGAGGTGCAA

ACTGTTCGTTTCAAGAACGAGTTGGAGCGTAACATTAC

SEQ ID NO. 57:
>NIG2864\(AspEF-F) sequence generated for A. niger
TTCCTCCTCCCCAGCCCAAGCGGCCAGAGCTGCCCGAGCAGCCGAATCCGGAGACT

CTGGACCTGTCCACCCTGACTCCTTTGACCCCCGAAATTATTGCGCGCCAAGCCACA

ATCAACATTGGCACCATCGGTCACGTCGCTCACGGCAAGTCGACGGTCGTTAAGGC

TATCTCCGAGGTCCAGACTGTCCGTTTCAAGAACGAGTTGGAGCGTAACATTAC

SEQ ID NO. 58:
>NIG6727\(AspEF-F) sequence generated for A. niger
TTCCTCCTCCCCAGCCCAAGCGGCCAGAGCTGCCCGAGCAGCCGAATCCGGAGACT

CTGGACCTGTCCACCCTGACTCCTTTGACCCCCGAAATTATTGCGCGCCAAGCCACA

ATCAACATTGGCACCATCGGTCACGTCGCTCACGGCAAGTCGACGGTCGTTAAGGC

TATCTCCGAGGTCCAGACTGTCCGTTTCAAGAACGAGTTGGAGCGTAACATTAC

SEQ ID NO. 59:
>NIG328399\(AspEF-F) sequence generated for A. niger
TTCCTCCTCCCCAGCCCAAGCGGCCAGAGCTGCCCGAGCAGCCGAATCCGGAGACT
```

-continued

CTGGACCTGTCCACCCTGACTCCTTTGACCCCCGAAATTATTGCGCGCCAAGCCACA

ATCAACATTGGCACCATCGGTCACGTCGCTCACGGCAAGTCGACGGTCGTTAAGGC

TATCTCCGAGGTCCAGACTGTCCGTTTCAAGAACGAGTTGGAGCGTAACATTAC

SEQ ID NO. 60:
>NIGMA5184\(AspEF-F) sequence generated for *A. niger*
TTCCTCCTCCCCAGCCCAAGCGGCCAGAGCTGCCCGAGCAGCCGAATCCGGAGACT

CTGGACCTGTCCACGCTGACTCCTTTGACCCCCGAAATTATTGCGCGCCAAGCCACA

ATCAACATTGGCACCATCGGTCACGTCGCTCACGGCAAGTCGACGGTCGTTAAGGC

TATCTCCGAGGTCCAGACTGTCCGTTTCAAGAACGAGTTGGAGCGTAACATTAC

SEQ ID NO. 61
>118.46 eIF2 γ\(AspeIF2-F) eIF2 γ sequence generated
for *A. terreus*
AGGACTCTGCTCTTCCCCCCCAGCCGAAGCGCCCAGAGCTTCCTGAACAACCCAACCCAG

ACACCCTCGATCTGTCGACGCTTACCCCTCTGTCGCCCGAAATCATTGCGCGCCAGGC

CACCATCAACATCGGTACCATTGGTCACGTCGCTCACGGAAAGTCGACGGTCGTCAA

GGCCATCTCAGAGGTCCAGACCGTTCGATTCAAGAACGAGTTGGAGCGTAACATTAC

SEQ ID NO. 62:
>T2729\(AspEF-F) sequence generated for *A. terreus*
AGCCGAAGCGCCCAGAGCTTCCTGAACAACCCAACCCAGACACCCTCGATCTGTCG

ACGCTTACCCCTCTGTCGCCCGAAATTATTGCGCGCCAGGCCACCATCAACATCGGT

ACCATTGGTCACGTCGCTCACGGAAAGTCGACGGTTGTCAAGGCCATCTCAGAGGT

CCAGACCGTTCGATTCAAGAACGAGTTGGAGCGTAACATTAC

SEQ ID NO. 63:
>T601-65\(AspEF-F) sequence generated for *A. terreus*
AGCCGAAGCGCCCAGAGCTTCCTGAACAACCCAACCCAGACACCCTCGATCTGTCG

ACGCTTACCCCTCTGTCGCCCGAAATTATTGCGCGCCAGGCCACCATCAACATCGGT

ACCATTGGTCACGTCGCTCACGGAAAGTCGACGGTTGTCAAGGCCATCTCAGAGGT

CCAGACCGTTCGATTCAAGAACGAGTTGGAGCGTAACATTAC

SEQ ID NO. 64:
>T5677\(AspEF-F) sequence generated for *A. terreus*
AGCCGAAGCGCCCAGAGCTTCCTGAACAACCCAACCCAGACACCCTCGATCTGTCG

ACGCTTACCCCTCTGTCGCCCGAAATTATTGCGCGCCAGGCCACCATCAACATCGGT

ACCATTGGTCACGTCGCTCACGGAAAGTCGACGGTTGTCAAGGCCATCTCAGAGGT

CCAGACCGTTCGATTCAAGAACGAGTTGGAGCGTAACATTAC

SEQ ID NO. 65:
>FL625-66\(AspEF-F) sequence generated for *A. flavus*
CCCCCTGTTTCTCAGCCCAAGCGGCCAGAGTTGCCCGAACAGCCAGACCCCGCTAC

CCTTGACCTGTCGACCCTGACCCCTCTGTCGCCCGAAATCATTGCGCGCCAGGCCAC

TATTAACATTGGTACCATCGGACACGTCGCTCACGGAAAGTCAACAGTGGTCAAGG

CTATCTCAGAGGTTCAGACTGTCCGTTTCAAAAACGAGTTGGAGCGTAACATTAC

SEQ ID NO. 66:
>FL2008\(AspEF-F) sequence generated for *A. flavus*
CCCCCTGTTTCTCAGCCCAAGCGGCCAGAGTTGCCCGAACAGCCAGACCCCGCTAC

CCTTGACCTGTCGACCCTGACCCCTCTGTCGCCCGAAATCATTGCGCGCCAGGCCAC

TATTAACATTGGTACCATCGGACACGTCGCTCACGGAAAGTCAACAGTGGTCAAGG

CTATCTCAGAGGTTCAGACTGTCCGTTTCAAAAACGAGTTGGAGCGTAACATTAC

SEQ ID NO. 67:
>FL2199\(AspEF-F) sequence generated for *A. flavus*
CCCCCTGTTTCTCAGCCCAAGCGGCCAGAGTTGCCCGAACAGCCAGACCCCGCTAC SEQ ID NO. 68:
>V2916\(AspEF-F) sequence generated for A. versicolor
TCAGCCGAAACGACCAGAGCTACCGGAGCAGCCCAACCCAGACACCCTCGACCTG

ACCACATTAACTCCCCTGTCCCCGGAAATTATTGCCCGCCAGGCCACGATCAACATC

GGCACCATTGGTCACGTCGCTCACGGAAAGTCAACGGTGGTGAAGGCTATCTCAGA

AGTCCAGACTGTCAGATTTAAGAATGAGTTGGAGCGTAACATTAC

SEQ ID NO. 69:
>V1323\(AspEF-F) sequence generated for A. versicolor
TCAGCCGAAACGACCAGAGCTACCGGAGCAGCCCAACCCAGACACCCTCGACCTG

ACCACATTAACTCCCCTGTCCCCGGAAATTATTGCCCGCCAGGCCACGATCAACATC

GGCACCATTGGTCACGTCGCTCACGGAAAGTCAACGGTGGTGAAGGCTATCTCAGA

AGTCCAGACTGTCAGATTTAAGAATGAGTTGGAGCGTAACATTAC

SEQ ID NO. 70:
>N100-2\(AspEF-F) sequence generated for A. nidulans
ACGACCGGAACTACCGGAGCAACCCAACCCAGAAACGCTCGACCTGTCTACACTAA

CTCCTCTGTCACCTGAGATTATCGCCCGCCAGGCTACGATTAACATCGGTACCATTG

GCCACGTCGCTCACGGTAAGTCAACGGTGGTGAAGGCTATTTCAGAGGTTCAAACT

GTCCGATTTAAGAACGAGTTGGAGCGTAACATTAC

SEQ ID NO. 71:
>N589-65\(AspEF-F) sequence generated for A. nidulans
ACGACCGGAACTACCGGAGCAACCCAACCCAGAAACGCTCGACCTGTCTACACTAA

CTCCTCTGTCACCTGAGATTATCGCCCGCCAGGCTACGATTAACATCGGTACCATTG

GCCACGTCGCTCACGGTAAGTCAACGGTGGTGAAGGCTATTTCAGAGGTTCAAACT

GTCCGATTTAAGAACGAGTTGGAGCGTAACATTAC

SEQ ID NO. 72:
>N6365\(AspEF-F) sequence generated for A. nidulans
TTCATACCTGTTTCTCAGCCGAAACGACCGGAACTACCGGAGCAACCCAACCCAGA

AACGCTCGACCTGTCTACACTAACTCCTCTGTCACCTGAGATTATCGCCCGCCAGGC

TACGATTAACATCGGTACCATTGGCCACGTCGCTCACGGTAAGTCAACGGTGGTGA

AGGCTATTTCAGAGGTTCAAACTGTCCGATTTAAGAACGAGTTGGAGCGTAACATTAC

SEQ ID NO. 73:
>N670-78\(AspEF-F) sequence generated for A. nidulans
TTCATACCTGTTTCTCAGCCGAAACGACCGGAACTACCGGAGCAACCCAACCCAGA

AACGCTTGACCTGTCTACACTAACTCCTTTGTCACCTGAGATTATCGCCCGCCAGGC

TACGATTAACATCGGTACCATTGGTCACGTCGCTCACGGTAAGTCAACGGTGGTGA

AGGCTATTTCAGAGGTTCAAACTGTCCGATTTAAGAACGAGTTGGAGCGTAACATTAC

SEQ ID No 74:
>gi|68470315|ref|XM_715569.1| Candida albicans SC5314
putative translation initiation factor eIF2 gamma subunit
(CaO19_11699), mRNA
ATGTCATACGACGATATAGAAAATGCCACTCCTGATATTGTTATTGGGAGTACTATA

GAGGAACCTGAAGAAGATTACCAAGTGGAAAGTGACAATGAGTTACAAGCCGCAG

ACCATGAGTCATCGCAAATAAATGAAGAATCAGCCAAAGGCAAAAAGTCAGTTGC

ATTTACTGGATTGGATGAAGACGAGGAAAATGCAGAGGAATTGGCCAGAAAGGAG

TTTGAAGAAGGTGGTGGATTGCCTGAACAACCAGAAAACCCAGATTTCAATGAGTT

-continued

AACACCTTTATCTCCCGAGATTATCAACAGGCAAGCCACCATTAATATTGGTACCAT

TGGTCATGTCGCCCACGGGAAGTCTACTGTTGTCAGGGCTATCTCTGGTGTCCAGAC

CGTTCGTTTCAAGGATGAATTAGAAAGAAACATTACTATCAAGTTAGGTTACGCCA

ATGCCAAAATTTACAAATGTGATAACCCAGAGTGTCCAGAACCAGATTGTTACAGA

TCATTCAAATCAGATAAGGAAATAAGACCAAAATGTCAAAGAGCTGGCTGTGACG

GTCGCTACAAATTGTTAAGACATGTCTCTTTTGTTGATTGTCCAGGACATGATATTT

TGATGAGTACTATGTTGTCAGGTGCTGCCGTGATGGATGCCGCCTTGTTGTTGATTG

CCGGTAATGAAAGTTGTCCACAACCCCAGACTTCTGAGCATTTGGCTGCCATTGAA

ATTATGAAATTGAAACATGTTATTATTTTGCAAAATAAAGTTGATTTGATGAGAGA

AGAATCAGCCTTGGAACACGAAAAATCTATCATTCAGTTTATTAGAGGTACAATTG

CCGATAATGCTCCGATCGTGCCTATTTCTGCTCAATTGAAATACAACATTGATGCAG

TGAATCAATTTATTGTTAACTACATACCTGTGCCAATGAGAGACTTTACTGCTTCAC

CAAGATTGATCGTTATCAGATCTTTCGATGTGAACAAGCCTGGTGCAGATGTAGAC

GAATTGAAAGGAGGTGTTGCAGGTGGTTCTATTTTGACTGGTGTTTTTAAGATTGGT

GATGAGATCGAGATTAGACCTGGTATCGTCACCAAAGATGATCAAGGAAAGATTCA

ATGTAAACCTATATTCTCGAACGTGGTTTCCTTGTTTGCTGAGCATAACGATTTGAA

ATTTGCTGTTCCTGGTGGTTTGATTGGTGTTGGTACTAAAGTTGATCCTACGTTGTGT

AGGGCTGATAGATTGGTTGGTCAAGTTGTTGGTGCAAAAGGAAACTTGCCCTCTAT

TTACGCTGATATTGAGATAAACTATTTCCTATTAAGAAGATTGTTGGGTGTCAAAAC

TGAAGGTCAAAAGCAAGGTGCTAAAGTTCGTAAGTTGGAACAATCTGAAGTGTTGA

TGGTAAATATTGGTTCTACTGCAACTGGTGCTAGAGTGGTTGCTGTTAAAGCAGATA

TGGCTCGTTTACAATTGACTACACCAGCCTGTACAGAAATCAACGAAAAAATTGCG

TTGTCTAGACGTATTGAAAAGCATTGGCGTTTGATTGGTTGGGCCACTATCAAGAA

AGGTACAGCATTAGAACCAATTTCTTAA

SEQ ID NO 75:
>gi|68470576|ref|XM_715441.1| Candida albicans SC5314 translation initiation factor eIF2 gamma subunit CaO19_4223) partial mRNA
ATGTCATACGACGATATAGAAAATGCCACTCCTGATATTGTTATTGGGAGTACTATA

GAGGAACCTGAAGAAGATTACCAAGTGGAAAGTGACAATGAGTTACAAGCCGCAG

ACCATGAGTCATCGCAAATAAATGAAGAATCAGCCAAAGGCAAAAAGTCAGTTGC

ATTTACTGGATTGGATGAAGACGAGGAAAATGCAGAGGAATTGGCCAGAAAGGAG

TTTGAAGAAGGTGGTGGATTGCCTGAACAACCAGAAAACCCAGATTTCAATGAGTT

AACACCTTTATCTCCCGAGATTATCAACAGGCAAGCCACCATTAATATTGGTACCAT

TGGTCATGTCGCCCACGGGAAGTCTACTGTTGTCAGGGCTATCTCTGGTGTCCAGAC

CGTTCGTTTCAAGGATGAATTAGAAAGAAACATTACTATCAAGTTAGGTTACGCCA

ATGCCAAAATTTACAAATGTGATAACCCAGAGTGTCCAGAACCAGATTGTTACAGA

TCATTCAAATCAGATAAGGAAATAAGACCAAAATGTCAAAGAGCTGGCTGTGACG

GTCGCTACAAATTGTTAAGACATGTCTCTTTTGTTGATTGTCCAGGACATGATATTT

TGATGAGTACTATGTTGTCAGGTGCTGCCGTGATGGATGCCGCCTTGTTGTTGATTG

CCGGTAATGAAAGTTGTCCACAACCCCAGACTTCTGAGCATTTGGCTGCCATTGAA

ATTATGAAATTGAAACATGTTATTATTTTGCAAAATAAAGTTGATTTGATGAGAGA

AGAATCAGCCTTGGAACACGAAAAATCTATCATTCAGTTTATTAGAGGTACAATTG

-continued

```
CCGATAATGCTCCGATCGTGCCTATTTCTGCTCAATTGAAATACAACATTGATGCAG

TGAATCAATTTATTGTTAACTACATACCTGTGCCAATGAGAGACTTTACTGCTTCAC

CAAGATTGATCGTTATCAGATCTTTCGATGTGAACAAGCCTGGTGCAGATGTAGAC

GAATTGAAAGGAGGTGTTGCAGGTGGTTCTATTTTGACTGGTGTTTTTAAGATTGGT

GATGAGATCGAGATTAGACCTGGTATCGTCACCAAAGATGATCAAGGAAAGATTCA

ATGTAAACCTATATTCTCGAACGTGGTTTCCTTGTTTGCTGAGCATAACGATTTGAA

ATTTGCTGTTCCTGGTGGTTTGATTGGTGTTGGTACTAAAGTTGATCCTACGTTGTGT

AGGGCTGATAGATTGGTTGGTCAAGTTGTTGGTGCAAAAGGAAACTTGCCCTCTAT

TTACGCTGATATTGAGATAAACTATTTCCTATTAAGAAGATTGTTGGGTGTCAAAAC

TGAAGGTCAAAAGCAAGGTGCTAAAGTTCGTAAGTTGGAACAATCTGAAGTGTTGA

TGGTAAATATTGGTTCTACTGCAACTGGTGCTAGAGTGGTTGCTGTTAAAGCAGATA

TGGCTCGTTTACAATTGACTACACCAGCCTGTACAGAAATCAACGAAAAAATTGCG

TTGTCTAGACGTATTGAAAAGCATTGGCGTTTGATTGGTTGGGCCACTATCAAGAA

AGGTACAGCATTAGAACCAATTTCTTAA

SEQ ID NO 76:
>gi|50290356|re|XM_447610.1| Candida glabrata CBS138
hypothetical protein(CAGL0I08327g) partial mRNA
ATGTCTGATTTGCAAGATCAAGAGCCAACTATTATTATCAATGGTGATCTTCCACCA

GTAGAAGAAGAGGAAGTCTATGAGCAGGAAGAGCAAGAGGAAGTTGTTGAGGAGA

AGCCAAAGAAGAAAGTTGCCTTTACCGGTCTAGAGGATGGTGAATCTGAGGAAGA

GAAGAGAAAGAGAGAGTTTGAAGAAGGTGGTGGATTGCCAGAGCAGCCAGAAAAC

CCAGACTTTACTAAGTTGAACCCACTTTCTGCTGAGATTATTAACAGACAAGCTACT

ATCAACATCGGTACTATTGGTCATGTCGCTCACGGTAAGTCTACTGTTGTCAGAGCC

ATCTCTGGTGTCCAAACCGTTCGTTTCAAGGATGAGTTGGAACGTAACATTACTATC

AAGCTGGGTTATGCCAATGCTAAGATATATAAGTGTCAAGAGCCTACATGTCCAGA

ACCAGACTGTTACAGATCTTTCAAGTCTGACAAAGAAATTAATCCAAAGTGTCAAA

GACCAGGTTGCCCAGGCCGTTACAAACTTGTTCGTCACGTCTCTTTCGTCGATTGTC

CAGGTCACGATATTCTAATGAGTACTATGTTGTCCGGTGCCGCTGTCATGGACGCAG

CCTTGTTATTGATCGCCGGTAATGAATCTTGTCCACAACCTCAAACTTCTGAACATT

TGGCTGCCATTGAAATCATGAAGTTAAAGCACGTTATTATTCTACAGAACAAGGTC

GATTTAATGCGTGAAGAAAGCGCACTAGAACATGAAAAGTCTATCCTGAAATTTAT

CAGAGGTACTATTGCTGACGGTGCTCCAATTGTCCCAATTTCCGCTCAATTGAAATA

CAACATCGATGCAGTCAATGAATTTATCGTGAAGACTATCCCTGTTCCACCAAGAG

ATTTCATGCTTTCTCCACGTTTGATTGTCATTCGTTCTTTCGATGTTAACAAGCCAGG

TGCTGAAATCGATGATTTGAAGGGTGGTGTTGCAGGTGGTTCCATCTTGAACGGTGT

GTTCAAGTTGGGTGATGAGATTGAAATTAGACCAGGTATTGTCACTAAGGATGATA

AGGGTAAGATCCAATGTAAGCCAATTTTCTCCAACATTGTCTCTCTATTTGCTGAAC

AAAATGACTTGAAGTTTGCAGTCCCAGGTGGTCTGATTGGTGTTGGTACAAAGGTC

GATCCTACCTTATGTAGAGCTGATCGTCTTGTCGGTCAAGTTGTCGGTGCCAAGGGT

CACCTACCAAGCATTTACACAGATATTGAAATCAACTACTTCCTACTGCGTCGTCTA

TTAGGTGTTAAGACTGAGAAACAAGCCAAGGTCAGAAAGCTGGTTGCCAACGAAG

TTCTTATGGTTAACATTGGTTCTACTGCCACTGGTGCCCGTGTCGTTGCTGTCAAGG
```

CTGATATGGCTAGATTGCAACTAACATCCCCAGCATGTACAGAAATCAATGAAAAG

ATTGCTCTCTCTAGACGTATTGACAAGCACTGGCGTTTAATTGGTTGGGCTACAATC

AAGAAAGGTACCACTTTGGAACCAGTTGTCTAA

SEQ ID NO. 77:
>XM_746974.2_ Published eIF2 γ sequence for *A. fumigatus*:
*Aspergillus fumigatus* Af293 translation initiation
factor EF-2 gamma subunit (AFUA_4G07580), partial mRNA
ATGGCTACCAACGGCGATTTTACCGACGATGAATCGCAGCCTGGCTCTCCCATGTTG

GATGCGGCGAACGGCCAGGATGATATTGAAGAACAGGAACGTCTTGACGTGGAAG

AGAAGCCCCTTAAGTCTGCGATGAAGAAAGGTGCAGCGCCCCTGCTCCTCAGCCG

AAGCGTCCAGAACTCCCCGAGCAGCCCGACCCAGAGACTCTCGATTTGTCGACGCT

CACACCTCTGTCGCCCGAAATTATTGCGCGCCAGGCCACAATCAACATCGGTACTA

TCGGACACGTCGCACACGGCAAGTCGACTGTTGTGAAGGCTATCTCGGAGGTGCAG

ACTGTCCGGTTCAAAAATGAGTTGGAGCGTAACATTACCATCAAGCTTGGTTATGC

CAACGCGAAGATCTACAAGTGCGACAACCCTGGGTGCCCGCGCCCGACGTGCTTCA

AGAGTTACAAGAGTGAGAAGGAGATCGACCCTCCATGTGAGAGAGAAGGATGCAC

AGGTCGTTACAGATTGTTGAGACATGTCTCGTTCGTTGACTGCCCTGGGCACGATAT

TCTCATGAGTACCATGTTGTCAGGTGCCGCCGTCATGGACGCCGCCCTTTTGCTGAT

TGCCGGAAACGAAGCTTGCCCCCAGCCTCAGACTTCGGAGCACTTAGCAGCTATTG

AAATCATGAAGCTCAGCCATATCATCATTCTGCAGAACAAGGTTGATCTGATGAGG

GAAGACGGTGCTCTGCAACATTACCAATCAATCCTGAAGTTCATTCGTGGTACTGTT

GCCGATGGCTCTCCTATCATTCCCATCTCTGCTCAGCTCAAGTACAACATCGACGCT

GTCAACGAATACCTTGTCTCGCACATCCCAGTTCCCGTCCGTGACTTCACTGCTTCG

CCTCACATGATTGTCATTCGTTCCTTCGACGTCAACAAACCCGGTGCGGAGATCGAT

GAGTTGAAGGGTGGTGTTGCAGGTGGCTCTATCCTCACTGGTGTGCTGAAGCTGAA

CGACGAGATTGAAATTCGCCCCGGTCTCGTTACCAAGGATGAGAACGGAAAGATTC

AGTGCCGCCCCATCTTCTCCCGTGTCGTCTCGCTCTTCGCTGAGCACAACGATCTGA

AGTTCGCTGTCCCTGGTGGTCTAATCGGTGTCGGAACCCGTGTCGACCCTACCCTGT

GCCGTGCCGATCGTCTTGTTGGTTTCGTCCTGGGTCACCGTGGCCGTTTGCCAGCCA

TCTACACTGAACTGGAGGTCAACTACTTCCTCCTGCGTCGTCTGCTCGGTGTCAAGA

CCGCCGACGGCAAGCAGGCCAAGGTCGCCAAGCTCACCAAGAACGAAGTCCTCAT

GGTTAACATCGGCTCTACGGCTACTGGTGCTAAGGTTATGGGTGTGAAGGCTGATG

CTGCCAAGCTCAGCTTGACCAGCCCGGCTTGTACAGAGATTGGAGAGAAGATTGCT

ATCAGCCGGAGAATTGACAAGCATTGGCGTCTGATCGGCTGGGCCAACATTGTCGC

TGGCAACACTCTTGAGCCCATTCTGAACTAG

SEQ ID NO. 78:
>XM_001267265.1_ Published eIF2 sequence for *N. fischeri*:
*Neosartorya fischeri* NRRL 181 translation initiation factor
EF-2 gamma subunit, putative (NFIA_108620) partial mRNA
ATGGCTACCAACGGCGATTTTACCGACGATGAATCGCAGCCTGGCTCTCCCATGCT

GGATGCGGCGAACGGCCAGGATGACATTGAAGAACAGGAGCCTCTTGACGTGGAA

GAGAAGCCCCTCAAGTCTGCAATGAAGAAAGGTTCAGCGCCCCCTGCTCCTCAGCC

GAAGCGTCCAGAACTCCCCGAGCAGCCCGACCCAGAGACTCTCGAATTGTCGACAC

TCACGCCTCTGTCGCCCGAGATTATTGCGCGCCAGGCCACAATCAACATCGGTACT

-continued

```
ATCGGACACGTCGCTCACGGCAAGTCGACTGTGGTGAAGGCTATTTCGGAGGTGCA

GACTGTCCGGTTCAAAAATGAGTTGGAGCGTAATATTACCATCAAGCTTGGTTATG

CCAACGCGAAGATCTACAAGTGCGACAACCCTGAGTGCCCGCGCCCGACGTGCTTC

AAGAGTTACAAGAGTGAGAAGGAGATCGACCCTCCATGTGAGAGAGAAGGATGCA

CAGGTCGTTACAGATTGTTGAGACATGTCTCGTTCGTTGACTGCCCTGGGCACGATA

TTCTCATGAGTACCATGTTGTCAGGTGCCGCCGTCATGGACGCCGCCCTTTTGCTGA

TTGCCGGAAACGAAGCTTGCCCCCAGCCTCAGACTTCGGAGCACTTGGCAGCTATT

GAAATCATGAAGCTCAGCCACATCATCATTCTGCAGAACAAGGTTGATCTGATGAG

GGAAGACGGTGCTCTTCAACATTACCAATCAATCCTGAAGTTCATTCGTGGTACTGT

TGCCGATGGTTCTCCTATCATTCCCATCTCTGCTCAGCTCAAGTACAACATCGACGC

TGTCAACGAATACCTTGTCTCGCACATCCCAGTTCCCGTCCGTGACTTCACTGCTTC

GCCTCACATGATTGTCATCCGTTCCTTCGACGTCAACAAGCCCGGTGCGGAGATCG

ATGAGTTGAAGGGTGGTGTTGCAGGTGGCTCTATCCTCACTGGTGTGCTGAAGCTG

AACGACGAGATTGAGATTCGCCCCGGTCTCGTTACCAAGGATGAGAACGGAAAGAT

TCAGTGCCGCCCCATCTTCTCCCGTGTCGTTTCGCTCTTCGCTGAGCACAACGATCT

GAAGTTCGCTGTCCCTGGTGGTCTGATCGGTGTCGGAACCCGTGTCGACCCTACCCT

GTGCCGTGCCGATCGTCTCGTTGGTTTCGTCCTGGGTCACCGTGGCCGTTTGCCGGC

CATCTACACTGAACTGGAGGTCAACTACTTCCTCCTGCGTCGTCTGCTCGGTGTCAA

GACCGCCGACGGCAAGCAGGCCAAGGTCGCCAAGCTCACCAAGAACGAGGTCCTC

ATGGTTAACATCGGCTCTACGGCTACTGGTGCTAAGGTTATGGGTGTGAAGGCTGA

TGCTGCCAAGCTCAGCTTGACCAGCCCGGCTTGTACAGAGATTGGAGAGAAGATTG

CTATCAGCCGGAGAATTGACAAGCATTGGCGTCTGATCGGCTGGGCCAATATTGTC

GCTGGCAACACTCTTGAGCCCATTCTGAACTAG
```

SEQ ID NO. 79:
>XM_001271648.1_ Published eIF2 γ sequence for A. clavatus:
Aspergillus clavatus NRRL 1 translation initiation factor
EF-2 gamma subunit, putative (ACLA_046890), partial mRNA

```
ATGGGTCATTATGAAATTGAAGAACAAGAGCCTCTTGATGTCGAGGAGAAGGCCCT

CAAGTCTTCGATGAAGAAGGGCTCCATGCCCCCAGTTCCTCAACCGAAGCGCCCAG

AACTGCCCGAGCAGCCTGACCCAGAGACCATCGATCTGTCGAAACTGACGCCTCTG

TCCCCCGAAATTATCGCGCGCCAGGCCACGATCAACATTGGTACCATCGGACACGT

CGCTCACGGCAAGTCGACCGTGGTGAAGGCTATCTCGGAGGTGCAGACGGTCCGTT

TCAAGAACGAGTTGGAGCGGAATATTACCATCAAGCTGGGTTATGCCAACGCCAAG

ATCTACAAGTGCGACAGCCCTGAGTGCCCTCGGCCGACATGCTACAAGAGTTACAA

GAGTGAGAAGGAGGTCGACCCTCCTTGCGAAAGAGAAGGATGCACAGGTCACTAC

AGACTGCTGAGACACGTTTCTTTCGTTGACTGCCCCGGTCACGACATTCTCATGAGC

ACTATGTTGTCAGGCGCCGCCGTCATGGACGCCGCCCTTCTTTTGATTGCCGGAAAC

GAAGCCTGCCCTCAGCCCCAGACCTCGGAGCACTTGGCAGCCATTGAGATCATGAA

GCTCAGCCACATTATCATCCTGCAGAACAAGGTCGATCTGATGAGAGAGGATGGAG

CTTTGCAACATTACCAGTCGATTCTGAAGTTCATCCGTGGTACTGTCGCTGATGGCT

CGCCCATCATTCCTATCTCTGCGCAGCTCAAGTACAACATTGATGCTGTTAACGAAT

ACCTTGTTTCGCACATCCCCGTCCCCGTCCGTGACTTCACTGCTTCCCCTCACATGAT

CGTCATCCGTTCCTTCGACGTCAACAAGCCCGGTGCGGAGATTGATGAGCTGAAGG
```

-continued

```
GTGGTGTTGCCGGTGGCTCTATCCTGACTGGTGTGCTCAAGTTGAATGATGAGATCG

AGATCCGCCCTGGTCTCGTTACCAAGGACGAGAACGGCAAGATTCAGTGCCGTCCC

ATCTTCTCGCGTGTTGTCTCGCTCTTTGCCGAGCACAACGACCTGAAGTTTGCTGTT

CCTGGTGGTCTGATCGGTGTCGGCACCCGTGTCGACCCTACTCTGTGCCGTGCTGAT

CGTCTCGTTGGTTTCGTCCTGGGTCACCGTGGTCGCCTGCCCGCTATTTACACTGAA

CTGGAGGTCAACTACTTCTTGCTGCGTCGTCTGCTCGGTGTCAAGACCGCCGATGGC

AAGCAGGCTAAGGTTGCCAAGCTGACCAAGAACGAGGTTCTCATGGTCAACATCGG

ATCGACAGCCACTGGTGCCAAGGTTATGGGTGTGAAGGCCGACGCTGCCAAGCTCA

GCTTGACCAGCCCTGCCTGCACAGAAATTGGCGAGAAGATTGCCATCAGCCGAAGA

ATCGACAAGCATTGGCGTCTGATCGGTTGGGCCAACATTGTCGCTGGTAACACTCTT

GAGCCTATTCTGAACTAG
```

SEQ ID NO. 80:
>XM_001214623.1_ Published eIF2 sequence for A. terreus
```
ATGGCTACCAACGGCGATTTCACCGACGATGAATCCCAGCCCGGTTCCCCCGTCAT

GGAGCCCAACGGCCAGTACGACATTGAAGAACAGGAGCCTCTCGACCAGCCCCTG

AAGTCGGCGATGAAGAAGGACTCTGCTCTTTCCCCCAGCCGAAGCGCCCAGAGCT

TCCTGAACAACCCAACCCAGACACCCTCGATCTGTCGACGCTTACCCCTCTGTCGCC

CGAAATTATTGCGCGCCAGGCCACCATCAACATCGGTACCATTGGTCACGTCGCTC

ACGGAAAGTCGACGGTTGTCAAGGCCATCTCAGAGGTCCAGACCGTTCGATTCAAG

AACGAGTTGGAACGGAATATTACGATTAAGCTGGGTTATGCCAACGCCAAGATCTA

CAAGTGCGACAACCCCGAGTGCCCTCGGCCGACTTGTTACAAGAGTTTCAAGAGTG

AGAAGGAGGTCGACCCGCCATGTGAGAGAGATGGCTGCACAGGTCGTTACCGTCTA

CTGAGACACGTCTCCTTTGTCGACTGCCCCGGTCACGATATTCTCATGAGTACCTGT

TGTCTGGTGCCGCCGTCATGGACGCTGCCCTTCTCCTGATTGCCGGAAACGAAACCT

GCCCCCAGCCTCAGACCTCGGAGCACTTGGCTGCTATTGAGATCATGAAGCTGAGT

CATATCATTATCCTGCAGAACAAGGTCGATCTGATGCGCGAGGACGGTGCCCTGCA

GCACTACCAGTCGATCCTGAAGTTCATCCGTGGTACTGTGGCAGACGGCTCTCCCAT

TATCCCCATCTCCGCCCAGCTGAAGTACAACATCGATGCGGTCAACGAGTACCTCG

TGTCGCACATCCCCGTCCCCGTCCGTGACTTTACCGCCTCTCCTCACATGATTGTCAT

TCGCTCCTTCGACGTCAACAAGCCCGGTGCCGAGATTGATGATCTGAAGGGTGGTG

TCGCTGGTGGTTCCATCCTGACAGGTGTGCTGAAGCTGAACGACGAGATCGAAATC

CGTCCCGGTCTGGTCACGAAGGACGAGAACGGCAAGATCCAGTGCCGTCCCATCTT

CTCTCGCGTGGTCTCCCTATTCGCCGAGCACAACGACCTCAAGTTCGCGTGCCCGGC

GGTCTTATCGGTGTTGGTACTCGCGTTGACCCTACCCTCTGCCGTGCGGATCGTCTT

GTTGGTTTCGTCCTGGGTCACCGTGGTCGCCTGCCTGCTATCTACACTGAGCTGGAG

GTTAACTACTTCTTGCTGCGTCGTCTGCTCGGTGTGAAGACCGCCGACGGAAAGCA

GGCTAAGGTCGCCAAGCTGGCCAAGAACGAAGTTCTGATGGTGAACATTGGATCTA

CGGCCACCGGTGCCAAGGTGATGGGTGTGAAGGCTGATGCTGCCAAGCTCAGCTTG

ACCAGCCCTGCCTGTACCGAGATCGGAGAGAAGATCGCCATCAGTCGGAGAATTGA

GAAGCACTGGCGTCTGATCGGTTGGGCCAACATTGTTGCCGGTAACACCCTGGAGC

CCATCCTGAACTAA
```

SEQ ID NO. 81:
>gi|169773704|ref|XM_001821269.1| *Aspergillus oryzae*
RIB40 hypothetical protein partial mRNA
ATGGCTGCCAACGGCGATTTTTCCGATGATGAATCCCAGCCGGGATCCCCCATGCT

GAATGCGAACGGCCATGATGATATTGAAGAACAAGAGCCCCTCGACCAAGAGGAG

AAGCCTCTCAAGTCTGCGATGAAGAGTGTACCCCTGTTTCTCAGCCCAAGCGGCC

AGAGTTGCCCGAACAGCCAGACCCCGCTACCCTTGACCTGTCGACCCTGACCCCTCT

GTCGCCCGAAATCATTGCGCGCCAGGCCACTATTAACATTGGTACCATCGGACACG

TCGCTCACGGAAAGTCAACAGTGGTCAAGGCTATCTCAGAGGTTCAGACTGTCCGT

TTCAAAAACGAGTTGGAGCGAAACATTACAATCAAGCTGGGCTACGCCAACGCCAA

GATCTACAAGTGCGACAACCCCGAGTGTCCTCGCCCAACATGCTTCAAGAGTTTCA

AGAGTGAGAAGGAGATCGACCCTCCATGTGAGAGAGATGGGTGCACAGGACGTTA

TAGGCTGTTGAGACATGTCTCCTTCGTTGACTGCCCCGGTCACGATATTCTGATGAG

TACCATGTTGTCAGGTGCCGCCGTCATGGACGCAGCTCTTCTTCTGATTGCCGGAAA

CGAAACTTGCCCTCAGCCTCAAACCTCGGAACATTTGGCAGCTATCGAGATTATGA

AGCTTAGCCATATTATCATCTTGCAAAATAAGGTTGATCTGATGAGGGAAGAAGGA

GCTTTTCAGCATTACCAATCGATTCTGAAGTTCATCCGTGGTACTGTTGCTGATGGC

TCTCCTATTATCCCCATCTCCGCTCAGCTGAAGTACAACATTGATGCTGTCAAC

GAATACCTTGTTTCCCACATCCCTGTCCCTGTCCGTGATTTCACCGCTTCGCCACAC

ATGATCGTCATCCGTTCATTCGATGTGAACAAGCCTGGTGCCGAGATTGATGAGCT

GAAGGGCGGTGTTGCTGGTGGTTCCAT

TCTGACTGGTGTGCTTAAGCTTAACGACGAGGTGGAAATCCGTCCCGGTCTCGTAA

CCAAGGACGAGAACGGCAAGATTCAGTGCCGGCCCATCTTCTCGCGGGTTGTTTCT

CTCTTCGCTGAGCACAACGACCTGAAATTTGCTGTTCCTGGTGGTCTTATTGGTGTC

GGTACCCGTGTGGACCCTACTCTGTGCCGTGCCGATCGTCTTGTCGGTTTCGTCCTG

GGCCATCGCGGACGTCTGCCCGCCATTTACACCGAACTGGAGGTCAACTATTTC

TTGCTGCGCCGGTTGTTGGGTGTGAAGACCGCCGACGGCAAGCAGGCCAAGGTTGC

TAAGCTGAGCAAGAACGAGGTTCTGATGGTCAACATCGGTTCTACGGCCACCGGTG

CTAAGGTCATGGGCGTCAAGGCCGATGCTGCAAAGCTGAGCTTGACCAGCCCTGCT

TGTACCGAAATTGGCGAGAAGATTGCCATTTCTCGCAGAATCGACAAGCACTGGCG

TCTGATTGGGTGGGCTAACATTGTTGCCGGTAACACCCTCGAACCCATCCTGAACTAA

SEQ ID NO. 82:
>XM_001401525.1_ Published eIF2γ sequence for *A. niger*
ATGGCTGACGATGACATCGAAGAGCAAGAGCCCCTCGACCAGGAGGCCAAGCCTC

TGAAGTCTGCGATGAAGAAGGAAGTTCCTCCTCCCCAGCCCAAGCGGCCAGAGCTG

CCCGAGCAGCCGAATCCGGAGACTCTGGACCTGTCCACCCTGACTCCTTTGACCCCC

GAAATTATTGCGCGCCAAGCCACAATCAACATTGGCACCATCGGTCACGTCGCTCA

CGGCAAGTCGACGGTCGTTAAGGCTATCTCCGAGGTCCAGACTGTCCGTTTCAAGA

ACGAGTTGGAGCGAAACATTACGATCAAGCTGGGTTATGCCAACGCAAAGATCTAC

AAGTGCGACAACCCCGAGTGCCCTAGGCCGACATGCTTTAAGAGCTTTAAGAGTGA

GAAGGAAGTCGACCCGCCTTGTGAGAGGGATGGCTGCGGTGGCCGCTACAGACTGT

TGAGACATGTGTCTTTCGTCGACTGCCCCGGTCACGATATTCTGATGAGTACATGT

TGTCTGGTGCCGCCGTCATGGACGCTGCCCTCCTCCTTATTGCCGGAAACGAAACTT

-continued

```
GCCCTCAACCTCAGACTTCGGAGCACTTGGCTGCCATCGAAATCATGAAGCTCAGC
CACATCATCATTTTGCAAAACAAGGTGGACTTGATGAGAGAGGATGGTGCCCTGCA
ACATTACCAGTCGATCTTGAAGTTCATCCGTGGTACTGTCGCCGATGGCTCTCCGAT
CATTCCCATTTCTGCACAGCTCAAGTACAACATCGATGCTGTCAACGAATACCTGGT
TTCGCACATTCCCGTCCCCGTCCGCGATTTCACCGCTTCCCCCCACATGATCGTCATT
CGTTCCTTCGATGTGAACAAGCCTGGTGCCGAAATTGAGGAGCTGAAGGGTGGTGT
TGCCGGTGGTTCGATCTTGACTGGTGTTCTGAAGCAGAACGACGAGATTGAGATTC
GTCCCGGTCTGGTCACCAAGGACGAGAACGGCAAGATTCAGTGCCGTCCCATCTTC
TCTCGGGTCATGTCCCTCTTTGCCGAGCACAACGACCTCAAGTTTGCCGTCCCTGGT
GGTTTGATTGGTGTCGGTACTCGTGTAGACCCTACTCTGTGCCGTGCTGATCGTCTC
GTTGGTTTCGTCCTGGGTCACCGCGGACGCCTTCCCGCTATCTACACTGAGTTGGAA
GTCAACTACTTCTTGCTTCGTCGTCTGCTCGGTGTCAAGACTGCCGATGGCAAGCAG
GCCAAGGTTGCCAAGCTTACTAAGAACGAGGTTCTCATGGTCAACATCGGTTCTAC
GGCTACCGGAGCTAAGGTCGTGGGTGTCAAGGCTGATGCTGCCAAGCTCAGCTTGA
CCAGCCCTGCCTGTACCGAGGTCGGAGAGAAGATTGCCATCAGTCGGAGAATTGAG
AAGCACTGGCGTCTGATCGGTTGGGCCAACATTGTCGCTGGTAACACCCTTGAGCC
CATCCTGAACTAA
```

SEQ ID NO. 83:
>XM_656982.1_ Published eIF2γ sequence for A. nidulans
```
ATGGCTACCAACGGCGATTTTTCAGACGAGGAGTCCCAGCCCGGGTCTCCCATTCTT
AACGCCAATGGCCAGGATGATATCCAAGACCAAGAGCCCCTCGAGCAGGAGGAGA
AGCCCATCAAGTCAGCGATGAAGAAGGACTTCATACCTGTTTCTCAGCCGAAACGA
CCGGAACTACCGGAGCAACCCAACCCAGAAACGCTCGACCTGTCTACACTAACTCC
TCTGTCACCTGAGATTATCGCCCGCCAGGCTACGATTAACATCGGTACCATTGGCCA
CGTCGCTCACGGTAAGTCAACGGTGGTGAAGGCTATTTCAGAGGTTCAAACTGTCC
GATTTAAGAACGAGTTGGAGCGAAACATTACCATCAAGCTGGGTTATGCCAACGCG
AAAATCTACAAGTGCGACAACCCCGCTTGCCCTCGGCCGACATGCTACAAGAGCTA
TAAGAGTGAGAAGGAAATTGATCCGCCCTGTGAGAGAGATGGATGCTCTGGCCGCT
ACCGTCTCTTAAGACACGTTTCCTTCGTCGACTGCCCTGGTCACGACATTCTTATGA
GTACCATGTTGTCAGGTGCCGCTGTCATGGATGCTGCTCTTTTGCTTATCGCTGGAA
ACGAAACCTGTCCTCAGCCCCAGACTTCGGAGCATTTGGCTGCTATTGAAATCATG
AAGCTTAGCCACATCATTATCCTTCAAAACAAGGTCGATTTGATGAGGGAAGATGG
AGCGTTGCAGCATTACCAGTCGATCTTGAAATTTATCCGTGGTACCGTTGCCGACGG
CTCTCCCATCATTCCCATCTCCGCTCAGCTCAAGTACAACATCGATGCCGTCAACGA
GTATCTGGTTTCGCACATCCCCGTGCCAGTCCGCGATTTCACGGCATCTCCTCACAT
GATTGTTATCCGGTCTTTCGACGTGAACAAGCCTGGTGCAGAGATTGATGAGCTAA
AGGGTGGTGTGGCTGGTGGTTCCATTTTGACTGGTGTCCTCAAGTTGAACGATGAA
ATCGAAATTCGACCAGGTCTCGTCACTAAGGACGAGAACGGCAAGATCCAGTGTCG
CCCTATCTTCTCGCGGGTTGTGTCTTTGTTTGCCGAACACAACGACCTGAAATTCGC
TGTCCCCGGTGGATTGATCGGTGTTGGTACTCGTGTTGACCCTACTCTTTGCCGTGC
CGATCGCCTGGTTGGTTTCGTCCTCGGTCACCGTGGGCGCCTTCCCGCTATCTACAC
AGAGCTAGAGGTCAATTACTTTTTGCTGCGCCGACTTTTGGGTGTCAAGACTGCCGA
```

-continued

CGGCAAGCAGGCCAAGGTCGCCAAGCTGGCTAAGAACGAGGTTCTCATGGTTAATA

TCGGCTCTACAGCTACCGGTGCGAAGGTGGTCGGTGTCAAGGCTGATGCTGCTAAG

CTGAGCTTGACTAGCCCAGCCTGTACTGAGGTTGGCGAGAAGATTGCCATTAGTCG

AAGAATTGAGAAGCACTGGCGTTTGATTGGTTGGGCCAACATTGTTGCTGGTAACA

CCCTCGAGCCCATTGTCAACTAA

SEQ ID NO: 84:
ALEF2
ATAATGCTCCGATCGTGCCTA

SEQ ID NO: 85:
GlabA
CAAGAGATTTCATGCTTTCTCCAC

SEQ ID NO: 86:
ParA
CGTAAACTCAATACCAGTTCCAGTC

SEQ ID NO: 87:
TropicA
TGTCAATTATATCCCAGTTCCATTGA

SEQ ID NO: 88:
KrusA
CATGTGTATGGTCAAGTCTATTCCT

SEQ ID NO: 89:
CEF3F
TCAGCCTTGGAACAC

SEQ ID NO: 90:
CEFR1
TTGGCACAGGTATGTAG

SEQ ID NO: 91:
GlabF1
TCgTgAAgACTATCCCTgT

SEQ ID NO: 92:
GlabR1
ATCGATTTCAGCACCTGG

SEQ ID NO: 93:
ParaF1
TATCgACgCCgTCAATC

SEQ ID NO: 94:
ParaR1
ATCAACgTCAgCACCAg

SEQ ID NO: 95:
TropicF1
ACATCGATGCCGTTAACC

SEQ ID NO: 96:
TropicR1
CAAGTCTTCGACATCGGA

SEQ ID NO: 97:
KrusF1
CCCAATTTCTGCTCAGTTG

SEQ ID NO: 98:
KrusR1
CACCAGGCTTATTAACATCG

SEQ ID NO: 99:
The amplified region of interest in eIF2γ of *Candida albicans* (XM_715569.1) is underlined. (Position of the region of interest: 790-934).
ATGTCATACGACGATATAGAAAATGCCACTCCTGATATTGTTATTGGGAGTACTATA

GAGGAACCTGAAGAAGATTACCAAGTGGAAAGTGACAATGAGTTACAAGCCGCAG

ACCATGAGTCATCGCAAATAAATGAAGAATCAGCCAAAGGCAAAAAGTCAGTTGC

-continued

ATTTACTGGATTGGATGAAGACGAGGAAAATGCAGAGGAATTGGCCAGAAAGGAG

TTTGAAGAAGGTGGTGGATTGCCTGAACAACCAGAAAACCCAGATTTCAATGAGTT

AACACCTTTATCTCCCGAGATTATCAACAGGCAAGCCACCATTAATATTGGTACCAT

TGGTCATGTCGCCCACGGGAAGTCTACTGTTGTCAGGGCTATCTCTGGTGTCCAGAC

CGTTCGTTTCAAGGATGAATTAGAAAGAAACATTACTATCAAGTTAGGTTACGCCA

ATGCCAAAATTTACAAATGTGATAACCCAGAGTGTCCAGAACCAGATTGTTACAGA

TCATTCAAATCAGATAAGGAAATAAGACCAAAATGTCAAAGAGCTGGCTGTGACG

GTCGCTACAAATTGTTAAGACATGTCTCTTTTGTTGATTGTCCAGGACATGATATTT

TGATGAGTACTATGTTGTCAGGTGCTGCCGTGATGGATGCCGCCTTGTTGTTGATTG

CCGGTAATGAAAGTTGTCCACAACCCCAGACTTCTGAGCATTTGGCTGCCATTGAA

ATTATGAAATTGAAACATGTTATTATTTTGCAAAATAAAGTTGATTTGATGAGAGA

AGAATCAGCCTTGGAACACGAAAAATCTATCATTCAGTTTATTAGAGGTACAATTG

CCGATAATGCTCCGATCGTGCCTATTTCTGCTCAATTGAAATACAACATTGATGCA

GTGAATCAATTTATTGTTAACTACATACCTGTGCCAATGAGAGACTTTACTGCTTCA

CCAAGATTGATCGTTATCAGATCTTTCGATGTGAACAAGCCTGGTGCAGATGTAGA

CGAATTGAAAGGAGGTGTTGCAGGTGGTTCTATTTTGACTGGTGTTTTTAAGATTGG

TGATGAGATCGAGATTAGACCTGGTATCGTCACCAAAGATGATCAAGGAAAGATTC

AATGTAAACCTATATTCTCGAACGTGGTTTCCTTGTTTGCTGAGCATAACGATTTGA

AATTTGCTGTTCCTGGTGGTTTGATTGGTGTTGGTACTAAAGTTGATCCTACGTTGT

GTAGGGCTGATAGATTGGTTGGTCAAGTTGTTGGTGCAAAAGGAAACTTGCCCTCT

ATTTACGCTGATATTGAGATAAACTATTTCCTATTAAGAAGATTGTTGGGTGTCAAA

ACTGAAGGTCAAAAGCAAGGTGCTAAAGTTCGTAAGTTGGAACAATCTGAAGTGTT

GATGGTAAATATTGGTTCTACTGCAACTGGTGCTAGAGTGGTTGCTGTTAAAGCAG

ATATGGCTCGTTTACAATTGACTACACCAGCCTGTACAGAAATCAACGAAAAAATT

GCGTTGTCTAGACGTATTGAAAAGCATTGGCGTTTGATTGGTTGGGCCACTATCAAG

AAAGGTACAGCATTAGAACCAATTTCTTAA

SEQ ID NO: 100:
The amplified region of interest in eIF2γ of *Candida glabrata* (XM_447610.1) is underlined.
(Position of the region of interest: 872-972).
ATGTCTGATTTGCAAGATCAAGAGCCAACTATTATTATCAATGGTGATCTTCCACCA

GTAGAAGAAGAGGAAGTCTATGAGCAGGAAGAGCAAGAGGAAGTTGTTGAGGAGA

AGCCAAAGAAGAAAGTTGCCTTTACCGGTCTAGAGGATGGTGAATCTGAGGAAGA

GAAGAGAAAGAGAGAGTTTGAAGAAGGTGGTGGATTGCCAGAGCAGCCAGAAAAC

CCAGACTTTACTAAGTTGAACCCACTTTCTGCTGAGATTATTAACAGACAAGCTACT

ATCAACATCGGTACTATTGGTCATGTCGCTCACGGTAAGTCTACTGTTGTCAGAGCC

ATCTCTGGTGTCCAAACCGTTCGTTTCAAGGATGAGTTGGAACGTAACATTACTATC

AAGCTGGGTTATGCCAATGCTAAGATATATAAGTGTCAAGAGCCTACATGTCCAGA

ACCAGACTGTTACAGATCTTTCAAGTCTGACAAAGAAATTAATCCAAAGTGTCAAA

GACCAGGTTGCCCAGGCCGTTACAAACTTGTTCGTCACGTCTCTTTCGTCGATTGTC

CAGGTCACGATATTCTAATGAGTACTATGTTGTCCGGTGCCGCTGTCATGGACGCAG

CCTTGTTATTGATCGCCGGTAATGAATCTTGTCCACAACCTCAAACTTCTGAACATT

-continued

TGGCTGCCATTGAAATCATGAAGTTAAAGCACGTTATTATTCTACAGAACAAGGTC

GATTTAATGCGTGAAGAAAGCGCACTAGAACATGAAAAGTCTATCCTGAAATTTAT

CAGAGGTACTATTGCTGACGGTGCTCCAATTGTCCCAATTTCCGCTCAATTGAAATA

CAACATCGATGCAGTCAATGAATTTA<u>TCGTGAAGACTATCCCTGT</u>TCCACAAGAG

ATTTCATGCTTTCTCCACGTTTGATTGTCATTCGTTCTTTCGATGTTAACAAG<u>CCAG</u>

<u>GTGCTGAAATCGAT</u>GATTTGAAGGGTGGTGTTGCAGGTGGTTCCATCTTGAACGGT

GTGTTCAAGTTGGGTGATGAGATTGAAATTAGACCAGGTATTGTCACTAAGGATGA

TAAGGGTAAGATCCAATGTAAGCCAATTTTCTCCAACATTGTCTCTCTATTTGCTGA

ACAAAATGACTTGAAGTTTGCAGTCCCAGGTGGTCTGATTGGTGTTGGTACAAAGG

TCGATCCTACCTTATGTAGAGCTGATCGTCTTGTCGGTCAAGTTGTCGGTGCCAAGG

GTCACCTACCAAGCATTTACACAGATATTGAAATCAACTACTTCCTACTGCGTCGTC

TATTAGGTGTTAAGACTGAGAAACAAGCCAAGGTCAGAAAGCTGGTTGCCAACGA

AGTTCTTATGGTTAACATTGGTTCTACTGCCACTGGTGCCCGTGTCGTTGCTGTCAA

GGCTGATATGGCTAGATTGCAACTAACATCCCCAGCATGTACAGAAATCAATGAAA

AGATTGCTCTCTCTAGACGTATTGACAAGCACTGGCGTTTAATTGGTTGGGCTACAA

TCAAGAAAGGTACCACTTTGGAACCAGTTGTCTAA

SEQ ID NO: 101:
The amplified region of interest is underlined. (151-274).
>P-604\(EF)\(CaneIF2-F) eIF2 γ sequence generated for
*C. parapsilosis*
GTTGAAGCACGTTATTATTTTGCAAAACAAAGTTGATTTAATGAGAAAGGAGTCAG

CTTTGGAACATGAAAAGTCCATCATTCAGTTCATCAGAGGTACTATAGCTGATGGT

GCCCCAATTGTTCCAATTTCAGCACAATTGAAGTATAA<u>TATCGACGCCGTCAATCAA</u>

<u>TTCATCGTAAACTCAATACCAGTTCCAGTC</u>AGGGACTTTACTGCATCCCCTAGGTT

AATTGTTATTAGGTCTTTTGATGTGAACAAAC<u>CTGGTGCTGACGTTGAT</u>GATTTGAA

AGGAGGTGTTGCAGGTGGTTC

SEQ ID NO: 102
The amplified region of interest is underlined. (140-270).
>T94\(EF)\(CaneIF2-F) eIF2 γ sequence generated for
*C. tropicalis*
GTCATKATTTTGCAGAACAAGGTCGATTTGATGAGAGAAGAATCTGCCTTGGAACA

TGAGAAATCCATTCTTCAATTCATCAGAGGTACTATTGCAGACAATGCTCCTATTGT

CCCAATTTCTGCCCAATTGAAATACA<u>ACATCGATGCCGTTAACC</u>AATTTATTGTCAA

TTATATCCCAGTTCCATTGAGAGACTTTTCCGCTTCCCCAAGATTGATTGTCATCA

GATCTTTTGATGTCAACAAGCCAGGT<u>TCCGATGTCGAAGACTTG</u>AAAGGGGGTGTT

GCAGGTGGTTC

SEQ ID NO: 103:
The amplified region of interest is underlined. (115-224).
>K573E\(EF)\(CaneIF2-F) eIF2 γ sequence generated for
*C. krusei*
TGKTGTGATTKTACAAAATAAAGTTGATTTGATGAAGAAAGAAGCAGCTTTAGAGC

ACGAAAAATCTATTTTGAAGTTTATCAAGGGTACTATTGCTGATGGTGCTCCTATTA

T<u>CCCAATTTCTGCTCAGTTG</u>AAATATAACATTGATGCAGTTAACATGTGTATGGTC

AAGTCTATTCCTGTTCCAATTAGAGACTTTACC<u>GCAGTTCCAAGATTAATGGTTAT</u>

TAGATCTTTCGATGTTAATAAGCCTGGTGCAGAAATTGCAGATTTGAAAGGTGGTG

TTGCAGGTGGTTC

SEQ ID NO: 104:
EF2_7_FOW
AGCCCAAGCGGCCAGA

SEQ ID NO: 105:
EF2_8_FOW
AGCCGAAGCGCCCAGA

SEQ ID NO: 106:
EF2_5_REV
GGCCTGGCGCGCAAT

SEQ ID NO: 107:
EF2_6_REV
GGCTTGGCGCGCAAT

SEQ ID NO: 108:
A.NIG_EF2_1
ATCCGGAGACTCTGGACCT

SEQ ID NO: 109:
A.TERR_EF2_1
CGACGCTTACCCCTCTGT

SEQ ID NO: 110:
A.FLAV_EF2_1
CAGACCCCGCTACCCTT

SEQ ID NO: 111:
A.FUM_EF2_1
ACGCTCACACCTCTGTC

SEQ ID NO: 112:
EF2_9_FOW
AGCCGAAGCGTCCAGAAC

SEQ ID NO: 113:
EF2_1_fow
cagccgaagcg

SEQ ID NO: 114:
EF2_2_fow
cagcccaagcg

SEQ ID NO: 115:
EF2_3_fow
agccgaagcgYc

SEQ ID NO: 116:
EF2_4_fow
agcccaagcggcc

SEQ ID NO: 117:
EF2_5_fow
agccgaagcgtcc

SEQ ID NO: 118:
EF2_6_fow
agccgaagcgccc

SEQ ID NO: 119:
EF2_10_fow
agcgcccctgctcc

SEQ ID NO: 120:
EF2_11_fow
cccgagcagcccgacc

SEQ ID NO: 121:
EF2_1_rev
cgtgtgcgacgt

SEQ ID NO: 122:
EF2_3_rev
cgtgagcgagtg

SEQ ID NO: 123:
EF2_4_rev
cgtgwgcgacgt

-continued

SEQ ID NO: 124:
EF2_7_rev
cgtgtgcgacgtgtccg

SEQ ID NO: 125:
A.fum_EF2_2
cgacgctcacacctctgtc

SEQ ID NO: 126:
>CA3345\(EF2) eIF2 γ sequence generated for *C. albicans*
ATTGAAACATGTTATTATTTTGCAAAATAAAGTTGATTTGATGAGAGAAGAATCAG

CCTTGGAACACGAAAAATCTATCATTCAGTTTATTAGAGGTACAATTGCCGATAAT

GCTCCGATCGTGCCTATTTCTGCTCAATTGAAATACAACATTGATGCAGTGAATCAA

TTTATTGTTAACTACATACCTGTGCCAATGAGAGACTTTACTGCTTCACCAAGATTG

ATCGTTATCAGATCTTTCGATGTGAACAAGCCTGGTGCAGATGTAGACGAATTGAA

AGGAGGTGTTGCAGGTGGTTC

SEQ ID NO: 127:
>CA16733\(EF2) eIF2 γ sequence generated for *C. albicans*
ATTGAAACATGTTATTATTTTGCAAAATAAAGTTGATTTGATGAGAGAAGAATCAG

CCTTGGAACACGAAAAATCTATCATTCAGTTTATTARAGGTACAATTGCCGATAATG

CTCCGATCGTGCCTATTTCTGCTCAATTRAAATACAACATTGATGCAGTGAATCAAT

TTATYGTTAACTACATACCTGTGCCAATGAGAGACTTTACTGCTTCACCAAGATTGA

TCGTTATCAGATCTTTCGATGTGAACAAGCCTGGTGCAGATGTAGACGAATTGAAA

GGAGGTGTTGCAGGTGGTTC

SEQ ID NO: 128:
>CA1899\(EF2) eIF2 γ sequence generated for *C. albicans*
ATTGAAACATGTTATTATTTTGCAAAATAAAGTTGATTTGATGAGAGAAGAATCAG

CYTTGGAACACGAAAAATCTATYATTCAGTTTATTARAGGTACAATTGCCGATAAT

GCTCCGATCGTGCCTATTTCTGCTCAATTRAAATACAACATTGATGCAGTGAATCAA

TTTATYGTTAACTACATACCTGTGCCAATGAGAGACTTTACTGCTTCACCAAGATTG

ATCGTTATCAGATCTTTCGATGTGAACAAGCCTGGTGCAGATGTAGACGAATTGAA

AGGAGGTGTTGCAGGTGGTTC

SEQ ID NO: 129:
>CA1912\(EF2) eIF2 γ sequence generated for *C. albicans*
ATTGAAACATGTTATTATTTTGCAAAATAAAGTTGATTTGATGAGAGAAGAATCAG

CCTTGGAACACGAAAAATCTATCATTCAGTTTATTAGAGGTACAATTGCCGATAAT

GCTCCGATCGTGCCTATTTCTGCTCAATTGAAATACAACATTGATGCAGTGAATCAA

TTTATTGTTAACTACATACCTGTGCCAATGAGAGACTTTACTGCTTCACCAAGATTG

ATCGTTATCAGATCTTTCGATGTGAACAAGCCTGGTGCAGATGTAGACGAATTGAA

AGGAGGTGTTGCAGGTGGTTC

SEQ ID NO: 130:
>CA2312\(EF2) eIF2 γ sequence generated for *C. albicans*
ATTGAAACATGTTATTATTTTGCAAAATAAAGTTGATTTGATGAGAGAAGAATCAG

CCTTGGAACACGAAAAATCTATCATTCAGTTTATTAGAGGTACAATTGCCGATAAT

GCTCCGATCGTGCCTATTTCTGCTCAATTRAAATACAACATTGATGCAGTGAATCAA

TTTATYGTTAACTACATACCTGTGCCAATGAGAGACTTTACTGCTTCACCAAGATTG

ATCGTTATCAGATCTTTCGATGTGAACAAGCCTGGTGCAGATGTAGACGAATTGAA

AGGAGGTGTTGCAGGTGGTTC

SEQ ID NO: 131:
>CA2688\(EF2) eIF2 γ sequence generated for *C. albicans*
ATTGAAACATGTTATTATTTTGCAAAATAAAGTTGATTTGATGAGAGAAGAATCAG

CCTTGGAACACGAAAAATCTATCATTCAGTTTATTAAAGGTACAATTGCCGATAAT

GCTCCGATCGTGCCTATTTCTGCTCAATTGAAATACAACATTGATGCAGTGAATCAA

TTTATTGTTAACTACATACCTGTGCCAATGAGAGACTTTACTGCTTCACCAAGATTG

ATCGTTATCAGATCTTTCGATGTGAACAAGCCTGGTGCAGATGTAGACGAATTGAA

AGGAGGTGTTGCAGGTGGTTC

SEQ ID NO: 132:
>CA2701\(EF2) eIF2 γ sequence generated for *C. albicans*
ATTGAAACATGTTATTATTTTGCAAAATAAAGTTGATTTGATGAGAGAAGAATCAG

CYTTGGAACACGAAAAATCTATYATTCAGTTTATTAGAGGTACAATTGCCGATAAT

GCTCCGATCGTGCCTATTTCTGCTCAATTRAAATACAACATTGATGCAGTGAATCAA

TTTATYGTTAACTACATACCTGTGCCAATGAGAGACTTTACTGCTTCACCAAGATTG

ATCGTTATCAGATCTTTCGATGTGAACAAGCCTGGTGCAGATGTAGACGAATTGAA

AGGAGGTGTTGCAGGTGGTTC

SEQ ID NO: 133:
>CA15640\(EF2) eIF2 γ sequence generated for *C. albicans*
ATTGAAACATGTTATTATTTTGCAAAATAAAGTTGATTTGATGAGAGAAGAATCAG

CCTTGGAACACGAAAAATCTATCATTCAGTTTATTARAGGTACAATTGCCGATAATG

CTCCGATCGTGCCTATTTCTGCTCAATTGAAATACAACATTGATGCAGTGAATCAAT

TTATTGTTAACTACATACCTGTGCCAATGAGAGACTTTACTGCTTCACCAAGATTGA

TCGTTATCAGATCTTTCGATGTGAACAAGCCTGGTGCAGATGTAGACGAATTGAAA

GGAGGTGTTGCAGGTGGTTC

SEQ ID NO: 134:
>CA1893\(EF2) eIF2 γ sequence generated for *C. albicans*
ATTGAAACATGTTATTATTTTGCAAAATAAAGTTGATTTGATGAGAGAAGAATCAG

CCTTGGAACACGAAAAATCTATCATTCAGTTTATTARAGGTACAATTGCCGATAATG

CTCCGATCGTGCCTATTTCTGCTCAATTGAAATACAACATTGATGCAGTGAATCAAT

TTATTGTTAACTACATACCTGTGCCAATGAGAGACTTTACTGCTTCACCAAGATTGA

TCGTTATCAGATCTTTCGATGTGAACAAGCCTGGTGCAGATGTAGACGAATTGAAA

GGAGGTGTTGCAGGTGGTTC

SEQ ID No: 135:
CEF1F
ATCTATCATTCAGTTTATTAGAG

SEQ ID NO 136:
CEF2F
CATTCAGTTTATTAGAGGTAC

SEQ ID NO 137:
CEFR2
CAGTAAAGTCTCTCATTG

SEQ ID NO 138:
ALEF1
TGCCGATAATGCTCCGATC

REFERENCES

Alone P V, Dever T E.
Direct binding of translation initiation factor eIF2gamma-G domain to its GTPase-activating and GDP-GTP exchange factors eIF5 and eIF2B epsilon. J Biol Chem. 2006 May 5; 281(18):12636-44. Epub 2006 Mar. 7.

Dorris D R, Erickson F L, Hannig E M.
Mutations in GCD11, the structural gene for eIF-2 gamma in yeast, alter translational regulation of GCN4 and the selection of the start site for protein synthesis. EMBO J. 1995 May 15; 14(10):2239-49

Erickson F L, Harding L D, Dorris D R, Hannig E M.
Functional analysis of homologs of translation initiation factor 2gamma in yeast. Mol Gen Genet. 1997 Feb. 27; 253(6):711-9.

Erickson F L, Hannig E M.
Ligand interactions with eukaryotic translation initiation factor 2: role of the gamma-subunit. EMBO J. 1996 Nov. 15; 15(22):6311-20.

The invention claimed is:

1. A diagnostic kit for a yeast or fungal species comprising a first oligonucleotide probe attached to a detectable moiety wherein the first probe is capable of binding to at least a portion of an eIF2 γ gene or its corresponding mRNA; and a second oligonucleotide probe capable of binding to at least a portion of an eIF2 γ gene or its corresponding mRNA, wherein the second probe is capable of binding a portion of the eIF2 γ gene or its corresponding mRNA that is a different yeast or different fungal species than the first probe, and wherein the detectable moiety is not a nucleic acid.

2. A kit as claimed in claim 1, wherein the portion of the eIF2 γ gene is equivalent to a portion of the region of the gene from base pair position 718 to 1040 of C. albicans eIF2 γ gene, from base pair position 790 to 934 of C. albicans eIF2 γ gene, from base pair position 872 to 972 of C. glabrata eIF2 γ gene, from base pair position 151 to 274 of C. parapsilosis eIF2 γ gene, from base pair position 140 to 270 of C. tropicalis eIF2 γ gene, from base pair position 115 to 224 of C. krusei eIF2 γ gene, from base pair position 121 to 374 of A. fumigatus eIF2 γ gene, from base pair position 164 to 261 of A. fumigatus eIF2 γ gene, from base pair position 155 to 252 of A. flavus eIF2 γ gene, from base pair position 92 to 189 of A. niger eIF2 γ gene, or from base pair position 149 to 246 of A. terreus eIF2 γ gene.

3. A kit as claimed in claim 1 or 2 wherein the first probe is selected from the group consisting of SEQ ID NO: 108, 109, 110, or 111 or sequences at least 90% similar or complementary thereto, and further comprising a forward primer selected from the group consisting of SEQ ID NO: 3, 5, 89, 91, 93, 95, 97, 104, 105, 112, 113, 114, 115, 116, 117, 118, 119, 120, 135 or 136, or sequences at least 90% similar or complementary thereto which can also act as a forward amplification primer and a reverse primer selected from the group consisting of SEQ ID NO 4, 6, 90, 92, 94, 96, 98, 106, 107, 121, 122, 123, 124, 137, and sequences at least 90% similar or complementary thereto which can also act as a reverse amplification primer.

4. The kit of claim 3, wherein the primer is detectably labeled with a detectable moiety selected from the group of a radioisotope, a fluorescent moiety, a chemiluminescent, a nanoparticle moiety, an enzyme or a ligand.

5. The kit of claim 1 or 2, wherein the detectable moiety is selected from the group of a radioisotope, a fluorescent moiety, a chemiluminescent, a nanoparticle moiety, an enzyme or a ligand.

6. The kit of claim 1, wherein the kit is an in vitro amplification technology kit and further comprises at least one additional reagent for use in Polymerase Chain Reaction (PCR), Ligase Chain Reaction (LCR), Nucleic Acids Sequence Based Amplification (NASBA), Strand Displacement Amplification (SDA), Transcription Mediated Amplification (TMA), Branched DNA technology (bDNA), Rolling Circle Amplification Technology (RCAT), or an in vitro enzymatic amplification technology.

7. The kit of claim 1, wherein the first probe comprises a nucleic acid molecule selected from the group consisting of: SEQ ID NO: 1-6, 84-98, 104-114, 121, 122, 136, and 138 and sequences at least 90% similar or complementary thereto and having a function in diagnostics based on the eIF2 γ gene wherein the nucleic acid is attached to a detectable moiety, and wherein the detectable moiety is not a nucleic acid.

8. An oligonucleotide probe or a set of oligonucleotide probes, comprising
a first nucleic acid molecule, selected from the group consisting of: SEQ ID Nos 85-88, 92, 94-96, 98, 105, 108, or 109 and sequences at least 95% similar or complementary thereto, wherein the oligonucleotide probe has a function in diagnostics based on the eIF2 γ gene wherein the first nucleic acid molecule is attached to a detectable moiety, and wherein the detectable moiety is not a nucleic acid; and
optionally a second nucleic acid molecule selected from the group consisting of SEQ ID Nos 1, 2, 3-5, 6, 84, 89-91, 93, 97, 104, 106, 107, 110-113, 114, 121, 122, 136, 138, or combination thereof, and wherein the second nucleic acid molecule is attached to a detectable moiety, and wherein the detectable moiety is not a nucleic acid.

9. The oligonucleotide probe or the set of oligonucleotide probes of claim 8, wherein the detectable moiety is selected from the group consisting of a radioisotope, a fluorescent moiety, a chemiluminescent, a nanoparticle moiety, an enzyme or a ligand.

* * * * *

SEQUENCE LISTING

```
<160> NUMBER OF SEQ ID NOS: 149

<210> SEQ ID NO 1
<211> LENGTH: 23
<212> TYPE: DNA
<213> ORGANISM: Artificial Sequence
<220> FEATURE:
<223> OTHER INFORMATION: P1-CaneIF2

<400> SEQUENCE: 1
cgataatgct ccgatcgtgc cta                                              23

<210> SEQ ID NO 2
<211> LENGTH: 23
<212> TYPE: DNA
<213> ORGANISM: Artificial Sequence
<220> FEATURE:
<223> OTHER INFORMATION: P1-AspeIF2

<400> SEQUENCE: 2
cgctcacacc tctgtcgccc gaa                                              23

<210> SEQ ID NO 3
<211> LENGTH: 19
<212> TYPE: DNA
<213> ORGANISM: Artificial Sequence
<220> FEATURE:
<223> OTHER INFORMATION: AspeIF2-F

<400> SEQUENCE: 3
cttaagtctg cgatgaaga                                                   19

<210> SEQ ID NO 4
<211> LENGTH: 20
<212> TYPE: DNA
<213> ORGANISM: Artificial Sequence
<220> FEATURE:
<223> OTHER INFORMATION: AspeIF2-R

<400> SEQUENCE: 4
gtaatgttac gctccaactc                                                  20

<210> SEQ ID NO 5
<211> LENGTH: 20
<212> TYPE: DNA
<213> ORGANISM: Artificial Sequence
<220> FEATURE:
<223> OTHER INFORMATION: CaneIF2-F

<400> SEQUENCE: 5
gctgccattg aaattatgaa                                                  20

<210> SEQ ID NO 6
<211> LENGTH: 17
<212> TYPE: DNA
```

<213> ORGANISM: Artificial Sequence
<220> FEATURE:
<223> OTHER INFORMATION: CaneIF2-R

<400> SEQUENCE: 6
gaaccacctg caacacc                                                17

<210> SEQ ID NO 7
<211> LENGTH: 283
<212> TYPE: DNA
<213> ORGANISM: Candida albicans

<400> SEQUENCE: 7
tgcataataa agttgatttg atgagagaag aatcagcctt ggaacacgaa aaatctatca    60
ttcagtttat tagaggtaca attgccgata atgctccgat cgtgcctatt tctgctcaat   120
tgaaatacaa cattgatgca gtgaatcaat ttattgttaa ctacatacct gtgccaatga   180
gagactttac tgcttcacca agattgatcg ttatcagatc tttcgatgtg aacaagcctg   240
gtgcagatgt agacgaattg aaaggaggtg ttgcaggtgg ttc                     283

<210> SEQ ID NO 8
<211> LENGTH: 290
<212> TYPE: DNA
<213> ORGANISM: Candida albicans

<400> SEQUENCE: 8
attattttgc ataataaagt tgatttgatg agagaagaat cagcyttgga acacgaaaaa    60
tctatcattc agtttattag aggtacaatt gccgataatg ctccgatcgt gcctatttct   120
gctcaattra aatacaacat tgatgcagtg aatcaattta tygttaacta catacctgtg   180
ccaatgagag acttractgc ttcaccaaga ttgatygtta tcagatcttt cgatgtgaac   240
aagcctggtg cagatgtaga cgaattgaaa ggaggtgttg caggtggttc               290

<210> SEQ ID NO 9
<211> LENGTH: 290
<212> TYPE: DNA
<213> ORGANISM: Candida albicans

<400> SEQUENCE: 9
attattttgc ataataaagt tgatttgatg agagaagaat cagcyttggr acacgaaaaa    60
tctatcattc agtttattag aggtacaatt gccgataatg ctccgatcgt gcctatttct   120
gctcaattga aatacaacat tgatgcagtg aatcaattta tygttaacta catacctgtg   180
ccaatgagag acttractgc ttcaccaaga ttgatygtta tcagatcttt cgatgtgaac   240
aagcctggtg cagatgtaga cgaattgaaa ggaggtgttg caggtggttc               290

<210> SEQ ID NO 10
<211> LENGTH: 303
<212> TYPE: DNA
<213> ORGANISM: Candida albicans

<400> SEQUENCE: 10
attgaaacat gttattattt tgcataataa agttgatttg atgagagaag aatcagcctt    60
ggaacacgaa aaatctatca ttcagtttat tagaggtaca attgccgata atgctccgat   120
cgtgcctatt tctgctcaat tgaaatacaa cattgatgca gtgaatcaat ttattgttaa   180
ctacatacct gtgccaatga gagactttac tgcttcacca agattgatcg ttatcagatc   240
tttcgatgtg aacaagcctg gtgcagatgt agacgaattg aaaggaggtg ttgcaggtgg   300

```
ttc                                                                  303

<210> SEQ ID NO 11
<211> LENGTH: 303
<212> TYPE: DNA
<213> ORGANISM: Candida glabrata

<400> SEQUENCE: 11
gttaaagcac gttattattc tacagaacaa ggtcgattta atgcgtgaag aaagcgcact    60
agaacatgaa aagtctatcc tgaaatttat cagaggtact attgctgacg gtgctccaat   120
tgtcccaatt ccgctcaat tgaaatacaa catcgatgca gttaatgaat ttatcgtgaa    180
gactatccct gttccaccaa gagatttcat gctttctcca cgtttgattg tcattcgttc   240
tttcgatgtt aacaagccag gtgctgaaat cgatgatttg aagggtggtg ttgcaggtgg   300
ttc                                                                  303

<210> SEQ ID NO 12
<211> LENGTH: 303
<212> TYPE: DNA
<213> ORGANISM: Candida glabrata

<400> SEQUENCE: 12
gttaaagcac gttattattc tacagaacaa ggtcgattta atgcgtgaag aaagcgcact    60
agaacatgaa aagtctatcc tgaaatttat cagaggtact attgctgacg gtgctccaat   120
tgtcccaatt ccgctcaat tgaaatacaa catcgatgca gttaacgaat ttatcgtgaa    180
gactatccct gttccaccaa gagatttcat gctttctcca cgtttgattg tcattcgttc   240
tttcgatgtt aacaagccag gtgctgaaat cgatgatttg aagggtggtg ttgcaggtgg   300
ttc                                                                  303

<210> SEQ ID NO 13
<211> LENGTH: 303
<212> TYPE: DNA
<213> ORGANISM: Candida glabrata

<400> SEQUENCE: 13
gttaaagcac gttattattc tacagaacaa ggtcgattta atgcgtgaag aaagcgcact    60
agaacatgaa aagtctatcc tgaaatttat cagaggtact attgctgacg gtgctccaat   120
tgtcccaatt ccgctcaat tgaaatacaa catcgatgca gtcaatgaat ttatcgtgaa    180
gactatccct gttccaccaa gagatttcat gctttctcca cgtttgattg tcattcgttc   240
tttcgatgtt aacaagccag gtgctgaaat cgatgatttg aagggtggtg ttgcaggtgg   300
ttc                                                                  303

<210> SEQ ID NO 14
<211> LENGTH: 303
<212> TYPE: DNA
<213> ORGANISM: Candida glabrata

<400> SEQUENCE: 14
gttaaagcac gttattattc tacagaacaa ggtcgattta atgcgtgaag aaagcgcact    60
agaacatgaa aagtctatcc tgaaatttat cagaggtact attgctgacg gtgctccaat   120
tgtcccaatt ccgctcaat tgaaatacaa catcgatgca gtcaatgaat ttatcgtgaa    180
gactatccct gttccaccaa gagatttcat gctttctcca cgtttgattg tcattcgttc   240
```

```
tttcgatgtt aacaagccag gtgctgaaat cgatgatttg aagggtggtg ttgcaggtgg    300
ttc                                                                  303

<210> SEQ ID NO 15
<211> LENGTH: 294
<212> TYPE: DNA
<213> ORGANISM: Candida kruisi

<400> SEQUENCE: 15
tgktgtgatt ktacaaaata aagttgattt gatgaagaaa gaagcagctt tagagcacga     60
aaaatctatt ttgaagttta tcaagggtac tattgctgat ggtgctccta ttatcccaat    120
ttctgctcag ttgaaataca acattgatgc agttaacatg tgtatggtca agtctattcc    180
tgttccaatt agagacttta ctgcagttcc aagattaatg gttattagat ctttcgatgt    240
taataagcct ggtgcagaaa ttgcagattt gaaaggtggt gttgcaggtg gttc          294

<210> SEQ ID NO 16
<211> LENGTH: 294
<212> TYPE: DNA
<213> ORGANISM: Candida kruisi

<400> SEQUENCE: 16
tgttgtgatt ttacaaaata aagttgattt gatgaagaaa gaagcagctt tagagcacga     60
aaaatctatt ttgaagttta tcaagggtac tattgctgat ggtgctccta ttatcccaat    120
ttctgctcag ttgaaataya acattgatgc agttaacatg tgtatggtca agtctattcc    180
tgttccaatt agagacttta cygcagttcc aagattaatg gttattagat ctttcgatgt    240
taataagcct ggtgcagaaa ttgcagattt gaaaggtggt gttgcaggtg gttc          294

<210> SEQ ID NO 17
<211> LENGTH: 294
<212> TYPE: DNA
<213> ORGANISM: Candida kruisi

<400> SEQUENCE: 17
tgttgtgatt ttacaaaata aagttgattt gatgaagaaa gaagcagctt tagagcacga     60
aaaatctatt ttgaagttta tcaagggtac tattgctgat ggtgctccta ttatcccaat    120
ttctgctcag ttgaaatata acattgatgc agttaacatg tgtatggtca agtctattcc    180
tgttccaatt agagacttta ccgcagttcc aagattaatg gttattagat ctttcgatgt    240
taataagcct ggtgcagaaa ttgcagattt gaaaggtggt gttgcaggtg gttc          294

<210> SEQ ID NO 18
<211> LENGTH: 294
<212> TYPE: DNA
<213> ORGANISM: Candida kruisi

<400> SEQUENCE: 18
tgktgtgatt ktacaaaata aagttgattt gatgaagaaa gaagcagctt tagagcacga     60
aaaatctatt ttgaagttta tcaagggtac tattgctgat ggtgctccta ttatcccaat    120
ttctgctcag ttgaaatata acattgatgc agttaacatg tgtatggtca agtctattcc    180
tgttccaatt agagacttta ccgcagttcc aagattaatg gttattagat ctttcgatgt    240
taataagcct ggtgcagaaa ttgcagattt gaaaggtggt gttgcaggtg gttc          294

<210> SEQ ID NO 19
<211> LENGTH: 303
```

<212> TYPE: DNA
<213> ORGANISM: Candida parapsilosis

<400> SEQUENCE: 19

```
gttgaagcat gttataattt tgcaaaacaa ggttgatttg atgagagaag artcrgcatt      60
ggaacatgaa aagtctatta ttcagttcat aagaggtacc atagctgatg gtgcaccaat     120
agttccaatt tcggcacaat tgaaatataa tatcgatgcc gtcaatcaat tcatagtcaa     180
ctccatacct gtcccagtta gagayttac tgcatcacca agattgattg ttattaggtc      240
tttygatgts aacaaacctg gtgctgatgt tgatgacttg aagggaggtg ttgcaggtgg     300
ttc                                                                   303
```

<210> SEQ ID NO 20
<211> LENGTH: 303
<212> TYPE: DNA
<213> ORGANISM: Candida parapsilosis

<400> SEQUENCE: 20

```
gttgaagcac gttattattt tgcaaaacaa agttgattta atgagaaagg agtcagcttt      60
ggaacatgaa aagtccatca ttcagttcat cagaggtact atagctgatg gtgccccaat    120
tgttccaatt tcagcacaat tgaagtataa tatcgacgcc gtcaatcaat tcatcgtaaa    180
ctcaatacca gttccagtca gggactttac tgcatcccct aggttaattg ttattaggtc    240
ttttgatgtg aacaaacctg gtgctgacgt tgatgatttg aaaggaggtg ttgcaggtgg    300
ttc                                                                   303
```

<210> SEQ ID NO 21
<211> LENGTH: 294
<212> TYPE: DNA
<213> ORGANISM: Candida parapsilosis

<400> SEQUENCE: 21

```
tgttataatt ttacaaaata aggttgattt gatgagagaa gagtckgcat tggagcatga      60
raagtcgata cttcaattca taagaggtac tatagcmgat ggtgctccaa ttgttccaat    120
ttcagctcaa ttgaaataca atatcgacgc cgtcaatcaa tttatagtaa attccatacc    180
sgttccaatt agggatttca atgcctcacc aaggttgatt gttattcgat catttgatgt    240
gaayaaacct ggtgctgatg tcgaygattt gaagggaggt gttgcaggtg gttc           294
```

<210> SEQ ID NO 22
<211> LENGTH: 303
<212> TYPE: DNA
<213> ORGANISM: Candida parapsilosis

<400> SEQUENCE: 22

```
gttgaagcac gttattattt tgcaaaacaa agttgattta atgagaaagg agtcagcttt      60
ggaacatgaa aagtccatca ttcagttcat cagaggtact atagctgatg gtgccccaat    120
tgttccaatt tcagcacaat tgaagtataa tatcgacgcc gtcaatcaat tcatcgtaaa    180
ctcaatacca gttccagtca gggactttac tgcatcccct aggttaattg ttattaggtc    240
ttttgatgtg aacaaacctg gtgctgacgt tgatgatttg aaaggaggtg ttgcaggtgg    300
ttc                                                                   303
```

<210> SEQ ID NO 23
<211> LENGTH: 273
<212> TYPE: DNA

<213> ORGANISM: Candida tropicalis

<400> SEQUENCE: 23

| ggtcgatttg atgagagaag aatctgcctt ggaacatgag aaatccattc ttcaattcat | 60 |
| cagaggtact attgcagaca atgctcctat tgtcccaatt tctgcccaat tgaaatacaa | 120 |
| catcgatgcc gttaaccaat ttattgtcaa ttatatccca gttccattga gacttttc | 180 |
| cgcttcccca agattgattg tcatcagatc ttttgatgtc aacaagccag gttccgatgt | 240 |
| cgaagacttg aaaggggggtg ttgcaggtgg ttc | 273 |

<210> SEQ ID NO 24
<211> LENGTH: 273
<212> TYPE: DNA
<213> ORGANISM: Candida tropicalis

<400> SEQUENCE: 24

| ggtcgatttg atgagagaag aatctgcctt ggaacatgag aaatccattc ttcaattcat | 60 |
| cagaggtact attgcagaca atgctcctat tgtcccaatt tctgcccaat tgaaatacaa | 120 |
| catcgatgcc gttaaccaat ttattgtcaa ttatatccca gttccattga gacttttc | 180 |
| cgcttcccca agattgattg tcatcagatc ttttgatgtc aacaagccag gttccgatgt | 240 |
| cgaagacttg aaaggggggtg ttgcaggtgg ttc | 273 |

<210> SEQ ID NO 25
<211> LENGTH: 293
<212> TYPE: DNA
<213> ORGANISM: Candida tropicalis

<400> SEQUENCE: 25

| gtcatkattt tgcagaacaa ggtcgatttg atgagagaag aatctgcctt ggaacatgag | 60 |
| aaatccattc ttcaattcat cagaggtact attgcagaca atgctcctat tgtcccaatt | 120 |
| tctgcccaat tgaaatacaa catcgatgcc gttaaccaat ttattgtcaa ttatatccca | 180 |
| gttccattga gacttttc cgcttcccca agattgattg tcatcagatc ttttgatgtc | 240 |
| aacaagccag gttccgatgt cgaagacttg aaaggggggtg ttgcaggtgg ttc | 293 |

<210> SEQ ID NO 26
<211> LENGTH: 273
<212> TYPE: DNA
<213> ORGANISM: Candida tropicalis

<400> SEQUENCE: 26

| ggtcgatttg atgagagaag aatctgcctt ggaacatgag aaatccattc ttcaattcat | 60 |
| cagaggtact attgcagaca atgctcctat tgtcccaatt tctgcccaat tgaaatacaa | 120 |
| catcgatgcc gttaaccaat ttattgtcaa ttatatccca gttccattga gacttttc | 180 |
| cgcttcccca agattgattg tcatcagatc ttttgatgtc aacaagccag gttccgatgt | 240 |
| cgaagacttg aaaggggggtg ttgcaggtgg ttc | 273 |

<210> SEQ ID NO 27
<211> LENGTH: 278
<212> TYPE: DNA
<213> ORGANISM: Candida dubliniensis

<400> SEQUENCE: 27

| aataaagttg atttgatgag agaagaatca gctttggaac atgaaaaatc cattattcag | 60 |
| ttcatcagag gcacaattgc tgataacgcc ccaattgtgc ctatttctgc gcaattgaaa | 120 |

```
tacaacattg atgctgtaaa tcaatttatt gtgaactaca tacctgtgcc aatgagagac     180
tttactgctt caccaagatt gatcgttatt agatcttttg atgtgaacaa gcctggtgcg     240
gatgttgacg aattgaaagg gggtgttgca ggtggttc                             278
```

<210> SEQ ID NO 28
<211> LENGTH: 301
<212> TYPE: DNA
<213> ORGANISM: Candida dubliniensis

<400> SEQUENCE: 28

```
tgaaacatgt cattattttg cagaataaag ttgatttgat gagagaagaa tcagctttgg      60
aacatgaaaa atccattatt cagttcatca gaggcacaat tgctgataac gccccaattg     120
tgcctatttc tgcgcaattg aaatacaaca ttgatgctgt aaatcaattt attgtgaact     180
acatacctgt gccaatgaga gactttactg cttcaccaag attgatcgtt attagatctt     240
ttgatgtgaa caagcctggt gcggatgttg acgaattgaa aggggtgtt gcaggtggtt     300 c                                                                    301
```

<210> SEQ ID NO 29
<211> LENGTH: 303
<212> TYPE: DNA
<213> ORGANISM: Candida dubliniensis

<400> SEQUENCE: 29

```
attgaaacat gtcattattt tgcagaataa agttgatttg atgagagaag aatcagcttt      60
ggaacatgaa aaatccatta ttcagttcat cagaggcaca attgctgata acgccccaat     120
tgtgcctatt tctgcgcaat tgaaatacaa cattgatgct gtaaatcaat ttattgtgaa     180
ctacatacct gtgccaatga gagactttac tgcttcacca agattgatcg ttattagatc     240
ttttgatgtg aacaagcctg gtgcggatgt tgacgaattg aaaggggtg ttgcaggtgg     300 ttc                                                                   303
```

<210> SEQ ID NO 30
<211> LENGTH: 284
<212> TYPE: DNA
<213> ORGANISM: Candida guilliermondii

<400> SEQUENCE: 30

```
ttgcaaaata aggtggatct tatgagagaa gaatcggcgt tggagcacca aaaatcgatt      60
ttgaatttta ttaaaggaac catcgctgac ggtgccccca tcgtccctat ctcggcccaa     120
ttgaagtaca acatcgatgc cgtgaaccaa ttcatagtca actcgatccc cgttcctcct     180
cgtgactttt ccgcatctcc tcggttgatc gtgattcgtt ctttcgacgt caataaaccc     240
ggttctgaaa ttgatgactt gaagggaggt gttgcaggtg gttc                     284
```

<210> SEQ ID NO 31
<211> LENGTH: 303
<212> TYPE: DNA
<213> ORGANISM: Candida guilliermondii

<400> SEQUENCE: 31

```
gttgaaacat gttatcatct tgcaaaatag gtggatcttat gagagaag aatcggcgtt      60 ggagcaccaa aaatcgattt tgaattttat taaaggaacc atcgctgatg gtgcacctat     120
cgtccctatc tcggcccagt tgaagtacaa catcgatgcc gtgaaccaat tcatagtcaa     180
```

```
ctcgatcccc gttcctcctc gtgacttttc cgcatctcct cggttgatcg tgattcgttc      240
tttcgacgtc aataaacccg gttctgagat cgatgacttg aaaggaggtg ttgcaggtgg      300
ttc                                                                    303
```

<210> SEQ ID NO 32
<211> LENGTH: 303
<212> TYPE: DNA
<213> ORGANISM: Candida guilliermondii

<400> SEQUENCE: 32

```
gttgaaacat gttatcatct tgcaaaataa ggtggatctt atgagagaag aatcggcgtt       60
ggagcaccaa aaatcgattt tgaattttat taaaggaacc atcgctgatg gtgcacctat      120
cgtccctatc tcggcccagt tgaagtacaa catcgatgcc gtgaaccaat tcatagtcaa      180
ctcgatcccc gttcctcctc gtgacttttc cgcatctcct cggttgatcg tgattcgttc      240
tttcgacgtc aataaacccg gttctgagat cgatgacttg aaaggaggtg ttgcaggtgg      300
ttc                                                                    303
```

<210> SEQ ID NO 33
<211> LENGTH: 303
<212> TYPE: DNA
<213> ORGANISM: Candida norvegiensis

<400> SEQUENCE: 33

```
gttgaaacac gttgttattt tacaaaataa agttgatttg atgaaaaagg aagctgcgtt       60
ggaacacgaa aaatctattc ttaagttcat caagggtacg atcgctgatg gagctccaat      120
cattcctatt tctgcacaat tgaaatataa cattgatgct gttaacatgt gtatggtaaa      180
ctccattcca attccaatga gagattttac tgctcagcca agattaatgg tcatcagatc      240
tttcgatgtt aacaaacctg gtgcagaaat aaatgatttg aaaggtggtg ttgcaggtgg      300
ttc                                                                    303
```

<210> SEQ ID NO 34
<211> LENGTH: 303
<212> TYPE: DNA
<213> ORGANISM: Candida famata

<400> SEQUENCE: 34

```
attgartcat gttattatct tacaaaacaa ggttgattta atgaragagg aatcagcttt       60
ggaacatcag aaatctattt tgagtttcat cagaggtact attgcagatg gtgctccaat      120
tgttccaatt tctgcccaat aaaatataa tatcgatgct gttaatcaat ttattgtgaa       180
ctctattcca attcctccaa gagacttcat ggctactcca agattgatcg ttattagatc      240
tttcgatgtt aataaaccag gtgccgagat tgatgacttg aagggtggtg ttgcaggtgg      300
ttc                                                                    303
```

<210> SEQ ID NO 35
<211> LENGTH: 293
<212> TYPE: DNA
<213> ORGANISM: Candida famata

<400> SEQUENCE: 35

```
gtgattatct tacaaaataa ggttgattta atgagagaag agtcagcttt agagcatcaa       60
aagtccattt tgagtttcat cagaggtact attgctgatg gtgctccaat tgttccaatt      120
tctgctcaat aaaatataa tattgatgct gtcaatcaat ttattgttaa ttctattcca      180
```

```
attccgccaa gagacttsat ggctactcca agattgatcg atattagatc attcgatgtt    240
aataaaccag gggcagaaat tgatgacttg aagggtggtg ttgcaggtgg ttc            293

<210> SEQ ID NO 36
<211> LENGTH: 303
<212> TYPE: DNA
<213> ORGANISM: Candida famata

<400> SEQUENCE: 36
attgaagcat gtgatcatct tacaaaataa ggttgattta atgagagaag aatctgcttt     60
agagcatcaa aagtccattt tgagtttcat cagaggtact attgctgatg gtgctccaat   120
tgttccaatt tctgctcaat taaaatataa tattgatgct gtcaatcaat ttattgttaa   180
ttctattcca attccgccaa gagacttgat ggctactcca agattgatcg atattagatc   240
attcgatgtt aataaaccag gtgctgaaat tgatgacttg aagggtggtg ttgcaggtgg   300
ttc                                                                 303

<210> SEQ ID NO 37
<211> LENGTH: 294
<212> TYPE: DNA
<213> ORGANISM: Candida haemuloni

<400> SEQUENCE: 37
cgttatcatt ttgcagaaca aggtggattt gatgagagaa gagtctgctt tggagcacca    60
gaaatcgatc ttgagtttta tcagaggtac cattgccgat ggcgctccta tcgtgccaat   120
ttccgcccaa ttgaagtaca acattgacgc tgtcaaccag ttgatctgcg actacatccc   180
tgttcctcct agagacttca tggcctcgcc acgtttgatc gtcattaggt ctttcgatgt   240
caacaagcca ggtgccgaga tcgaggactt gaagggaggt gttgcaggtg gttc          294

<210> SEQ ID NO 38
<211> LENGTH: 294
<212> TYPE: DNA
<213> ORGANISM: Candida haemuloni

<400> SEQUENCE: 38
cgttatcatt ttgcagaaca aggtggattt gatgagagaa gagtctgctt tggagcacca    60
gaaatcgatc ttgagtttta tcagaggtac cattgccgat ggcgctccta tcgtgccaat   120
ttccgcccaa ttgaagtaca acattgacgc tgtcaaccag ttgatctgcg actacatccc   180
tgttcctcct agagacttca tggcctcgcc acgtttgatc gtcattaggt ctttcgatgt   240
caacaagcca ggtgccgaga tcgaggactt gaagggaggt gttgcaggtg gttc          294

<210> SEQ ID NO 39
<211> LENGTH: 294
<212> TYPE: DNA
<213> ORGANISM: Candida haemuloni

<400> SEQUENCE: 39
cgttatcatt ttgcagaaca aggtggattt gatgagagaa gagtctgctt tggagcacca    60
gaaatcgatc ttgagtttta tcagaggtac cattgccgat ggcgctccta tcgtgccaat   120
ttccgcccaa ttgaagtaca acattgacgc tgtcaaccag ttgatctgcg actacatccc   180
tgttcctcct agagacttca tggcctcgcc acgtttgatc gtcattaggt ctttcgatgt   240
caacaagcca ggtgccgaga tcgaggactt gaagggaggt gttgcaggtg gttc          294
```

```
<210> SEQ ID NO 40
<211> LENGTH: 289
<212> TYPE: DNA
<213> ORGANISM: Candida Kefyr

<400> SEQUENCE: 40
ttattcttca gaacaaggtg gatctaatga gagaagactc cgctctagag catcaaaaat      60
ctattttgaa gtttatcaga ggtactattg ccgatggtgc accaattgtt ccaatttctg    120
ctcaattgaa gtacaatatt gatgccgtta acgaatttat cgttaagagt atcccagttc    180
cacaaagaga cttcttagca tctccaagat tgatcgtcat ccgttctttt gacgtcaaca    240
agccaggtgc agaaattgat gatttgaagg gtggtgttgc aggtggttc                289

<210> SEQ ID NO 41
<211> LENGTH: 289
<212> TYPE: DNA
<213> ORGANISM: Candida Kefyr

<400> SEQUENCE: 41
ttattcttca gaacaaggtg gatctaatga gagaagactc cgctctagag catcaaaaat      60
ctattttgaa gtttatcaga ggtactattg ccgatggtgc accaattgtt ccaatttctg    120
ctcaattgaa gtacaatatt gatgccgtta acgaatttat cgttaagagt atcccagttc    180
cacaaagaga cttcttagca tctccaagat tgatcgtcat ccgttctttt gacgtcaaca    240
agccaggtgc agaaattgat gatttgaagg gtggtgttgc aggtggttc                289

<210> SEQ ID NO 42
<211> LENGTH: 289
<212> TYPE: DNA
<213> ORGANISM: Candida Kefyr

<400> SEQUENCE: 42
ttattcttca gaacaaggtg gatctaatga gagaagactc cgctctagag catcaaaaat      60
ctattttgaa gtttatcaga ggtactattg ccgatggtgc accaattgtt ccaatttctg    120
ctcaattgaa gtacaatatt gatgccgtta acgaatttat cgttaagagt atcccagttc    180
cacaaagaga cttcttagca tctccaagat tgatcgtcat ccgttctttt gacgtcaaca    240
agccaggtgc agaaattgat gatttgaagg gtggtgttgc aggtggttc                289

<210> SEQ ID NO 43
<211> LENGTH: 277
<212> TYPE: DNA
<213> ORGANISM: Candida lusitaniae

<400> SEQUENCE: 43
acaaggtcga cttgatgaga gaggagctgg cgttggagca ccagaaatcc attttgagtt      60
tcatccgagg caccatcgcc gatggcgccc ctatcgtgcc tatctcggcc caattgaagt    120
acaacattga cgctgtcaac cagatcatct gcgactacat tcccgtgcct cctcgagact    180
ttatggcgtc gccccgtttg attgtcatta gatctttcga tgtgaacaag ccaggtgccg    240
agattgacga cttgaaaggt ggtgttgcag gtggttc                            277

<210> SEQ ID NO 44
<211> LENGTH: 303
<212> TYPE: DNA
<213> ORGANISM: S.cifferii

<400> SEQUENCE: 44
```

```
attgcaacat gttatcattc tgcaaaacaa ggtggatctc atgaaggagg agtccgccct    60
cgagcatcac aagagcattc tcaagttcat tcgaggcacc attgccgacg atccccagt   120 tatccccatt tctgcccaat tgaagtacaa cattgacgct gtcaacgagt tcattgtgtc   180
caagatcccc atcccgtca gagatttcca ggcaacccca cgattgattg tcattagatc    240
attcgatatc aaccggcccg gttccgaaat cgacgagctc cgtggtggtg ttgcaggtgg   300
ttc                                                                 303
```

<210> SEQ ID NO 45
<211> LENGTH: 286
<212> TYPE: DNA
<213> ORGANISM: S.cifferii

<400> SEQUENCE: 45

```
tcatgcaaaa taaggtggat ctcatgaagg aggagtccgc cctcgagcat cacaagagca    60
ttctcaagtt cattcggggc acaattgccg acggatcccc agttatcccc atttctgcac   120
agctgaagta caacattgat gctgtcaatg agttcattgt ttccaagatc ccaatcccag   180
tcagagattt ccaggccacc ccacgattga ttgtcattag atccttcgat attaaccgtc   240
caggttccga aatcgacgag cttcgtggcg tgttgcagg tggttc                   286
```

<210> SEQ ID NO 46
<211> LENGTH: 276
<212> TYPE: DNA
<213> ORGANISM: Candida utilis

<400> SEQUENCE: 46

```
acaggtggat ttgatgcgtc cagactctgc cttggagcat gagaagtcga ttttgaagtt    60
catcagaggt accattgccg atggtgctcc aatcgtccca atctctgctc aattgaaata   120
caacattgat gctgtcaacg aattcatcgt caagactatc ccagtgccac caagagactt   180
cagtgcctct ccaagactca ttgtgatccg ttcttttgac gttaacaaac caggtgccga   240
aattgacgac ttgaaaggtg tgttgcagg tggttc                              276
```

<210> SEQ ID NO 47
<211> LENGTH: 273
<212> TYPE: DNA
<213> ORGANISM: Candida viswanathii

<400> SEQUENCE: 47

```
ggtcgatttg atgagggaag agtccgcctt ggagcacgag aaatccattc tccaattcat    60
cagaggtacc attgccgaca atgctcctat tgtgccaatt tcggcgcagt tgaagtacaa   120
catcgacgcc gtgaaccagt ttattgtcaa ctacatccca gtgccattga gacttttc     180 tgcatctcca agattgatag tcatcagatc ctttgatgtc aacaagccag gttcggacgt   240
cgaagagttg aaaggtggtg ttgcaggtgg ttc                                273
```

<210> SEQ ID NO 48
<211> LENGTH: 208
<212> TYPE: DNA
<213> ORGANISM: Aspergillus fumigatus

<400> SEQUENCE: 48

```
cgaagcgtcc agaactcccc gagcagcccg acccagagac tctcgatttg tcgacgctca    60
cacctctgtc gcccgaaatt attgcgcgcc aggccacaat caacatcggt actatcggac   120
```

```
acgtcgcaca cggcaagtcg actgttgtga aggctatctc ggaggtgcag actgtccggt    180
tcaaaaatga gttggagcgt aacattac                                       208

<210> SEQ ID NO 49
<211> LENGTH: 172
<212> TYPE: DNA
<213> ORGANISM: Aspergillus fumigatus

<400> SEQUENCE: 49
agactctcga tttgtcgacg ctcacacctc tgtcgcccga aattattgcg cgccaggcca    60
caatcaacat cggtactatc ggacacgtcg cacacggcaa gtcgactgtt gtgaaggcta   120
tctcggaggt gcagactgtc cggttcaaaa atgagttgga gcgtaacatt ac           172

<210> SEQ ID NO 50
<211> LENGTH: 228
<212> TYPE: DNA
<213> ORGANISM: Aspergillus fumigatus

<400> SEQUENCE: 50
agcgccccct gctcctcagc cgaagcgtcc agaactcccc gagcagcccg acccagagac    60
tctcgatttg tcgacgctca cacctctgtc gcccgaaatt attgcgcgcc aggccacaat   120
caacatcggt actatcggac acgtcgcaca cggcaagtcg actgttgtga aggctatctc   180
ggaggtgcag actgtccggt tcaaaaatga gttggagcgt aacattac                228

<210> SEQ ID NO 51
<211> LENGTH: 228
<212> TYPE: DNA
<213> ORGANISM: Aspergillus fumigatus

<400> SEQUENCE: 51
agcgccccct gctcctcagc cgaagcgtcc agaactcccc gagcagcccg acccagagac    60
tctcgatttg tcgacgctca cacctctgtc gcccgaaatt attgcgcgcc aggccacaat   120
caacatcggt actatcggac acgtcgcaca cggcaagtcg actgttgtga aggctatctc   180
ggaggtgcag actgtccggt tcaaaaatga gttggagcgt aacattac                228

<210> SEQ ID NO 52
<211> LENGTH: 209
<212> TYPE: DNA
<213> ORGANISM: Aspergillus fumigatus

<400> SEQUENCE: 52
ccgaagcgtc cagaactccc cgagcagccc gacccagaga ctctcgattt gtcgacgctc    60
acacctctgt cgcccgaaat tattgcgcgc caggccacaa tcaacatcgg tactatcgga   120
cacgtcgcac acggcaagtc gactgttgtg aaggctatct cggaggtgca gactgtccgg   180
ttcaaaaatg agttggagcg taacattac                                     209

<210> SEQ ID NO 53
<211> LENGTH: 226
<212> TYPE: DNA
<213> ORGANISM: Neosartorya fischeri

<400> SEQUENCE: 53 cggccccgt tcctcagccg aagcgtccag aactgcccga gcagcccaac ccagagactc    60
tcgatctgtc gacactgacg cctctgtctc ccgagattat cgcgcgccag ccacaatca   120 acatcggtac tatcggacac gtcgctcacg gcaagtcgac cgtggtgaag gctatttcgg   180
```

```
aggtgcagac tgtccggttc aagaacgagt tggagcgtaa cattac         226

<210> SEQ ID NO 54
<211> LENGTH: 235
<212> TYPE: DNA
<213> ORGANISM: Aspergillus clavatus

<400> SEQUENCE: 54
agggctccat gccccagtt cctcaaccga agcgcccaga actgcccgag cagcctgacc   60
cagagaccat cgatctgtcg aaactgacgc ctctgtcccc cgaaattatc gcgcgccagg  120
ccacgatcaa cattggtacc atcggacacg tcgctcacgg caagtcgacc gtggtgaagg  180
ctatctcgga ggtgcagacg gtccgtttca agaacgagtt ggagcgtaac attac        235

<210> SEQ ID NO 55
<211> LENGTH: 228
<212> TYPE: DNA
<213> ORGANISM: Aspergillus clavatus

<400> SEQUENCE: 55
catgccccca gttcctcaac cgaagcgccc agaactgccc gagcagcctg acccagagac   60
catcgatctg tcgaaactga cgcctctgtc cccgaaatt atcgcgcgcc aggccacgat  120
caacattggt accatcggac acgtcgctca cggcaagtcg accgtggtga aggctatctc  180
ggaggtgcag acggtccgtt tcaagaacga gttggagcgt aacattac               228

<210> SEQ ID NO 56
<211> LENGTH: 206
<212> TYPE: DNA
<213> ORGANISM: Aspergillus clavatus

<400> SEQUENCE: 56
aagcgcccag aactccccga gcagcctgac ccagagacca tcgatctgtc gaaactgacg   60
cctttgtccc ccgaaatcat cgcgcgccag gccacgatca acattggtac catcgggcac  120
gtcgctcacg gcaagtcgac cgtggtgaag gctatttcgg aggtgcaaac tgttcgtttc  180
aagaacgagt tggagcgtaa cattac                                      206

<210> SEQ ID NO 57
<211> LENGTH: 223
<212> TYPE: DNA
<213> ORGANISM: Aspergillus niger

<400> SEQUENCE: 57
ttcctcctcc ccagcccaag cggccagagc tgcccgagca gccgaatccg gagactctgg   60
acctgtccac cctgactcct ttgacccccg aaattattgc gcgccaagcc acaatcaaca  120
ttggcaccat cggtcacgtc gctcacggca agtcgacggt cgttaaggct atctccgagg  180
tccagactgt ccgtttcaag aacgagttgg agcgtaacat tac                    223

<210> SEQ ID NO 58
<211> LENGTH: 223
<212> TYPE: DNA
<213> ORGANISM: Aspergillus niger

<400> SEQUENCE: 58
ttcctcctcc ccagcccaag cggccagagc tgcccgagca gccgaatccg gagactctgg   60
acctgtccac cctgactcct ttgacccccg aaattattgc gcgccaagcc acaatcaaca  120
```

```
ttggcaccat cggtcacgtc gctcacggca agtcgacggt cgttaaggct atctccgagg      180
tccagactgt ccgtttcaag aacgagttgg agcgtaacat tac                       223
```

<210> SEQ ID NO 59
<211> LENGTH: 223
<212> TYPE: DNA
<213> ORGANISM: Aspergillus niger

<400> SEQUENCE: 59

```
ttcctcctcc ccagcccaag cggccagagc tgcccgagca gccgaatccg gagactctgg      60
acctgtccac cctgactcct ttgaccccccg aaattattgc gcgccaagcc acaatcaaca    120
ttggcaccat cggtcacgtc gctcacggca agtcgacggt cgttaaggct atctccgagg    180
tccagactgt ccgtttcaag aacgagttgg agcgtaacat tac                       223
```

<210> SEQ ID NO 60
<211> LENGTH: 223
<212> TYPE: DNA
<213> ORGANISM: Aspergillus niger

<400> SEQUENCE: 60

```
ttcctcctcc ccagcccaag cggccagagc tgcccgagca gccgaatccg gagactctgg      60
acctgtccac gctgactcct ttgaccccccg aaattattgc gcgccaagcc acaatcaaca    120
ttggcaccat cggtcacgtc gctcacggca agtcgacggt cgttaaggct atctccgagg    180
tccagactgt ccgtttcaag aacgagttgg agcgtaacat tac                       223
```

<210> SEQ ID NO 61
<211> LENGTH: 232
<212> TYPE: DNA
<213> ORGANISM: Aspergillus terreus

<400> SEQUENCE: 61

```
aggactctgc tcttcccccc cagccgaagc gcccagagct tcctgaacaa cccaacccag      60
acaccctcga tctgtcgacg cttacccctc tgtcgcccga aatcattgcg cgccaggcca    120
ccatcaacat cggtaccatt ggtcacgtcg ctcacggaaa gtcgacggtc gtcaaggcca    180
tctcagaggt ccagaccgtt cgattcaaga acgagttgga gcgtaacatt ac            232
```

<210> SEQ ID NO 62
<211> LENGTH: 211
<212> TYPE: DNA
<213> ORGANISM: Aspergillus terreus

<400> SEQUENCE: 62

```
agccgaagcg cccagagctt cctgaacaac ccaacccaga caccctcgat ctgtcgacgc      60
ttacccctct gtcgcccgaa attattgcgc gccaggccac catcaacatc ggtaccattg    120
gtcacgtcgc tcacggaaag tcgacggttg tcaaggccat ctcagaggtc cagaccgttc    180
gattcaagaa cgagttggag cgtaacatta c                                    211
```

<210> SEQ ID NO 63
<211> LENGTH: 211
<212> TYPE: DNA
<213> ORGANISM: Aspergillus terreus

<400> SEQUENCE: 63

```
agccgaagcg cccagagctt cctgaacaac ccaacccaga caccctcgat ctgtcgacgc      60
ttacccctct gtcgcccgaa attattgcgc gccaggccac catcaacatc ggtaccattg    120
```

```
gtcacgtcgc tcacggaaag tcgacggttg tcaaggccat ctcagaggtc cagaccgttc    180
gattcaagaa cgagttggag cgtaacatta c                                   211

<210> SEQ ID NO 64
<211> LENGTH: 211
<212> TYPE: DNA
<213> ORGANISM: Aspergillus terreus

<400> SEQUENCE: 64
agccgaagcg cccagagctt cctgaacaac ccaacccaga caccctcgat ctgtcgacgc    60
ttacccctct gtcgcccgaa attattgcgc gccaggccac catcaacatc ggtaccattg    120
gtcacgtcgc tcacggaaag tcgacggttg tcaaggccat ctcagaggtc cagaccgttc    180
gattcaagaa cgagttggag cgtaacatta c                                   211

<210> SEQ ID NO 65
<211> LENGTH: 224
<212> TYPE: DNA
<213> ORGANISM: Aspergillus flavus

<400> SEQUENCE: 65
cccactgttt ctcagcccaa gcggccagag ttgcccgaac agccagaccc cgctaccctt    60
gacctgtcga ccctgacccc tctgtcgccc gaaatcattg cgcgccaggc cactattaac    120
attggtacca tcggacacgt cgctcacgga aagtcaacag tggtcaaggc tatctcagag    180
gttcagactg tccgtttcaa aaacgagttg gagcgtaaca ttac                     224

<210> SEQ ID NO 66
<211> LENGTH: 224
<212> TYPE: DNA
<213> ORGANISM: Aspergillus flavus

<400> SEQUENCE: 66
cccactgttt ctcagcccaa gcggccagag ttgcccgaac agccagaccc cgctaccctt    60
gacctgtcga ccctgacccc tctgtcgccc gaaatcattg cgcgccaggc cactattaac    120
attggtacca tcggacacgt cgctcacgga aagtcaacag tggtcaaggc tatctcagag    180
gttcagactg tccgtttcaa aaacgagttg gagcgtaaca ttac                     224

<210> SEQ ID NO 67
<211> LENGTH: 224
<212> TYPE: DNA
<213> ORGANISM: Aspergillus flavus

<400> SEQUENCE: 67
cccactgttt ctcagcccaa gcggccagag ttgcccgaac agccagaccc cgctaccctt    60
gacctgtcga ccctgacccc tctgtcgccc gaaatcattg cgcgccaggc cactattaac    120
attggtacca tcggacacgt cgctcacgga aagtcaacag tggtcaaggc tatctcagag    180
gttcagactg tccgtttcaa aaacgagttg gagcgtaaca ttac                     224

<210> SEQ ID NO 68
<211> LENGTH: 213
<212> TYPE: DNA
<213> ORGANISM: Aspergillus versicolor

<400> SEQUENCE: 68
tcagccgaaa cgaccagagc taccggagca gcccaaccca gacaccctcg acctgaccac    60
```

```
attaactccc ctgtccccgg aaattattgc ccgccaggcc acgatcaaca tcggcaccat      120
tggtcacgtc gctcacggaa agtcaacggt ggtgaaggct atctcagaag tccagactgt      180
cagatttaag aatgagttgg agcgtaacat tac                                   213

<210> SEQ ID NO 69
<211> LENGTH: 213
<212> TYPE: DNA
<213> ORGANISM: Aspergillus versicolor

<400> SEQUENCE: 69
tcagccgaaa cgaccagagc taccggagca gcccaaccca gacaccctcg acctgaccac       60
attaactccc ctgtccccgg aaattattgc ccgccaggcc acgatcaaca tcggcaccat      120
tggtcacgtc gctcacggaa agtcaacggt ggtgaaggct atctcagaag tccagactgt      180
cagatttaag aatgagttgg agcgtaacat tac                                   213

<210> SEQ ID NO 70
<211> LENGTH: 204
<212> TYPE: DNA
<213> ORGANISM: Aspergillus nidulans

<400> SEQUENCE: 70
acgaccggaa ctaccggagc aacccaaccc agaaacgctc gacctgtcta cactaactcc       60
tctgtcacct gagattatcg cccgccaggc tacgattaac atcggtacca ttggccacgt      120
cgctcacggt aagtcaacgg tggtgaaggc tatttcagag gttcaaactg tccgatttaa      180
gaacgagttg gagcgtaaca ttac                                             204

<210> SEQ ID NO 71
<211> LENGTH: 204
<212> TYPE: DNA
<213> ORGANISM: Aspergillus nidulans

<400> SEQUENCE: 71
acgaccggaa ctaccggagc aacccaaccc agaaacgctc gacctgtcta cactaactcc       60
tctgtcacct gagattatcg cccgccaggc tacgattaac atcggtacca ttggccacgt      120
cgctcacggt aagtcaacgg tggtgaaggc tatttcagag gttcaaactg tccgatttaa      180
gaacgagttg gagcgtaaca ttac                                             204

<210> SEQ ID NO 72
<211> LENGTH: 227
<212> TYPE: DNA
<213> ORGANISM: Aspergillus nidulans

<400> SEQUENCE: 72
ttcatacctg tttctcagcc gaaacgaccg gaactaccgg agcaacccaa cccagaaacg       60
ctcgacctgt ctacactaac tcctctgtca cctgagatta tcgcccgcca ggctacgatt      120
aacatcggta ccattggcca cgtcgctcac ggtaagtcaa cggtggtgaa ggctatttca      180
gaggttcaaa ctgtccgatt taagaacgag ttggagcgta acattac                    227

<210> SEQ ID NO 73
<211> LENGTH: 227
<212> TYPE: DNA
<213> ORGANISM: Aspergillus nidulans

<400> SEQUENCE: 73
ttcatacctg tttctcagcc gaaacgaccg gaactaccgg agcaacccaa cccagaaacg       60
```
cttgacctgt ctacactaac tcctttgtca cctgagatta tcgcccgcca ggctacgatt    120
aacatcggta ccattggtca cgtcgctcac ggtaagtcaa cggtggtgaa ggctatttca    180
gaggttcaaa ctgtccgatt taagaacgag ttggagcgta acattac                  227

<210> SEQ ID NO 74
<211> LENGTH: 1605
<212> TYPE: DNA
<213> ORGANISM: Candida albicans

<400> SEQUENCE: 74
atgtcatacg acgatataga aaatgccact cctgatattg ttattgggag tactatagag    60
gaacctgaag aagattacca agtggaaagt gacaatgagt tacaagccgc agaccatgag   120
tcatcgcaaa taaatgaaga atcagccaaa ggcaaaaagt cagttgcatt tactggattg   180
gatgaagacg aggaaaatgc agaggaattg gccagaaagg agtttgaaga aggtggtgga   240
ttgcctgaac aaccagaaaa cccagatttc aatgagttaa caccttatc tcccgagatt    300 atcaacaggc aagccaccat taatattggt accattggtc atgtcgccca cgggaagtct   360
actgttgtca gggctatctc tggtgtccag accgttcgtt tcaaggatga attagaaaga   420
aacattacta tcaagttagg ttacgccaat gccaaaattt acaaatgtga taacccagag   480
tgtccagaac cagattgtta cagatcattc aaatcagata aggaaataag accaaaatgt   540
caaagagctg gctgtgacgg tcgctacaaa ttgttaagac atgtctcttt tgttgattgt   600
ccaggacatg atattttgat gagtactatg ttgtcaggtg ctgccgtgat ggatgccgcc   660
ttgttgttga ttgccggtaa tgaaagttgt ccacaacccc agacttctga gcatttggct   720
gccattgaaa ttatgaaatt gaaacatgtt attattttgc aaaataaagt tgatttgatg   780
agagaagaat cagccttgga acacgaaaaa tctatcattc agtttattag aggtacaatt   840
gccgataatg ctccgatcgt gcctatttct gctcaattga atacaacat tgatgcagtg    900 aatcaattta ttgttaacta catacctgtg ccaatgagag actttactgc ttcaccaaga   960
ttgatcgtta tcagatcttt cgatgtgaac aagcctggtg cagatgtaga cgaattgaaa  1020
ggaggtgttg caggtggttc tatttttgact ggtgttttta agattggtga tgagatcgag  1080
attagacctg gtatcgtcac caaagatgat caaggaaaga ttcaatgtaa acctatattc  1140
tcgaacgtgg tttccttgtt tgctgagcat aacgatttga aatttgctgt tcctggtggt  1200
ttgattggtg ttggtactaa agttgatcct acgttgtgta gggctgatag attggttggt  1260
caagttgttg gtgcaaaagg aaacttgccc tctatttacg ctgatattga gataaactat  1320
ttcctattaa gaagattgtt gggtgtcaaa actgaaggtc aaaagcaagg tgctaaagtt  1380
cgtaagttgg aacaatctga agtgttgatg gtaaatattg gttctactgc aactggtgct  1440
agagtggttg ctgttaaagc agatatggct cgtttacaat tgactacacc agcctgtaca  1500
gaaatcaacg aaaaaattgc gttgtctaga cgtattgaaa agcattggcg tttgattggt  1560
tgggccacta tcaagaaagg tacagcatta gaaccaattt cttaa                   1605

<210> SEQ ID NO 75
<211> LENGTH: 1605
<212> TYPE: DNA
<213> ORGANISM: Candida albicans

<400> SEQUENCE: 75
atgtcatacg acgatataga aaatgccact cctgatattg ttattgggag tactatagag    60

```
gaacctgaag aagattacca agtggaaagt gacaatgagt tacaagccgc agaccatgag      120
tcatcgcaaa taaatgaaga atcagccaaa ggcaaaagt  cagttgcatt tactggattg      180
gatgaagacg aggaaaatgc agaggaattg ccagaaagg  agtttgaaga aggtggtgga      240
ttgcctgaac aaccagaaaa cccagatttc aatgagttaa cacctttatc tcccgagatt      300
atcaacaggc aagccaccat taatattggt accattggtc atgtcgccca cgggaagtct      360
actgttgtca gggctatctc tggtgtccag accgttcgtt tcaaggatga attagaaaga      420
aacattacta tcaagttagg ttacgccaat gccaaatttt acaaatgtga tacccagag       480 tgtccagaac cagattgtta cagatcattc aaatcagata aggaaataag accaaaatgt      540
caaagagctg gctgtgacgg tcgctacaaa ttgttaagac atgtctcttt tgttgattgt      600
ccaggacatg atattttgat gagtactatg ttgtcaggtg ctgccgtgat ggatgccgcc      660
ttgttgttga ttgccggtaa tgaaagttgt ccacaacccc agacttctga gcatttggct      720
gccattgaaa ttatgaaatt gaaacatgtt attattttgc aaaataaagt tgatttgatg      780
agagaagaat cagccttgga acacgaaaaa tctatcattc agtttattag aggtacaatt      840
gccgataatg ctccgatcgt gcctatttct gctcaattga aatacaacat tgatgcagtg      900
aatcaattta ttgttaacta catacctgtg ccaatgagag actttactgc ttcaccaaga      960
ttgatcgtta tcagatcttt cgatgtgaac aagcctggtg cagatgtaga cgaattgaaa     1020
ggaggtgttg caggtggttc tattttgact ggtgtttttg agattggtga tgagatcgag     1080
attagacctg gtatcgtcac caaagatgat caaggaaaga ttcaatgtaa acctatattc     1140
tcgaacgtgg tttccttgtt tgctgagcat aacgatttga aatttgctgt tcctggtggt     1200
ttgattggtg ttggtactaa agttgatcct acgttgtgta gggctgatag attggttggt     1260
caagttgttg gtgcaaaagg aaacttgccc tctatttacg ctgatattga gataaactat     1320
ttcctattaa gaagattgtt gggtgtcaaa actgaaggtc aaaagcaagg tgctaaagtt     1380
cgtaagttgg aacaatctga agtgttgatg gtaaatattg ttctactgc  aactggtgct     1440 agagtggttg ctgttaaagc agatatggct cgtttacaat tgactacacc agcctgtaca     1500
gaaatcaacg aaaaaattgc gttgtctaga cgtattgaaa agcattggcg tttgattggt     1560
tgggccacta tcaagaaagg tacagcatta gaaccaattt cttaa                     1605
```

<210> SEQ ID NO 76
<211> LENGTH: 1557
<212> TYPE: DNA
<213> ORGANISM: Candida glabrata

<400> SEQUENCE: 76

```
atgtctgatt tgcaagatca agagccaact attattatca atggtgatct tccaccagta       60
gaagaagagg aagtctatga gcaggaagag caagaggaag ttgttgagga aagccaaag      120 aagaaagttg cctttaccgg tctagaggat ggtgaatctg aggaagaaa  gagaaagaga      180 gagtttgaag aaggtggtgg attgccagag cagccagaaa acccagactt tactaagttg      240 aaccccacttt ctgctgagat tattaacaga caagctacta tcaacatcgg tactattggt      300
catgtcgctc acggtaagtc tactgttgtc agagccatct ctggtgtcca aaccgttcgt      360
ttcaaggatg agttggaacg taacattact atcaagctgg ttatgccaa  tgctaagata      420 tataagtgtc aagagcctac atgtccagaa ccagactgtt acagatcttt caagtctgac      480
aaagaaatta atccaaagtg tcaaagacca ggttgcccag gccgttacaa acttgttcgt      540
cacgtctctt tcgtcgattg tccaggtcac gatattctaa tgagtactat gttgtccggt      600
```

```
gccgctgtca tggacgcagc cttgttattg atcgccggta atgaatcttg tccacaacct    660
caaacttctg aacatttggc tgccattgaa atcatgaagt taaagcacgt tattattcta    720
cagaacaagg tcgatttaat gcgtgaagaa agcgcactag aacatgaaaa gtctatcctg    780
aaatttatca gaggtactat tgctgacggt gctccaattg tcccaatttc cgctcaattg    840
aaatacaaca tcgatgcagt caatgaattt atcgtgaaga ctatccctgt tccaccaaga    900
gatttcatgc tttctccacg tttgattgtc attcgttctt tcgatgttaa caagccaggt    960
gctgaaatcg atgatttgaa gggtggtgtt gcaggtggtt ccatcttgaa cggtgtgttc   1020
aagttgggtg atgagattga aattagacca ggtattgtca ctaaggatga taagggtaag   1080
atccaatgta agccaatttt ctccaacatt gtctctctat tgctgaaca aaatgacttg    1140 aagtttgcag tcccaggtgg tctgattggt gttggtacaa aggtcgatcc taccttatgt   1200
agagctgatc gtcttgtcgg tcaagttgtc ggtgccaagg gtcacctacc aagcatttac   1260
acagatattg aaatcaacta cttcctactg cgtcgtctat taggtgttaa gactgagaaa   1320
caagccaagg tcagaaagct ggttgccaac gaagttctta tggttaacat tggttctact   1380
gccactggtg cccgtgtcgt tgctgtcaag gctgatatgg ctagattgca actaacatcc   1440
ccagcatgta cagaaatcaa tgaaaagatt gctctctcta gacgtattga caagcactgg   1500
cgtttaattg gttgggctac aatcaagaaa ggtaccactt tggaaccagt tgtctaa      1557

<210> SEQ ID NO 77
<211> LENGTH: 1551
<212> TYPE: DNA
<213> ORGANISM: Aspergillus fumigatus

<400> SEQUENCE: 77
atggctacca acggcgattt taccgacgat gaatcgcagc ctggctctcc catgttggat     60
gcggcgaacg gccaggatga tattgaagaa caggaacgtc ttgacgtgga agagaagccc    120
cttaagtctg cgatgaagaa aggtgcagcg cccctgctc ctcagccgaa gcgtccagaa     180
ctccccgagc agcccgaccc agagactctc gatttgtcga cgctcacacc tctgtcgccc    240
gaaattattg cgcgccaggc cacaatcaac atcggtacta tcggacacgt cgcacacggc    300
aagtcgactg ttgtgaaggc tatctcggag gtgcagactg tccggttcaa aaatgagttg    360
gagcgtaaca ttaccatcaa gcttggttat gccaacgcga gatctacaa gtgcgacaac    420 cctgggtgcc gcgcccgac gtgcttcaag agttacaaga gtgagaagga gatcgaccct    480
ccatgtgaga gagaaggatg cacaggtcgt tacagattgt tgagacatgt ctcgttcgtt    540
gactgccctg gcacgatat tctcatgagt accatgttgt caggtgccgc cgtcatggac    600 gccgccettt tgctgattgc cggaaacgaa gcttgcccccc agcctcagac ttcggagcac    660
ttagcagcta ttgaaatcat gaagctcagc catatcatca ttctgcagaa caaggttgat    720
ctgatgaggg aagacggtgc tctgcaacat taccaatcaa cctgaagtt cattcgtggt    780 actgttgccg atggctctcc tatcattccc atctctgctc agctcaagta caacatcgac    840
gctgtcaacg aataccttgt ctcgcacatc ccagttcccg tccgtgactt cactgcttcg    900
cctcacatga ttgtcattcg ttccttcgac gtcaacaaac ccggtgcgga gatcgatgag    960
ttgaagggtg gtgttgcagg tggctctatc ctcactggtg tgctgaagct gaacgacgag   1020
attgaaattc gccccggtct cgttaccaag gatgagaacg gaaagattca gtgccgcccc   1080
atcttctccc gtgtcgtctc gctcttcgct gagcacaacg atctgaagtt cgctgtccct   1140
```

```
ggtggtctaa tcggtgtcgg aacccgtgtc gaccctaccc tgtgccgtgc cgatcgtctt    1200
gttggtttcg tcctgggtca ccgtggccgt ttgccagcca tctacactga actggaggtc    1260
aactacttcc tcctgcgtcg tctgctcggt gtcaagaccg ccgacggcaa gcaggccaag    1320
gtcgccaagc tcaccaagaa cgaagtcctc atggttaaca tcggctctac ggctactggt    1380
gctaaggtta tgggtgtgaa ggctgatgct gccaagctca gcttgaccag cccggcttgt    1440
acagagattg gagagaagat tgctatcagc cggagaattg acaagcattg gcgtctgatc    1500
ggctgggcca acattgtcgc tggcaacact cttgagccca ttctgaacta g             1551

<210> SEQ ID NO 78
<211> LENGTH: 1551
<212> TYPE: DNA
<213> ORGANISM: Neosartorya fischeri

<400> SEQUENCE: 78
atggctacca acggcgattt taccgacgat gaatcgcagc ctggctctcc catgctggat     60
gcggcgaacg gccaggatga cattgaagaa caggagcctc ttgacgtgga agagaagccc    120
ctcaagtctg caatgaagaa aggttcagcg ccccctgctc ctcagccgaa gcgtccagaa    180
ctccccgagc agcccgaccc agagactctc gaattgtcga cactcacgcc tctgtcgccc    240
gagattattg cgcgccaggc cacaatcaac atcggtacta tcggacacgt cgctcacggc    300
aagtcgactg tggtgaaggc tatttcggag gtgcagactg tccggttcaa aaatgagttg    360
gagcgtaata ttaccatcaa gcttggttat gccaacgcga agatctacaa gtgcgacaac    420
cctgagtgcc cgcgcccgac gtgcttcaag agttacaaga gtgagaagga gatcgaccct    480
ccatgtgaga gagaaggatg cacaggtcgt tacagattgt tgagacatgt ctcgttcgtt    540
gactgccctg gcacgatat ctcatgagt accatgttgt caggtgccgc cgtcatggac      600
gccgcccttt tgctgattgc cggaaacgaa gcttgccccc agcctcagac ttcggagcac    660
ttggcagcta ttgaaatcat gaagctcagc cacatcatca ttctgcagaa caaggttgat    720
ctgatgaggg aagacggtgc tcttcaacat taccaatcaa tcctgaagtt cattcgtggt    780
actgttgccg atggttctcc tatcattccc atctctgctc agctcaagta caacatcgac    840
gctgtcaacg aataccttgt ctcgcacatc ccagttcccg tccgtgactt cactgcttcg    900
cctcacatga ttgtcatccg ttccttcgac gtcaacaagc ccggtgcgga gatcgatgag    960
ttgaagggtg gtgttgcagg tggctctatc ctcactggtg tgctgaagct gaacgacgag   1020
attgagattc gccccggtct cgttaccaag gatgagaacg gaaagattca gtgccgcccc   1080
atcttctccc gtgtcgtttc gctcttcgct gagcacaacg atctgaagtt cgctgtccct   1140
ggtggtctga tcggtgtcgg aacccgtgtc gaccctaccc tgtgccgtgc cgatcgtctc   1200
gttggtttcg tcctgggtca ccgtggccgt ttgccggcca tctacactga actggaggtc   1260
aactacttcc tcctgcgtcg tctgctcggt gtcaagaccg ccgacggcaa gcaggccaag   1320
gtcgccaagc tcaccaagaa cgaggtcctc atggttaaca tcggctctac ggctactggt   1380
gctaaggtta tgggtgtgaa ggctgatgct gccaagctca gcttgaccag cccggcttgt   1440
acagagattg gagagaagat tgctatcagc cggagaattg acaagcattg gcgtctgatc   1500
ggctgggcca atattgtcgc tggcaacact cttgagccca ttctgaacta g            1551

<210> SEQ ID NO 79
<211> LENGTH: 1485
<212> TYPE: DNA
<213> ORGANISM: Aspergillus clavatus
```

<400> SEQUENCE: 79

```
atgggtcatt atgaaattga agaacaagag cctcttgatg tcgaggagaa ggccctcaag      60
tcttcgatga agaagggctc catgccccca gttcctcaac cgaagcgccc agaactgccc     120
gagcagcctg acccagagac catcgatctg tcgaaactga cgcctctgtc ccccgaaatt     180
atcgcgcgcc aggccacgat caacattggt accatcggac acgtcgctca cggcaagtcg     240
accgtggtga aggctatctc ggaggtgcag acggtccgtt tcaagaacga gttggagcgg     300
aatattacca tcaagctggg ttatgccaac gccaagatct acaagtgcga cagccctgag     360
tgccctcggc cgacatgcta caagagttac aagagtgaga aggaggtcga ccctccttgc     420
gaaagagaag gatgcacagg tcactacaga ctgctgagac acgtttcttt cgttgactgc     480
cccggtcacg acattctcat gagcactatg ttgtcaggcg ccgccgtcat ggacgccgcc     540
cttcttttga ttgccggaaa cgaagcctgc cctcagcccc agacctcgga gcacttggca     600
gccattgaga tcatgaagct cagccacatt atcatcctgc agaacaaggt cgatctgatg     660
agagaggatg gagctttgca acattaccag tcgattctga agttcatccg tggtactgtc     720
gctgatggct cgcccatcat tcctatctct cgcagctca agtacaacat tgatgctgtt      780
aacgaatacc ttgtttcgca catccccgtc cccgtccgtg acttcactgc ttcccctcac     840
atgatcgtca tccgttcctt cgacgtcaac aagcccggtg cggagattga tgagctgaag     900
ggtggtgttg ccggtggctc tatcctgact ggtgtgctca agttgaatga tgagatcgag     960
atccgccctg gtctcgttac caaggacgag aacggcaaga ttcagtgccg tcccatcttc    1020
tcgcgtgttg tctcgctctt tgccgagcac aacgacctga agtttgctgt tcctggtggt    1080
ctgatcggtg tcggcacccg tgtcgaccct actctgtgcc gtgctgatcg tctcgttggt    1140
ttcgtcctgg gtcaccgtgg tcgcctgccc gctatttaca ctgaactgga ggtcaactac    1200
ttcttgctgc gtcgtctgct cggtgtcaag accgccgatg gcaagcaggc taaggttgcc    1260
aagctgacca agaacgaggt tctcatggtc aacatcggat cgacagccac tggtgccaag    1320
gttatgggtg tgaaggccga cgctgccaag ctcagcttga ccagccctgc ctgcacagaa    1380
attggcgaga agattgccat cagccgaaga atcgacaagc attggcgtct gatcggttgg    1440
gccaacattg tcgctggtaa cactcttgag cctattctga actag                    1485
```

<210> SEQ ID NO 80
<211> LENGTH: 1534
<212> TYPE: DNA
<213> ORGANISM: Aspergillus terreus

<400> SEQUENCE: 80

```
atggctacca acggcgattt caccgacgat gaatcccagc ccggttcccc cgtcatggag      60
cccaacggcc agtacgacat tgaagaacag gagcctctcg accagcccct gaagtcggcg     120
atgaagaagg actctgctct tttcccccag ccgaagcgcc cagagcttcc tgaacaaccc     180
aacccagaca ccctcgatct gtcgacgctt accctctgt cgcccgaaat tattgcgcgc      240
caggccacca tcaacatcgg taccattggt cacgtcgctc acggaaagtc gacggttgtc     300
aaggccatct cagaggtcca gaccgttcga ttcaagaacg agttggaacg gaatattacg     360
attaagctgg gttatgccaa cgccaagatc tacaagtgcg acaaccccga gtgccctcgg     420
ccgacttgtt acaagagttt caagagtgag aaggaggtcg accgccatg tgagagagat      480
ggctgcacag gtcgttaccg tctactgaga cacgtctcct tgtcgactg ccccggtcac      540
```

```
gatattctca tgagtacctg ttgtctggtg ccgccgtcat ggacgctgcc cttctcctga    600
ttgccggaaa cgaaacctgc ccccagcctc agacctcgga gcacttggct gctattgaga    660
tcatgaagct gagtcatatc attatcctgc agaacaaggt cgatctgatg cgcgaggacg    720
gtgccctgca gcactaccag tcgatcctga agttcatccg tggtactgtg gcagacggct    780
ctcccattat ccccatctcc gcccagctga agtacaacat cgatgcggtc aacgagtacc    840
tcgtgtcgca catccccgtc ccgtccgtg actttaccgc ctctcctcac atgattgtca     900
ttcgctcctt cgacgtcaac aagcccggtg ccgagattga tgatctgaag ggtggtgtcg    960
ctggtggttc catcctgaca ggtgtgctga agctgaacga cgagatcgaa atccgtcccg   1020
gtctggtcac gaaggacgag aacggcaaga tccagtgccg tcccatcttc tctcgcgtgg   1080
tctccctatt cgccgagcac aacgacctca agttcgcgtg cccggcggtc ttatcggtgt   1140
tggtactcgc gttgacccta ccctctgccg tgcggatcgt cttgttggtt tcgtcctggg   1200
tcaccgtggt cgcctgcctg ctatctacac tgagctggag gttaactact tcttgctgcg   1260
tcgtctgctc ggtgtgaaga ccgccgacgg aaagcaggct aaggtcgcca agctggccaa   1320
gaacgaagtt ctgatggtga acattggatc tacgccacc ggtgccaagg tgatgggtgt    1380
gaaggctgat gctgccaagc tcagcttgac cagccctgcc tgtaccgaga tcggagagaa   1440
gatcgccatc agtcggagaa ttgagaagca ctggcgtctg atcggttggg ccaacattgt   1500
tgccggtaac accctggagc ccatcctgaa ctaa                               1534

<210> SEQ ID NO 81
<211> LENGTH: 1542
<212> TYPE: DNA
<213> ORGANISM: Aspergillus oryzae

<400> SEQUENCE: 81
atggctgcca acgcgattt ttccgatgat gaatcccagc cgggatcccc catgctgaat    60
gcgaacggcc atgatgatat tgaagaacaa gagcccctcg accaagagga gaagcctctc    120
aagtctgcga tgaagagtgt accccctgtt tctcagccca gcggccaga gttgcccgaa    180
cagccagacc ccgctaccct tgacctgtcg accctgaccc ctctgtcgcc cgaaatcatt    240
gcgcgccagg ccactattaa cattggtacc atcggacacg tcgctcacgg aaagtcaaca    300
gtggtcaagg ctatctcaga ggttcagact gtccgtttca aaacgagtt ggagcgaaac     360
attacaatca agctgggcta cgccaacgcc aagatctaca agtgcgacaa ccccgagtgt    420
cctcgcccaa catgcttcaa gagttttcaag agtgagaagg agatcgaccc tccatgtgag    480
agagatgggt gcacaggacg ttataggctg ttgagacatg tctccttcgt tgactgcccc    540
ggtcacgata ttctgatgag taccatgttg tcaggtgccg ccgtcatgga cgcagctctt    600
cttctgattg ccggaaacga aacttgccct cagcctcaaa cctcggaaca tttggcagct    660
atcgagatta tgaagcttag ccatattatc atcttgcaaa ataaggttga tctgatgagg    720
gaagaaggag ctttttcagca ttaccaatcg attctgaagt tcatccgtgg tactgttgct    780
gatggctctc ctattatccc catctccgct cagctgaagt acaacattga tgctgtcaac    840
gaataccttg ttcccacat ccctgtccct gtccgtgatt tcaccgcttc gccacacatg     900
atcgtcatcc gttcattcga tgtgaacaag cctggtgccg agattgatga gctgaagggc    960
ggtgttgctg gtggttccat tctgactggt gtgcttaagc ttaacgacga ggtggaaatc   1020
cgtcccggtc tcgtaaccaa ggacgagaac ggcaagattc agtgccggcc catcttctcg   1080
cgggttgttt ctctcttcgc tgagcacaac gacctgaaat ttgctgttcc tggtggtctt   1140
```

```
attggtgtcg gtacccgtgt ggaccctact ctgtgccgtg ccgatcgtct tgtcggtttc    1200
gtcctgggcc atcgcggacg tctgcccgcc atttacaccg aactggaggt caactatttc    1260
ttgctgcgcc ggttgttggg tgtgaagacc gccgacggca agcaggccaa ggttgctaag    1320
ctgagcaaga acgaggttct gatggtcaac atcggttcta cggccaccgg tgctaaggtc    1380
atgggcgtca aggccgatgc tgcaaagctg agcttgacca gccctgcttg taccgaaatt    1440
ggcgagaaga ttgccatttc tcgcagaatc gacaagcact ggcgtctgat tgggtgggct    1500
aacattgttg ccggtaacac cctcgaaccc atcctgaact aa                        1542
```

<210> SEQ ID NO 82
<211> LENGTH: 1479
<212> TYPE: DNA
<213> ORGANISM: Aspergillus niger

<400> SEQUENCE: 82

```
atggctgacg atgacatcga agagcaagag cccctcgacc aggaggccaa gcctctgaag      60
tctgcgatga agaaggaagt tcctcctccc cagcccaagc ggccagagct gcccgagcag    120
ccgaatccgg agactctgga cctgtccacc ctgactcctt tgaccccga aattattgcg      180 cgccaagcca caatcaacat tggcaccatc ggtcacgtcg ctcacggcaa gtcgacggtc    240
gttaaggcta tctccgaggt ccagactgtc cgtttcaaga acgagttgga gcgaaacatt    300
acgatcaagc tgggttatgc caacgcaaag atctacaagt gcgacaaccc cgagtgccct    360
aggccgacat gctttaagag ctttaagagt gagaaggaag tcgacccgcc ttgtgagagg    420
gatggctgcg gtggccgcta cagactgttg agacatgtgt ctttcgtcga ctgccccggt    480
cacgatattc tgatgagtac tatgttgtct ggtgccgccg tcatggacgc tgccctcctc    540
cttattgccg gaaacgaaac ttgccctcaa cctcagactt cggagcactt ggctgccatc    600
gaaatcatga agctcagcca catcatcatt ttgcaaaaca aggtggactt gatgagagag    660
gatggtgccc tgcaacatta ccagtcgatc ttgaagttca tccgtggtac tgtcgccgat    720
ggctctccga tcattcccat ttctgcacag ctcaagtaca acatcgatgc tgtcaacgaa    780
tacctggttt cgcacattcc cgtccccgtc cgcgatttca ccgcttcccc ccacatgatc    840
gtcattcgtt ccttcgatgt gaacaagcct ggtgccgaaa ttgaggagct gaagggtggt    900
gttgccggtg gttcgatctt gactggtgtt ctgaagcaga acgacgagat tgagattcgt    960
cccggtctgg tcaccaagga cgagaacggc aagattcagt gccgtcccat cttctctcgg   1020
gtcatgtccc tctttgccga gcacaacgac ctcaagtttg ccgtccctgg tggtttgatt   1080
ggtgtcggta tcgtgtagac ccctactctg tgccgtgctg atcgtctcgt tggtttcgtc   1140
ctgggtcacc gcggacgcct tcccgctatc tacactgagt tggaagtcaa ctacttcttg   1200
cttcgtcgtc tgctcggtgt caagactgcc gatgcaagc aggccaaggt tgccaagctt   1260
actaagaacg aggttctcat ggtcaacatc ggttctacgg ctaccggagc taaggtcgtg   1320
ggtgtcaagg ctgatgctgc caagctcagc ttgaccagcc ctgcctgtac cgaggtcgga   1380
gagaagattg ccatcagtcg gagaattgag aagcactggc gtctgatcgg ttgggccaac   1440
attgtcgctg gtaacaccct tgagcccatc ctgaactaa                            1479
```

<210> SEQ ID NO 83
<211> LENGTH: 1545
<212> TYPE: DNA
<213> ORGANISM: Aspergillus nidulans

<400> SEQUENCE: 83

```
atggctacca acggcgattt ttcagacgag gagtcccagc ccgggtctcc cattcttaac     60
gccaatggcc aggatgatat ccaagaccaa gagcccctcg agcaggagga gaagcccatc    120
aagtcagcga tgaagaagga cttcatacct gtttctcagc cgaaacgacc ggaactaccg    180
gagcaaccca acccagaaac gctcgacctg tctacactaa ctcctctgtc acctgagatt    240
atcgcccgcc aggctacgat taacatcggt accattggcc acgtcgctca cggtaagtca    300
acggtggtga aggctatttc agaggttcaa actgtccgat ttaagaacga gttggagcga    360
aacattacca tcaagctggg ttatgccaac gcgaaaatct acaagtgcga caccccgct     420
tgccctcggc cgacatgcta caagagctat aagagtgaga aggaaattga tccgccctgt    480
gagagagatg gatgctctgg ccgctaccgt ctcttaagac acgtttcctt cgtcgactgc    540
cctggtcacg acattcttat gagtaccatg ttgtcaggtg ccgctgtcat ggatgctgct    600
cttttgctta tcgctggaaa cgaaacctgt cctcagcccc agacttcgga gcatttggct    660
gctattgaaa tcatgaagct tagccacatc attatccttc aaaacaaggt cgatttgatg    720
agggaagatg gagcgttgca gcattaccag tcgatcttga aatttatccg tggtaccgtt    780
gccgacggct ctcccatcat tcccatctcc gctcagctca agtacaacat cgatgccgtc    840
aacgagtatc tggtttcgca catccccgtg ccagtccgcg atttcacggc atctcctcac    900
atgattgtta tccggtctt cgacgtgaac aagcctggtg cagagattga tgagctaaag    960
ggtggtgtgg ctggtggttc cattttgact ggtgtcctca agttgaacga tgaaatcgaa   1020
attcgaccag gtctcgtcac taaggacgag aacggcaaga tccagtgtcg ccctatcttc   1080
tcgcgggttg tgtctttgtt tgccgaacac aacgacctga aattcgctgt ccccggtgga   1140
ttgatcggtg ttggtactcg tgttgaccct actctttgcc gtgccgatcg cctggttggt   1200
ttcgtcctcg gtcaccgtgg gcgccttccc gctatctaca cagagctaga ggtcaattac   1260
tttttgctgc gccgactttt gggtgtcaag actgccgacg gcaagcaggc caaggtcgcc   1320
aagctggcta agaacgaggt tctcatggtt aatatcggct ctacagctac cggtgcgaag   1380
gtggtcggtg tcaaggctga tgctgctaag ctgagcttga ctagcccagc ctgtactgag   1440
gttggcgaga agattgccat tagtcgaaga attgagaagc actggcgttt gattggttgg   1500
gccaacattg ttgctggtaa caccctcgag cccattgtca actaa                    1545
```

<210> SEQ ID NO 84
<211> LENGTH: 21
<212> TYPE: DNA
<213> ORGANISM: Artificial Sequence
<220> FEATURE:
<223> OTHER INFORMATION: ALEF2

<400> SEQUENCE: 84

```
ataatgctcc gatcgtgcct a                                                21
```

<210> SEQ ID NO 85
<211> LENGTH: 24
<212> TYPE: DNA
<213> ORGANISM: Artificial Sequence
<220> FEATURE:
<223> OTHER INFORMATION: GlabA

<400> SEQUENCE: 85

```
caagagattt catgctttct ccac                                            24
```

```
<210> SEQ ID NO 86
<211> LENGTH: 25
<212> TYPE: DNA
<213> ORGANISM: Artificial Sequence
<220> FEATURE:
<223> OTHER INFORMATION: ParA

<400> SEQUENCE: 86
cgtaaactca ataccagttc cagtc                                          25

<210> SEQ ID NO 87
<211> LENGTH: 26
<212> TYPE: DNA
<213> ORGANISM: Artificial Sequence
<220> FEATURE:
<223> OTHER INFORMATION: TropicA

<400> SEQUENCE: 87
tgtcaattat atcccagttc cattga                                         26

<210> SEQ ID NO 88
<211> LENGTH: 25
<212> TYPE: DNA
<213> ORGANISM: Artificial Sequence
<220> FEATURE:
<223> OTHER INFORMATION: KrusA

<400> SEQUENCE: 88
catgtgtatg gtcaagtcta ttcct                                          25

<210> SEQ ID NO 89
<211> LENGTH: 15
<212> TYPE: DNA
<213> ORGANISM: Artificial Sequence
<220> FEATURE:
<223> OTHER INFORMATION: CEF3F

<400> SEQUENCE: 89
tcagccttgg aacac                                                     15

<210> SEQ ID NO 90
<211> LENGTH: 17
<212> TYPE: DNA
<213> ORGANISM: Artificial Sequence
<220> FEATURE:
<223> OTHER INFORMATION: CEFR1

<400> SEQUENCE: 90
ttggcacagg tatgtag                                                   17

<210> SEQ ID NO 91
<211> LENGTH: 19
<212> TYPE: DNA
<213> ORGANISM: Artificial Sequence
<220> FEATURE:
<223> OTHER INFORMATION: GlabF1

<400> SEQUENCE: 91
tcgtgaagac tatccctgt                                                 19

<210> SEQ ID NO 92
<211> LENGTH: 18
<212> TYPE: DNA
<213> ORGANISM: Artificial Sequence
<220> FEATURE:
<223> OTHER INFORMATION: GlabR1
```

```
<400> SEQUENCE: 92
atcgatttca gcacctgg                                                 18

<210> SEQ ID NO 93
<211> LENGTH: 17
<212> TYPE: DNA
<213> ORGANISM: Artificial Sequence
<220> FEATURE:
<223> OTHER INFORMATION: ParaF1

<400> SEQUENCE: 93
tatcgacgcc gtcaatc                                                  17

<210> SEQ ID NO 94
<211> LENGTH: 17
<212> TYPE: DNA
<213> ORGANISM: Artificial Sequence
<220> FEATURE:
<223> OTHER INFORMATION: ParaR1

<400> SEQUENCE: 94
atcaacgtca gcaccag                                                  17

<210> SEQ ID NO 95
<211> LENGTH: 18
<212> TYPE: DNA
<213> ORGANISM: Artificial Sequence
<220> FEATURE:
<223> OTHER INFORMATION: TropicF1

<400> SEQUENCE: 95
acatcgatgc cgttaacc                                                 18

<210> SEQ ID NO 96
<211> LENGTH: 18
<212> TYPE: DNA
<213> ORGANISM: Artificial Sequence
<220> FEATURE:
<223> OTHER INFORMATION: TropicR1

<400> SEQUENCE: 96
caagtcttcg acatcgga                                                 18

<210> SEQ ID NO 97
<211> LENGTH: 19
<212> TYPE: DNA
<213> ORGANISM: Artificial Sequence
<220> FEATURE:
<223> OTHER INFORMATION: KrusF1

<400> SEQUENCE: 97
cccaatttct gctcagttg                                                19

<210> SEQ ID NO 98
<211> LENGTH: 20
<212> TYPE: DNA
<213> ORGANISM: Artificial Sequence
<220> FEATURE:
<223> OTHER INFORMATION: KrusR1

<400> SEQUENCE: 98
caccaggctt attaacatcg                                               20

<210> SEQ ID NO 99
<211> LENGTH: 1605
```

```
<212> TYPE: DNA
<213> ORGANISM: Candida albicans

<400> SEQUENCE: 99
atgtcatacg acgatataga aaatgccact cctgatattg ttattgggag tactatagag      60
gaacctgaag aagattacca agtggaaagt gacaatgagt tacaagccgc agaccatgag     120
tcatcgcaaa taaatgaaga atcagccaaa ggcaaaaagt cagttgcatt tactggattg     180
gatgaagacg aggaaaatgc agaggaattg gccagaaagg agtttgaaga aggtggtgga     240
ttgcctgaac aaccagaaaa cccagatttc aatgagttaa caccttatc tcccgagatt     300
atcaacaggc aagccaccat taatattggt accattggtc atgtcgccca cgggaagtct     360
actgttgtca gggctatctc tggtgtccag accgttcgtt tcaaggatga attagaaaga     420
aacattacta tcaagttagg ttacgccaat gccaaaattt acaaatgtga tacccagag     480
tgtccagaac cagattgtta cagatcattc aaatcagata aggaaataag accaaaatgt     540
caaagagctg gctgtgacgg tcgctacaaa ttgttaagac atgtctcttt tgttgattgt     600
ccaggacatg atattttgat gagtactatg ttgtcaggtg ctgccgtgat ggatgccgcc     660
ttgttgttga ttgccggtaa tgaaagttgt ccacaacccc agacttctga gcatttggct     720
gccattgaaa ttatgaaatt gaaacatgtt attatttgc aaaataaagt tgatttgatg      780
agagaagaat cagccttgga acacgaaaaa tctatcattc agtttattag aggtacaatt     840
gccgataatg ctccgatcgt gcctatttct gctcaattga atacaacat tgatgcagtg     900
aatcaattta ttgttaacta cataccgtgt ccaatgagag actttactgc ttcaccaaga     960
ttgatcgtta tcagatcttt cgatgtgaac aagcctggtg cagatgtaga cgaattgaaa    1020
ggaggtgttg caggtggttc tattttgact ggtgttttta agattggtga tgagatcgag    1080
attagacctg gtatcgtcac caaagatgat caaggaaaga ttcaatgtaa acctatattc    1140
tcgaacgtgg tttccttgtt tgctgagcat aacgatttga aatttgctgt tcctggtggt    1200
ttgattggtg ttggtactaa agttgatcct acgttgtgta gggctgatag attggttggt    1260
caagttgttg gtgcaaaagg aaacttgccc tctatttacg ctgatattga gataaactat    1320
ttcctattaa gaagattgtt gggtgtcaaa actgaaggtc aaaagcaagg tgctaaagtt    1380
cgtaagttgg aacaatctga agtgttgatg gtaaatattg gttctactgc aactggtgct    1440
agagtggttg ctgttaaagc agatatggct cgtttacaat tgactacacc agcctgtaca    1500
gaaatcaacg aaaaaattgc gttgtctaga cgtattgaaa agcattggcg tttgattggt    1560
tgggccacta tcaagaaagg tacagcatta gaaccaattt cttaa                    1605

<210> SEQ ID NO 100
<211> LENGTH: 1557
<212> TYPE: DNA
<213> ORGANISM: Candida glabrata

<400> SEQUENCE: 100
atgtctgatt tgcaagatca agagccaact attattatca atggtgatct tccaccagta      60
gaagaagagg aagtctatga gcaggaagag caagaggaag ttgttgagga gaagccaaag     120
aagaaagttg cctttaccgg tctagaggat ggtgaatctg aggaagagaa gagaaagaga     180
gagtttgaag aaggtggtgg attgccagag cagccagaaa acccagactt tactaagttg     240
aacccacttt ctgctgagat tattaacaga caagctacta tcaacatcgg tactattggt     300
catgtcgctc acggtaagtc tactgttgtc agagccatct ctggtgtcca aaccgttcgt     360
```

```
ttcaaggatg agttggaacg taacattact atcaagctgg gttatgccaa tgctaagata      420
tataagtgtc aagagcctac atgtccagaa ccagactgtt acagatcttt caagtctgac      480
aaagaaatta atccaaagtg tcaaagacca ggttgcccag gccgttacaa acttgttcgt      540
cacgtctctt tcgtcgattg tccaggtcac gatattctaa tgagtactat gttgtccggt      600
gccgctgtca tggacgcagc cttgttattg atcgccggta tgaatcttg tccacaacct      660 caaacttctg aacatttggc tgccattgaa atcatgaagt taaagcacgt tattattcta      720
cagaacaagg tcgatttaat gcgtgaagaa agcgcactag aacatgaaaa gtctatcctg      780
aaatttatca gaggtactat tgctgacggt gctccaattg tcccaatttc cgctcaattg      840
aaatacaaca tcgatgcagt caatgaattt atcgtgaaga ctatccctgt tccaccaaga      900
gatttcatgc tttctccacg tttgattgtc attcgttctt tcgatgttaa caagccaggt      960
gctgaaatcg atgatttgaa gggtggtgtt gcaggtggtt ccatcttgaa cggtgtgttc     1020
aagttgggtg atgagattga attagacca ggtattgtca ctaaggatga taagggtaag     1080
atccaatgta agccaatttt ctccaacatt gtctctctat ttgctgaaca aaatgacttg     1140
aagtttgcag tcccaggtgg tctgattggt gttggtacaa aggtcgatcc taccttatgt     1200
agagctgatc gtcttgtcgg tcaagttgtc ggtgccaagg tcacctacc aagcatttac     1260 acagatattg aaatcaacta cttcctactg cgtcgtctat taggtgttaa gactgagaaa     1320
caagccaagg tcagaaagct ggttgccaac gaagttctta tggttaacat tggttctact     1380
gccactggtg cccgtgtcgt tgctgtcaag gctgatatgg ctagattgca actaacatcc     1440
ccagcatgta cagaaatcaa tgaaaagatt gctctctcta gacgtattga caagcactgg     1500
cgtttaattg gttgggctac aatcaagaaa ggtaccactt tggaaccagt tgtctaa         1557

<210> SEQ ID NO 101
<211> LENGTH: 303
<212> TYPE: DNA
<213> ORGANISM: Candida parapsilosis

<400> SEQUENCE: 101
gttgaagcac gttattattt tgcaaaacaa agttgattta atgagaaagg agtcagcttt       60
ggaacatgaa aagtccatca ttcagttcat cagaggtact atagctgatg gtgccccaat      120
tgttccaatt tcagcacaat tgaagtataa atcgacgcc gtcaatcaat tcatcgtaaa      180 ctcaataccca gttccagtca gggactttac tgcatcccct aggttaattg ttattaggtc      240
ttttgatgtg aacaaacctg gtgctgacgt tgatgatttg aaaggaggtg ttgcaggtgg      300
ttc                                                                     303

<210> SEQ ID NO 102
<211> LENGTH: 293
<212> TYPE: DNA
<213> ORGANISM: Candida tropicalis

<400> SEQUENCE: 102
gtcatkattt tgcagaacaa ggtcgatttg atgagagaag aatctgcctt ggaacatgag       60
aaatccattc ttcaattcat cagaggtact attgcagaca atgctcctat tgtcccaatt      120
tctgcccaat tgaaatacaa catcgatgcc gttaaccaat ttattgtcaa ttatatccca      180
gttccattga gagacttttc cgcttcccca agattgattg tcatcagatc ttttgatgtc      240
aacaagccag gttccgatgt cgaagacttg aaagggggtg ttgcaggtgg ttc              293
```

```
<210> SEQ ID NO 103
<211> LENGTH: 294
<212> TYPE: DNA
<213> ORGANISM: Candida kruisi

<400> SEQUENCE: 103
tgktgtgatt ktacaaaata aagttgattt gatgaagaaa gaagcagctt tagagcacga      60
aaaatctatt ttgaagttta tcaagggtac tattgctgat ggtgctccta ttatcccaat     120
ttctgctcag ttgaaatata acattgatgc agttaacatg tgtatggtca agtctattcc     180
tgttccaatt agagacttta ccgcagttcc aagattaatg gttattagat ctttcgatgt     240
taataagcct ggtgcagaaa ttgcagattt gaaaggtggt gttgcaggtg gttc           294

<210> SEQ ID NO 104
<211> LENGTH: 16
<212> TYPE: DNA
<213> ORGANISM: Artificial Sequence
<220> FEATURE:
<223> OTHER INFORMATION: EF2_7_FOW

<400> SEQUENCE: 104
agcccaagcg gccaga                                                      16

<210> SEQ ID NO 105
<211> LENGTH: 16
<212> TYPE: DNA
<213> ORGANISM: Artificial Sequence
<220> FEATURE:
<223> OTHER INFORMATION: EF2_8_FOW

<400> SEQUENCE: 105
agccgaagcg cccaga                                                      16

<210> SEQ ID NO 106
<211> LENGTH: 15
<212> TYPE: DNA
<213> ORGANISM: Artificial Sequence
<220> FEATURE:
<223> OTHER INFORMATION: EF2_5_REV

<400> SEQUENCE: 106
ggcctggcgc gcaat                                                       15

<210> SEQ ID NO 107
<211> LENGTH: 15
<212> TYPE: DNA
<213> ORGANISM: Artificial Sequence
<220> FEATURE:
<223> OTHER INFORMATION: EF2_6_REV

<400> SEQUENCE: 107
ggcttggcgc gcaat                                                       15

<210> SEQ ID NO 108
<211> LENGTH: 19
<212> TYPE: DNA
<213> ORGANISM: Artificial Sequence
<220> FEATURE:
<223> OTHER INFORMATION: A.NIG_EF2_1

<400> SEQUENCE: 108
atccggagac tctggacct                                                   19

<210> SEQ ID NO 109
```

```
<211> LENGTH: 18
<212> TYPE: DNA
<213> ORGANISM: Artificial Sequence
<220> FEATURE:
<223> OTHER INFORMATION: A.TERR_EF2_1

<400> SEQUENCE: 109
cgacgcttac ccctctgt                                                 18

<210> SEQ ID NO 110
<211> LENGTH: 17
<212> TYPE: DNA
<213> ORGANISM: Artificial Sequence
<220> FEATURE:
<223> OTHER INFORMATION: A.FLAV_EF2_1

<400> SEQUENCE: 110
cagaccccgc taccctt                                                  17

<210> SEQ ID NO 111
<211> LENGTH: 17
<212> TYPE: DNA
<213> ORGANISM: Artificial Sequence
<220> FEATURE:
<223> OTHER INFORMATION: A.FUM_EF2_1

<400> SEQUENCE: 111
acgctcacac ctctgtc                                                  17

<210> SEQ ID NO 112
<211> LENGTH: 18
<212> TYPE: DNA
<213> ORGANISM: Artificial Sequence
<220> FEATURE:
<223> OTHER INFORMATION: EF2_9_FOW

<400> SEQUENCE: 112
agccgaagcg tccagaac                                                 18

<210> SEQ ID NO 113
<211> LENGTH: 11
<212> TYPE: DNA
<213> ORGANISM: Artificial Sequence
<220> FEATURE:
<223> OTHER INFORMATION: EF2_1_fow

<400> SEQUENCE: 113
cagccgaagc g                                                        11

<210> SEQ ID NO 114
<211> LENGTH: 11
<212> TYPE: DNA
<213> ORGANISM: Artificial Sequence
<220> FEATURE:
<223> OTHER INFORMATION: EF2_2_fow

<400> SEQUENCE: 114
cagcccaagc g                                                        11

<210> SEQ ID NO 115
<211> LENGTH: 12
<212> TYPE: DNA
<213> ORGANISM: Artificial Sequence
<220> FEATURE:
<223> OTHER INFORMATION: EF2_3_fow

<400> SEQUENCE: 115
```
agccgaagcg yc                                                    12

<210> SEQ ID NO 116
<211> LENGTH: 13
<212> TYPE: DNA
<213> ORGANISM: Artificial Sequence
<220> FEATURE:
<223> OTHER INFORMATION: EF2_4_fow

<400> SEQUENCE: 116
agcccaagcg gcc                                                   13

<210> SEQ ID NO 117
<211> LENGTH: 13
<212> TYPE: DNA
<213> ORGANISM: Artificial Sequence
<220> FEATURE:
<223> OTHER INFORMATION: EF2_5_fow

<400> SEQUENCE: 117
agccgaagcg tcc                                                   13

<210> SEQ ID NO 118
<211> LENGTH: 13
<212> TYPE: DNA
<213> ORGANISM: Artificial Sequence
<220> FEATURE:
<223> OTHER INFORMATION: EF2_6_fow

<400> SEQUENCE: 118
agccgaagcg ccc                                                   13

<210> SEQ ID NO 119
<211> LENGTH: 15
<212> TYPE: DNA
<213> ORGANISM: Artificial Sequence
<220> FEATURE:
<223> OTHER INFORMATION: EF2_10_fow

<400> SEQUENCE: 119
agcgccccct gctcc                                                 15

<210> SEQ ID NO 120
<211> LENGTH: 16
<212> TYPE: DNA
<213> ORGANISM: Artificial Sequence
<220> FEATURE:
<223> OTHER INFORMATION: EF2_11_fow

<400> SEQUENCE: 120
cccgagcagc ccgacc                                                16

<210> SEQ ID NO 121
<211> LENGTH: 12
<212> TYPE: DNA
<213> ORGANISM: Artificial Sequence
<220> FEATURE:
<223> OTHER INFORMATION: EF2_1_rev

<400> SEQUENCE: 121
cgtgtgcgac gt                                                    12

<210> SEQ ID NO 122
<211> LENGTH: 12
<212> TYPE: DNA

```
<213> ORGANISM: Artificial Sequence
<220> FEATURE:
<223> OTHER INFORMATION: EF2_3_rev

<400> SEQUENCE: 122
cgtgagcgag tg                                                         12

<210> SEQ ID NO 123
<211> LENGTH: 12
<212> TYPE: DNA
<213> ORGANISM: Artificial Sequence
<220> FEATURE:
<223> OTHER INFORMATION: EF2_4_rev

<400> SEQUENCE: 123
cgtgwgcgac gt                                                         12

<210> SEQ ID NO 124
<211> LENGTH: 17
<212> TYPE: DNA
<213> ORGANISM: Artificial Sequence
<220> FEATURE:
<223> OTHER INFORMATION: EF2_7_rev

<400> SEQUENCE: 124
cgtgtgcgac gtgtccg                                                    17

<210> SEQ ID NO 125
<211> LENGTH: 19
<212> TYPE: DNA
<213> ORGANISM: Artificial Sequence
<220> FEATURE:
<223> OTHER INFORMATION: A.fum_EF2_2

<400> SEQUENCE: 125
cgacgctcac acctctgtc                                                  19

<210> SEQ ID NO 126
<211> LENGTH: 303
<212> TYPE: DNA
<213> ORGANISM: Candida albicans

<400> SEQUENCE: 126
attgaaacat gttattattt tgcaaaataa agttgatttg atgagagaag aatcagcctt     60
ggaacacgaa aaatctatca ttcagtttat tagaggtaca attgccgata atgctccgat    120
cgtgcctatt tctgctcaat tgaaatacaa cattgatgca gtgaatcaat ttattgttaa    180
ctacatacct gtgccaatga gagactttac tgcttcacca agattgatcg ttatcagatc    240
tttcgatgtg aacaagcctg gtgcagatgt agacgaattg aaaggaggtg ttgcaggtgg    300
ttc                                                                  303

<210> SEQ ID NO 127
<211> LENGTH: 303
<212> TYPE: DNA
<213> ORGANISM: Candida albicans

<400> SEQUENCE: 127
attgaaacat gttattattt tgcaaaataa agttgatttg atgagagaag aatcagcctt     60
ggaacacgaa aaatctatca ttcagtttat taraggtaca attgccgata atgctccgat    120
cgtgcctatt tctgctcaat traaatacaa cattgatgca gtgaatcaat ttatygttaa    180
ctacatacct gtgccaatga gagactttac tgcttcacca agattgatcg ttatcagatc    240
```

<210> SEQ ID NO 128
<211> LENGTH: 303
<212> TYPE: DNA
<213> ORGANISM: Candida albicans

<400> SEQUENCE: 128

```
attgaaacat gttattattt tgcaaaataa agttgatttg atgagagaag aatcagcytt    60
ggaacacgaa aaatctatya ttcagtttat taraggtaca attgccgata atgctccgat   120
cgtgcctatt tctgctcaat traaatacaa cattgatgca gtgaatcaat ttatygttaa   180
ctacataccT gtgccaatga gagactttac tgcttcacca agattgatcg ttatcagatc   240
tttcgatgtg aacaagcctg gtgcagatgt agacgaattg aaaggaggtg ttgcaggtgg   300
ttc                                                                 303
```

<210> SEQ ID NO 129
<211> LENGTH: 303
<212> TYPE: DNA
<213> ORGANISM: Candida albicans

<400> SEQUENCE: 129

```
attgaaacat gttattattt tgcaaaataa agttgatttg atgagagaag aatcagcctt    60
ggaacacgaa aaatctatca ttcagtttat tagaggtaca attgccgata atgctccgat   120
cgtgcctatt tctgctcaat tgaaatacaa cattgatgca gtgaatcaat ttattgttaa   180
ctacataccT gtgccaatga gagactttac tgcttcacca agattgatcg ttatcagatc   240
tttcgatgtg aacaagcctg gtgcagatgt agacgaattg aaaggaggtg ttgcaggtgg   300
ttc                                                                 303
```

<210> SEQ ID NO 130
<211> LENGTH: 303
<212> TYPE: DNA
<213> ORGANISM: Candida albicans

<400> SEQUENCE: 130

```
attgaaacat gttattattt tgcaaaataa agttgatttg atgagagaag aatcagcctt    60
ggaacacgaa aaatctatca ttcagtttat tagaggtaca attgccgata atgctccgat   120
cgtgcctatt tctgctcaat traaatacaa cattgatgca gtgaatcaat ttatygttaa   180
ctacataccT gtgccaatga gagactttac tgcttcacca agattgatcg ttatcagatc   240
tttcgatgtg aacaagcctg gtgcagatgt agacgaattg aaaggaggtg ttgcaggtgg   300
ttc                                                                 303
```

<210> SEQ ID NO 131
<211> LENGTH: 303
<212> TYPE: DNA
<213> ORGANISM: Candida albicans

<400> SEQUENCE: 131

```
attgaaacat gttattattt tgcaaaataa agttgatttg atgagagaag aatcagcctt    60
ggaacacgaa aaatctatca ttcagtttat taaaggtaca attgccgata atgctccgat   120
cgtgcctatt tctgctcaat tgaaatacaa cattgatgca gtgaatcaat ttattgttaa   180
```

```
ctacatacct gtgccaatga gagactttac tgcttcacca agattgatcg ttatcagatc    240
tttcgatgtg aacaagcctg gtgcagatgt agacgaattg aaaggaggtg ttgcaggtgg    300
ttc                                                                  303
```

<210> SEQ ID NO 132
<211> LENGTH: 303
<212> TYPE: DNA
<213> ORGANISM: Candida albicans

<400> SEQUENCE: 132

```
attgaaacat gttattattt tgcaaaataa agttgatttg atgagagaag aatcagcytt     60
ggaacacgaa aaatctatya ttcagtttat tagaggtaca attgccgata atgctccgat    120
cgtgcctatt tctgctcaat traaatacaa cattgatgca gtgaatcaat ttatygttaa    180
ctacatacct gtgccaatga gagactttac tgcttcacca agattgatcg ttatcagatc    240
tttcgatgtg aacaagcctg gtgcagatgt agacgaattg aaaggaggtg ttgcaggtgg    300
ttc                                                                  303
```

<210> SEQ ID NO 133
<211> LENGTH: 303
<212> TYPE: DNA
<213> ORGANISM: Candida albicans

<400> SEQUENCE: 133

```
attgaaacat gttattattt tgcaaaataa agttgatttg atgagagaag aatcagcctt     60
ggaacacgaa aaatctatca ttcagtttat taraggtaca attgccgata atgctccgat    120
cgtgcctatt tctgctcaat tgaaatacaa cattgatgca gtgaatcaat ttattgttaa    180
ctacatacct gtgccaatga gagactttac tgcttcacca agattgatcg ttatcagatc    240
tttcgatgtg aacaagcctg gtgcagatgt agacgaattg aaaggaggtg ttgcaggtgg    300
ttc                                                                  303
```

<210> SEQ ID NO 134
<211> LENGTH: 303
<212> TYPE: DNA
<213> ORGANISM: Candida albicans

<400> SEQUENCE: 134

```
attgaaacat gttattattt tgcaaaataa agttgatttg atgagagaag aatcagcctt     60
ggaacacgaa aaatctatca ttcagtttat taraggtaca attgccgata atgctccgat    120
cgtgcctatt tctgctcaat tgaaatacaa cattgatgca gtgaatcaat ttattgttaa    180
ctacatacct gtgccaatga gagactttac tgcttcacca agattgatcg ttatcagatc    240
tttcgatgtg aacaagcctg gtgcagatgt agacgaattg aaaggaggtg ttgcaggtgg    300
ttc                                                                  303
```

<210> SEQ ID NO 135
<211> LENGTH: 23
<212> TYPE: DNA
<213> ORGANISM: Artificial Sequence
<220> FEATURE:
<223> OTHER INFORMATION: CEF1F

<400> SEQUENCE: 135

```
atctatcatt cagtttatta gag                                             23
```

```
<210> SEQ ID NO 136
<211> LENGTH: 21
<212> TYPE: DNA
<213> ORGANISM: Artificial Sequence
<220> FEATURE:
<223> OTHER INFORMATION: CEF2F

<400> SEQUENCE: 136
cattcagttt attagaggta c                                              21

<210> SEQ ID NO 137
<211> LENGTH: 18
<212> TYPE: DNA
<213> ORGANISM: Artificial Sequence
<220> FEATURE:
<223> OTHER INFORMATION: CEFR2

<400> SEQUENCE: 137
cagtaaagtc tctcattg                                                  18

<210> SEQ ID NO 138
<211> LENGTH: 19
<212> TYPE: DNA
<213> ORGANISM: Artificial Sequence
<220> FEATURE:
<223> OTHER INFORMATION: ALEF1

<400> SEQUENCE: 138
tgccgataat gctccgatc                                                 19

<210> SEQ ID NO 139
<211> LENGTH: 1605
<212> TYPE: DNA
<213> ORGANISM: Candida albicans

<400> SEQUENCE: 139
atgtcatacg acgatataga aaatgccact cctgatattg ttattgggag tactatagag    60
gaacctgaag aagattacca agtggaaagt gacaatgagt acaagccgc agaccatgag    120 tcatcgcaaa taaatgaaga atcagccaaa ggcaaaaagt cagttgcatt tactggattg    180
gatgaagacg aggaaaatgc agaggaattg gccagaaagg agtttgaaga aggtggtgga    240
ttgcctgaac aaccagaaaa cccagatttc aatgagttaa caccctttatc tcccgagatt    300 atcaacaggc aagccaccat taatattggt accattggtc atgtcgccca cgggaagtct    360
actgttgtca gggctatctc tggtgtccag accgttcgtt tcaaggatga attagaaaga    420
aacattacta tcaagttagg ttacgccaat gccaaaattt acaaatgtga taacccagag    480
tgtccagaac cagattgtta cagatcattc aaatcagata aggaaataag accaaaatgt    540
caaagagctg gctgtgacgg tcgctacaaa ttgttaagac atgtctcttt tgttgattgt    600
ccaggacatg atattttgat gagtactatg ttgtcaggtg ctgccgtgat ggatgccgcc    660
ttgttgttga ttgccggtaa tgaaagttgt ccacaacccc agacttctga gcatttggct    720
gccattgaaa ttatgaaatt gaaacatgtt attattttgc aaaataaagt tgatttgatg    780
agagaagaat cagccttgga acacgaaaaa tctatcattc agtttattag aggtacaatt    840
gccgataatg ctccgatcgt gcctatttct gctcaattga aatacaacat tgatgcagtg    900
aatcaattta tgttaactaa catacctgtg ccaatgagag actttactgc ttcaccaaga    960
ttgatcgtta tcagatcttt tcgatgtgaac aagcctggtg cagatgtaga cgaattgaaa    1020
ggaggtgttg caggtggttc tattttgact ggtgttttta agattggtga tgagatcgag    1080
```

| | |
|---|---:|
| attagacctg gtatcgtcac caaagatgat caaggaaaga ttcaatgtaa acctatattc | 1140 |
| tcgaacgtgg tttccttgtt tgctgagcat aacgatttga aatttgctgt tcctggtggt | 1200 |
| ttgattggtg ttggtactaa agttgatcct acgttgtgta gggctgatag attggttggt | 1260 |
| caagttgttg gtgcaaaagg aaacttgccc tctatttacg ctgatattga gataaactat | 1320 |
| ttcctattaa gaagattgtt gggtgtcaaa actgaaggtc aaaagcaagg tgctaaagtt | 1380 |
| cgtaagttgg aacaatctga agtgttgatg gtaaatattg gttctactgc aactggtgct | 1440 |
| agagtggttg ctgttaaagc agatatggct cgtttacaat tgactacacc agcctgtaca | 1500 |
| gaaatcaacg aaaaaattgc gttgtctaga cgtattgaaa agcattggcg tttgattggt | 1560 |
| tgggccacta tcaagaaagg tacagcatta gaaccaattt cttaa | 1605 |

<210> SEQ ID NO 140
<211> LENGTH: 1498
<212> TYPE: DNA
<213> ORGANISM: Aspergillus fumigatus

<400> SEQUENCE: 140

| | |
|---|---:|
| gttggatgcg gcgaacggcc aggatgatat tgaagaacag gaacgtcttg acgtggaaga | 60 |
| gaagcccctt aagtctgcga tgaagaaagg tgcagcgccc cctgctcctc agccgaagcg | 120 |
| tccagaactc cccgagcagc ccgacccaga gactctcgat ttgtcgacgc tcacacctct | 180 |
| gtcgcccgaa attattgcgc gccaggccac aatcaacatc ggtactatcg acacgtcgc | 240 |
| acacggcaag tcgactgttg tgaaggctat ctcggaggtg cagactgtcc ggttcaaaaa | 300 |
| tgagttggag cgtaacatta ccatcaagct tggttatgcc aacgcgaaga tctacaagtg | 360 |
| cgacaaccct gggtgcccgc gcccgacgtg cttcaagagt tacaagagtg agaaggagat | 420 |
| cgaccctcca tgtgagagag aaggatgcac aggtcgttac agattgttga acatgtctc | 480 |
| gttcgttgac tgccctgggc acgatattct catgagtacc atgttgtcag gtgccgccgt | 540 |
| catggacgcc gccctttttgc tgattgccgg aaacgaagct tgcccccagc ctcagacttc | 600 |
| ggagcactta gcagctattg aaatcatgaa gctcagccat atcatcattc tgcagaacaa | 660 |
| ggttgatctg atgagggaag acggtgctct gcaacattac caatcaatcc tgaagttcat | 720 |
| tcgtggtact gttgccgatg gctctcctat cattcccatc tctgctcagc tcaagtacaa | 780 |
| catcgacgct gtcaacgaat accttgtctc gcacatccca gttcccgtcc gtgcttcac | 840 |
| tgcttcgcct cacatgattg tcattcgttc cttcgacgtc aacaaacccg gtgcggagat | 900 |
| cgatgagttg aagggtggtg ttgcaggtgg ctctatcctc actggtgtgc tgaagctgaa | 960 |
| cgacgagatt gaaattcgcc ccggtctcgt taccaaggat gagaacggaa agattcagtg | 1020 |
| ccgcccatc ttctcccgtg tcgtctcgct cttcgctgag cacaacgatc tgaagttcgc | 1080 |
| tgtccctggt ggtctaatcg gtgtcggaac ccgtgtcgac cctaccctgt gccgtgccga | 1140 |
| tcgtcttgtt ggtttcgtcc tgggtcaccg tggccgtttg ccagccatct acactgaact | 1200 |
| ggaggtcaac tacttcctcc tgcgtcgtct gctcggtgtc aagaccgccg acggcaagca | 1260 |
| ggccaaggtc gccaagctca ccaagaacga agtcctcatg gttaacatcg gctctacggc | 1320 |
| tactggtgct aaggttatgg gtgtgaaggc tgatgctgcc aagctcagct tgaccagccc | 1380 |
| ggcttgtaca gagattggag agaagattgc tatcagccgg agaattgaca agcattggcg | 1440 |
| tctgatcggc tgggccaaca ttgtcgctgg caacactctt gagcccattc tgaactag | 1498 |

<210> SEQ ID NO 141
<211> LENGTH: 1605

```
<212> TYPE: DNA
<213> ORGANISM: Candida albicans

<400> SEQUENCE: 141
atgtcatacg acgatataga aaatgccact cctgatattg ttattgggag tactatagag      60
gaacctgaag aagattacca agtggaaagt gacaatgagt tacaagccgc agaccatgag     120
tcatcgcaaa taaatgaaga atcagccaaa ggcaaaaagt cagttgcatt tactggattg     180
gatgaagacg aggaaaatgc agaggaattg gccagaaagg agtttgaaga aggtggtgga     240
ttgcctgaac aaccagaaaa cccagatttc aatgagttaa cacctttatc tcccgagatt     300
atcaacaggc aagccaccat taatattggt accattggtc atgtcgccca cgggaagtct     360
actgttgtca gggctatctc tggtgtccag accgttcgtt tcaaggatga attagaaaga     420
aacattacta tcaagttagg ttacgccaat gccaaaattt acaaatgtga tacccagag      480 tgtccagaac cagattgtta cagatcattc aaatcagata aggaaataag accaaaatgt     540
caaagagctg gctgtgacgg tcgctacaaa ttgttaagac atgtctcttt tgttgattgt     600
ccaggacatg atattttgat gagtactatg ttgtcaggtg ctgccgtgat ggatgccgcc     660
ttgttgttga ttgccggtaa tgaaagttgt ccacaacccc agacttctga gcatttggct     720
gccattgaaa ttatgaaatt gaaacatgtt attattttgc aaaataaagt tgatttgatg     780
agagaagaat cagccttgga acacgaaaaa tctatcattc agtttattag aggtacaatt     840
gccgataatg ctccgatcgt gcctatttct gctcaattga atacaacat tgatgcagtg      900 aatcaattta ttgttaacta catacctgtg ccaatgagag actttactgc ttcaccaaga     960
ttgatcgtta tcagatcttt cgatgtgaac aagcctggtg cagatgtaga cgaattgaaa    1020
ggaggtgttg caggtggttc tattttgact ggtgttttta agattggtga tgagatcgag    1080
attagacctg gtatcgtcac caaagatgat caaggaaaga ttcaatgtaa acctatattc    1140
tcgaacgtgg tttccttgtt tgctgagcat aacgatttga aatttgctgt tcctggtggt    1200
ttgattggtg ttggtactaa agttgatcct acgttgtgta gggctgatag attggttggt    1260
caagttgttg gtgcaaaagg aaacttgccc tctatttacg ctgatattga gataaactat    1320
ttcctattaa gaagattgtt gggtgtcaaa actgaaggtc aaaagcaagg tgctaaagtt    1380
cgtaagttgg aacaatctga agtgttgatg gtaaatattg gttctactgc aactggtgct    1440
agagtggttg ctgttaaagc agatatggct cgtttacaat gactacacc agcctgtaca     1500 gaaatcaacg aaaaaattgc gttgtctaga cgtattgaaa agcattggcg tttgattggt    1560
tgggccacta tcaagaaagg tacagcatta gaaccaattt cttaa                   1605

<210> SEQ ID NO 142
<211> LENGTH: 1557
<212> TYPE: DNA
<213> ORGANISM: Candida glabrata

<400> SEQUENCE: 142
atgtctgatt tgcaagatca agagccaact attattatca atggtgatct tccaccagta     60
gaagaagagg aagtctatga gcaggaagag caagaggaag ttgttgagga gaagccaaag    120
aagaaagttg cctttaccgg tctagaggat ggtgaatctg aggaagagaa gagaaagaga    180
gagtttgaag aaggtggtgg attgccagag cagccagaaa acccagactt tactaagttg    240
aacccacttt ctgctgagat tattaacaga caagctacta tcaacatcgg tactattggt    300
catgtcgctc acggtaagtc tactgttgtc agagccatct ctggtgtcca aaccgttcgt    360
```

```
ttcaaggatg agttggaacg taacattact atcaagctgg ttatgccaa tgctaagata      420 tataagtgtc aagagcctac atgtccagaa ccagactgtt acagatcttt caagtctgac      480
aaagaaatta atccaaagtg tcaaagacca ggttgcccag gccgttacaa acttgttcgt      540
cacgtctctt tcgtcgattg tccaggtcac gatattctaa tgagtactat gttgtccggt      600
gccgctgtca tggacgcagc cttgttattg atcgccggta atgaatcttg tccacaacct      660
caaacttctg aacatttggc tgccattgaa atcatgaagt taaagcacgt tattattcta      720
cagaacaagg tcgatttaat gcgtgaagaa agcgcactag aacatgaaaa gtctatcctg      780
aaatttatca gaggtactat tgctgacggt gctccaattg tcccaatttc cgctcaattg      840
aaatacaaca tcgatgcagt caatgaattt atcgtgaaga ctatccctgt tccaccaaga      900
gatttcatgc tttctccacg tttgattgtc attcgttctt tcgatgttaa caagccaggt      960
gctgaaatcg atgatttgaa gggtggtgtt gcaggtggtt ccatcttgaa cggtgtgttc     1020
aagttgggtg atgagattga aattagacca ggtattgtca ctaaggatga taagggtaag     1080
atccaatgta agccaatttt ctccaacatt gtctctctat ttgctgaaca aaatgacttg     1140
aagtttgcag tcccaggtgg tctgattggt gttggtacaa aggtcgatcc taccttatgt     1200
agagctgatc gtcttgtcgg tcaagttgtc ggtgccaagg tcacctacc aagcatttac     1260 acagatattg aaatcaacta cttcctactg cgtcgtctat taggtgttaa gactgagaaa     1320
caagccaagt tcagaaagct ggttgccaac gaagttctta tggttaacat tggttctact     1380
gccactggtg cccgtgtcgt tgctgtcaag gctgatatgg ctagattgca actaacatcc     1440
ccagcatgta cagaaatcaa tgaaaagatt gctctctcta gacgtattga caagcactgg     1500
cgtttaattg gttgggctac aatcaagaaa ggtaccactt tggaaccagt tgtctaa         1557

<210> SEQ ID NO 143
<211> LENGTH: 303
<212> TYPE: DNA
<213> ORGANISM: Candida parapsilosis

<400> SEQUENCE: 143
gttgaagcac gttattattt tgcaaaacaa agttgattta atgagaaagg agtcagcttt       60
ggaacatgaa aagtccatca ttcagttcat cagaggtact atagctgatg gtgccccaat      120
tgttccaatt tcagcacaat tgaagtataa atcgacgcc gtcaatcaat tcatcgtaaa      180
ctcaatacca gttccagtca gggactttac tgcatcccct aggttaattg ttattaggtc      240
ttttgatgtg aacaaacctg gtgctgacgt tgatgatttg aaaggaggtg ttgcaggtgg      300
ttc                                                                   303

<210> SEQ ID NO 144
<211> LENGTH: 293
<212> TYPE: DNA
<213> ORGANISM: Candida tropicalis

<400> SEQUENCE: 144
gtcatkattt tgcagaacaa ggtcgatttg atgagagaag aatctgcctt ggaacatgag       60
aaatccattc ttcaattcat cagaggtact attgcagaca atgctcctat tgtcccaatt      120
tctgcccaat tgaaatacaa catcgatgcc gttaaccaat ttattgtcaa ttatatccca      180
gttccattga gagactttc cgcttcccca agattgattg tcatcagatc ttttgatgtc      240
aacaagccag gttccgatgt cgaagacttg aaggggggtg ttgcaggtgg ttc             293
```

<210> SEQ ID NO 145
<211> LENGTH: 294
<212> TYPE: DNA
<213> ORGANISM: Candida kruisi

<400> SEQUENCE: 145

```
tgktgtgatt ktacaaaata aagttgattt gatgaagaaa gaagcagctt tagagcacga    60
aaaatctatt ttgaagttta tcaagggtac tattgctgat ggtgctccta ttatcccaat   120
ttctgctcag ttgaaatata acattgatgc agttaacatg tgtatggtca agtctattcc   180
tgttccaatt agagacttta ccgcagttcc aagattaatg gttattagat ctttcgatgt   240
taataagcct ggtgcagaaa ttgcagattt gaaaggtggt gttgcaggtg gttc          294
```

<210> SEQ ID NO 146
<211> LENGTH: 228
<212> TYPE: DNA
<213> ORGANISM: Aspergillus fumigatus

<400> SEQUENCE: 146

```
agcgccccct gctcctcagc cgaagcgtcc agaactcccc gagcagcccg acccagagac    60
tctcgatttg tcgacgctca cctctgtc gcccgaaatt attgcgcgcc aggccacaat    120
caacatcggt actatcggac acgtcgcaca cggcaagtcg actgttgtga aggctatctc   180
ggaggtgcag actgtccggt tcaaaaatga gttggagcgt aacattac                228
```

<210> SEQ ID NO 147
<211> LENGTH: 230
<212> TYPE: DNA
<213> ORGANISM: Aspergillus flavus

<400> SEQUENCE: 147

```
gctgtaccc ctgtttctca gcccaagcgg ccagagttgc ccgaacagcc agacccgct    60 acccttgacc tgtcgaccct gaccctctg tcgcccgaaa tcattgcgcg ccaggccact   120
attaacattg gtaccatcgg acacgtcgct cacggaaagt caacagtggt caaggctatc   180
tcagaggttc agactgtccg tttcaaaaac gagttggagc gtaacattac              230
```

<210> SEQ ID NO 148
<211> LENGTH: 223
<212> TYPE: DNA
<213> ORGANISM: Aspergillus niger

<400> SEQUENCE: 148

```
ttcctcctcc ccagcccaag cggccagagc tgcccgagca gccgaatccg gagactctgg    60
acctgtccac cctgactcct tgaccccg aaattattgc gcgccaagcc acaatcaaca   120
ttggcaccat cggtcacgtc gctcacggca agtcgacggt cgttaaggct atctccgagg   180
tccagactgt ccgtttcaag aacgagttgg agcgtaacat tac                     223
```

<210> SEQ ID NO 149
<211> LENGTH: 211
<212> TYPE: DNA
<213> ORGANISM: Aspergillus terreus

<400> SEQUENCE: 149

```
agccgaagcg cccagagctt cctgaacaac ccaacccaga caccctcgat ctgtcgacgc    60
ttacccctct gtcgcccgaa attattgcgc gccaggccac catcaacatc ggtaccattg   120
```

```
gtcacgtcgc tcacggaaag tcgacggttg tcaaggccat ctcagaggtc cagaccgttc    180
gattcaagaa cgagttggag cgtaacatta c                                  211
```